United States Patent
Chen et al.

(10) Patent No.: US 12,116,572 B2
(45) Date of Patent: *Oct. 15, 2024

(54) TARGET BINDING MOIETY COMPOSITIONS AND METHODS OF USE

(71) Applicant: Guangzhou Chengyuan Bioimmunology Technology Co., Ltd., Guangdong (CN)

(72) Inventors: Xi Chen, Newton, MA (US); Ely Porter, Medford, MA (US)

(73) Assignee: Guangzhou Chengyuan Bioimmunology Technology Co., Ltd., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/066,463

(22) Filed: Dec. 15, 2022

(65) Prior Publication Data

US 2023/0279384 A1 Sep. 7, 2023

Related U.S. Application Data

(63) Continuation of application No. 17/031,260, filed on Sep. 24, 2020, now Pat. No. 11,560,560, which is a continuation of application No. PCT/US2019/023820, filed on Mar. 25, 2019.

(60) Provisional application No. 62/686,858, filed on Jun. 19, 2018, provisional application No. 62/648,218, filed on Mar. 26, 2018.

(51) Int. Cl.
C12N 15/10 (2006.01)
G01N 33/68 (2006.01)

(52) U.S. Cl.
CPC ..... *C12N 15/1065* (2013.01); *G01N 33/6854* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 4,672,040 A | 6/1987 | Josephson | |
| 4,681,870 A | 7/1987 | Balint, Jr. et al. | |
| 6,133,043 A | 10/2000 | Talley et al. | |
| 6,281,344 B1 | 8/2001 | Szostak et al. | |
| 6,396,995 B1 | 5/2002 | Stuelpnagel et al. | |
| 6,544,732 B1 | 4/2003 | Chee et al. | |
| 2003/0235852 A1 | 12/2003 | Roberts et al. | |
| 2004/0253612 A1 | 12/2004 | Szostak et al. | |
| 2009/0186984 A1 | 7/2009 | Harris et al. | |
| 2017/0107566 A1 | 4/2017 | Church et al. | |
| 2017/0343541 A1 | 11/2017 | Johnston et al. | |

FOREIGN PATENT DOCUMENTS

| | | | |
|---|---|---|---|
| WO | WO2011034605 | * | 3/2011 |
| WO | WO-2019190954 A1 | | 10/2019 |

OTHER PUBLICATIONS

Fukuda et al (Nucleic Acids Research vol. 34 No. 19 e127; 8 pages) (Year: 2006).*
Bentley, et al., "Accurate Whole Human Genome Sequencing Using Reversible Terminator Chemistry" Nature (2008), 456(7218): 53-59.
Betz, et al., "KlenTaq polymerase replicates unnatural base pairs by inducing a Watson-Crick geometry" National Chemical Biology (2012) 8(7) pp. 612-614.
Brenner, "A cultivated taste for yeast," Genome Biol.1:1 (2000).
Brenner, "Chemical genomics in yeast" Genome Biol. 5:240 (2004).
Brenner, et al., Gene Expression analysis by massively parallel signature sequencing (MPSS) on microbead arrays. Nature Biotechnology 18.6 (Jun. 2000): 630-634, doi:10.1038/76469.
Case-Green, et al., "Analysing genetic information with DNA arrays" Combinatorial Chemistry, pp. 404-410.
Chin, et al., "Addition of p-Azido-L-phenylalanine to the Genetic Code of *Escherichia coli*", JACS, (2002) 124, 9026-9027.
Chin, et al., "An Expanded Eukaryotic Genetic Code" Science (2003) vol. 301 pp. 964-967.
Chiu, et al. "Noninvasive prenatal diagnosis of fetal chromosomal aneuploidy by massively parallel genomic sequencing of DNA in maternal plasma" PNAS, (2008) vol. 105, No. 51, pp. 20458-20463.
Chothia, et al., "Canonical Structures for the Hypervariable Regions of Immunoglobulins" J. Mol. Biol. (1987) 196, 901-917.
Clackson, et al., "Making antibody fragments using phage display libraries Nature, vol. 352, (1991)".
Clark, et al., "Design, synthesis and selection of DNA-encoded small-molecule libraries, Nature Chemical Biology, vol. 5, No. 9 (2009) pp. 647-772".
Davis, et al., "Local myocardial insulin-like growth factor 1 (IGF-1) delivery with biotinylated peptide nanofibers improves cell therapy for myocardial infarction PNAS, (2006) vol. 103, No. 21, pp. 8158-8160".
Eason, et al., "Characterization of synthetic DNA bar codes in *Saccharomyces cerevisiae* gene-deletion strains PNAS (2004), vol. 101, No. 30, pp. 11046-11051".
Ellman, et al., "Biosynthetic Method for Introducing Unnatural Amino Acides Site-Specifically into Proteins Methods in Enzymology, vol. 202, (1991)".

(Continued)

*Primary Examiner* — Christopher M Gross

(74) *Attorney, Agent, or Firm* — Wilson Sonsini Goodrich & Rosati

(57) ABSTRACT

Provided herein are compositions and methods to identify a binding element (e.g., peptide, peptoid, or protein) that can be bound by an immunoreceptor (e.g., antibody). The binding element can be provided in a target binding unit comprising two binding elements separated by a spacer such that the two binding elements simultaneously bind to a single molecule comprising an antigen binding domain of an antibody. The present disclosure provides various methods to construct the spacer. The identified binding elements can be further used to manufacture an array which can be used to profile antibodies obtained from a blood sample.

20 Claims, 17 Drawing Sheets

Specification includes a Sequence Listing.

(56) References Cited

OTHER PUBLICATIONS

EP Application No. 19776940.9 Supplementary Extended European Search Report dated Oct. 22, 2021.
Fan et al. Noninvasive diagnosis of fetal aneuploidy by shotgun sequencing DNA from maternal blood. PNAS 105:16266-16271 (2008).
Fransson, et al., "Humanization of antibodies Frontiers in Bioscience 13, 1619-1633 (2008)".
Gaiever, et al., "Chemogenomic profiling: Identifying the functional interactions of small molecules in yeast PNAS (2004) vol. 101, No. 3, pp. 793-798".
Griffiths, et al., "Man-made enzyme-from design to in vitro compartmentalisation Elsevier Science Ltd (2000) pp. 338-353".
International Search Report and Written Opinion dated Jul. 25, 2019, for PCT/US19/23820.
Janssen et al.: Reversible blocking of antibodies using bivalent peptide-DNA conjugates allows protease-activatable targeting. Chemical Science 4(4):1442-1450 DOI:10.1039/c3sc22033h (2013).
Kindt et al,. Kuby Immunology, 6th ed., W.H. Freeman and Co., p. 91, (2007).
"Kozarewa, et al., "Amplification-free Illumina sequencing-library preparation facilitates improved mapping and assembly of GC-biased genomes" National Methods (2009) 6(4): 291-295".
"Krayevsky, et al., "The Peptidyl transferase Center of Ribosomes" (1979) Progress in Nucleic Acid Research and Molecular Biology, vol. 23 pp. 1-51".
Kumar et al., "Emerging technologies in yeast genomics," Nature Rev. 2:302 (2001).
"Mahal, et al., "Engineering Chemical Reactivity on Cell Surfaces Through Oligosaccharide Biosynthesis" Science (1997) vol. 276, pp. 1125-1128".
"Metzker, Michael L., "Sequencing technologies-the next generation" Genetics (2010) vol. 11 pp. 31-46".
"Smith, et al., "Action of Puromycin in Polyadenylic Synthesis" J. Mol. Bio. (1965) 13, 617- 628".
"No Author "Going Global" Nature Genetics, (1999) vol. 21, No. 1".
"Portolano, et al., "Lack of promiscuity in autoantigen-specific H and L chain combinations as revealed by human H and L chain roulette", Journal of Immunology (1993); 150:880-887".
"Reddy, et al., "Identification of Candidate IgG Biomarkers for Alzheimer's Disease via Combinatorial Library Screening" Cell 144 132-142, (2011)".
"Rostovtsev, et al., A Stepwise Huisgen Cycloadditional Process: Copper(I)-Catalyzed Regioselective "Litigation" of Azides and Terminal Alkynes** Angew. Chem. Int. Ed (2002) 41, No. 14".
"Thermo Scientific Crosslinking Technical Handbook, East Molecular bonding crosslinking technology, (2012) pp. 1-56".
"Tornoe, et al., "Peptidotriazoles on Solid Phase: [1,2,3]-Triazoles by Regiospecific Cooper(I)-Catalyzed 1,3-Dipolar Cycloadditional of Terminal Alkynes to Azides" J. Org. Chem (2002), 67, 3057-3064".
"Traut, et al., "The Puromycin Reaction and its Relation to Protein Synthesis" J. Mol. Biol. (1964) 10, 63-72".
"Voelkerding, et al., "Next-Generation Sequencing: From Basic Research to Diagnostic" Clinical Chemistry (2009) 55:4 641-658".
"Wang, et al., "Bioconjugation by Cooper(I)-Catalyzed Azide-Alkyne [3+2] Cycloaddition"".
"Wentworth, et al. "Recent developments and applications on liquid-phase strategies in organic synthesis" Tibtech (1999) vol. 17, pp. 448-452".
Winzeler et al.: Functional characterization of the S. cerevisiae genome by gene deletion and parallel analysis. Science 285(5429):901-906 doi:10.1126/science.285.5429.901 (1999).
Zandian, et al., "Whole-Proteome Peptide Microarrays for Profiling Autoantibody Repertoires within Multiple Sclerosis and Narcolepsy Journal of proteome research, (2017) vole 16, pp. 1300-1314".

\* cited by examiner (a)

(b)

SEQUENCE LISTING

```
Sequence total quantity: 35
SEQ ID NO: 1              moltype = AA   length = 5
FEATURE                   Location/Qualifiers
source                    1..5
                          mol_type = protein
                          organism = synthetic construct
SEQUENCE: 1
GGGGS                                                                5

SEQ ID NO: 2              moltype = DNA  length = 536
FEATURE                   Location/Qualifiers
```

```
source                    1..536
                          mol_type = other DNA
                          organism = synthetic construct
SEQUENCE: 2
aaaattaata cgactcacta tagggagaat aaacgactca ctattgcccg atagtagata    60
ataaggaggt aaaaatgggc agccatcatc atcatcatca cgagaacctg tacttccaat   120
ccgcgtccgg atctagtggc gactacaaag acgatgacga taaatcatca ggtagcggta   180
gcagtcgact ccttgaaatt gaattgcaat cacaactgtc gatgaaggct tccctggaaa   240
actcgttaga agagactaag gacgatatg cgatgcagct tgctcagatt caggagatga   300
ttggaagtgt ggaggagcaa ctggcccaat tacgttgtga aatggaacaa cagaatcagg   360
aatataaaat tttgctggac gtcaagacac gattggaaca ggagattgca acgtatcgtc   420
gtttgttaga aggggaagag tcgggagcgt ccggatctag tggcgactac aaagacgatg   480
acgataaatc atccggtagc ggtagcggta gcgtgagtag cggtggtagt agtaaa       536

SEQ ID NO: 3              moltype = DNA   length = 25
FEATURE                   Location/Qualifiers
modified_base             7
                          mod_base = OTHER
                          note = thymine with internal azide modification
source                    1..25
                          mol_type = other DNA
                          organism = synthetic construct
SEQUENCE: 3
ccgaaatact actaccaccg ctact                                          25

SEQ ID NO: 4              moltype = DNA   length = 225
FEATURE                   Location/Qualifiers
source                    1..225
                          mol_type = other DNA
                          organism = synthetic construct
SEQUENCE: 4
cttgaaattg aattgcaatc acaactgtcg atgaaggctt ccctggaaaa ctcgttagaa    60
gagactaagg acgatatgc gatgcagctt gctcagattc aggagatgat tggaagtgt   120
gaggagcaac tggcccaatt acgttgtgaa atggaacaac agaatcagga atataaaatt   180
ttgctggacg tcaagacacg attggaacag gagattgcaa cgtat                   225

SEQ ID NO: 5              moltype = DNA   length = 18
FEATURE                   Location/Qualifiers
source                    1..18
                          mol_type = other DNA
                          organism = synthetic construct
SEQUENCE: 5
tcatcaggta gcggtagc                                                  18

SEQ ID NO: 6              moltype = DNA   length = 21
FEATURE                   Location/Qualifiers
source                    1..21
                          mol_type = other DNA
                          organism = synthetic construct
SEQUENCE: 6
cgtcgtttgt tagaagggga a                                              21

SEQ ID NO: 7              moltype = DNA   length = 18
FEATURE                   Location/Qualifiers
modified_base             4
                          mod_base = OTHER
                          note = internal deoxy-uridine
modified_base             8
                          mod_base = OTHER
                          note = internal deoxy-uridine
modified_base             14
                          mod_base = OTHER
                          note = internal deoxy-uridine
source                    1..18
                          mol_type = other DNA
                          organism = synthetic construct
SEQUENCE: 7
tcatcaggta gcggtagc                                                  18

SEQ ID NO: 8              moltype = DNA   length = 23
FEATURE                   Location/Qualifiers
modified_base             1..7
                          mod_base = OTHER
                          note = Phosphorothioate linkage
modified_base             7
                          mod_base = OTHER
                          note = internal deoxy-uridine
source                    1..23
                          mol_type = other DNA
```

```
                           organism = synthetic construct
SEQUENCE: 8
gacaagtgag tcgggagcgt ccg                                              23

SEQ ID NO: 9            moltype = DNA   length = 18
FEATURE                 Location/Qualifiers
source                  1..18
                        mol_type = other DNA
                        organism = synthetic construct
SEQUENCE: 9
gcgtccggat ctagtggc                                                    18

SEQ ID NO: 10           moltype = DNA   length = 12
FEATURE                 Location/Qualifiers
source                  1..12
                        mol_type = other DNA
                        organism = synthetic construct
SEQUENCE: 10
gagtcgggag cg                                                          12

SEQ ID NO: 11           moltype = DNA   length = 15
FEATURE                 Location/Qualifiers
source                  1..15
                        mol_type = other DNA
                        organism = synthetic construct
SEQUENCE: 11
tccggatcta gtggc                                                       15

SEQ ID NO: 12           moltype = DNA   length = 18
FEATURE                 Location/Qualifiers
modified_base           4
                        mod_base = OTHER
                        note = internal deoxy-uridine
modified_base           10
                        mod_base = OTHER
                        note = internal deoxy-uridine
modified_base           14
                        mod_base = OTHER
                        note = internal deoxy-uridine
source                  1..18
                        mol_type = other DNA
                        organism = synthetic construct
SEQUENCE: 12
gcgtccggat ctagtggc                                                    18

SEQ ID NO: 13           moltype = DNA   length = 18
FEATURE                 Location/Qualifiers
modified_base           3
                        mod_base = OTHER
                        note = internal deoxy-uridine
modified_base           9
                        mod_base = OTHER
                        note = internal deoxy-uridine
modified_base           16
                        mod_base = OTHER
                        note = internal deoxy-uridine
source                  1..18
                        mol_type = other DNA
                        organism = synthetic construct
SEQUENCE: 13
gctaccgcta ccggatga                                                    18

SEQ ID NO: 14           moltype = DNA   length = 137
FEATURE                 Location/Qualifiers
source                  1..137
                        mol_type = other DNA
                        organism = synthetic construct
SEQUENCE: 14
aaaattaata cgactcacta tagggagaat aaacgactca ctattgcccg atagtagata      60
ataaggaggt aaaaatgggc agccatcatc atcatcatca cgagaacctg tacttccaat     120
ccgcgtccgg atctagt                                                    137

SEQ ID NO: 15           moltype = DNA   length = 46
FEATURE                 Location/Qualifiers
source                  1..46
                        mol_type = other DNA
                        organism = synthetic construct
SEQUENCE: 15
tttactacta ccaccgctac tcacgctacc gctaccgcta ccggat                     46
```

```
SEQ ID NO: 16           moltype = AA   length = 84
FEATURE                 Location/Qualifiers
source                  1..84
                        mol_type = protein
                        organism = synthetic construct
SEQUENCE: 16
QRLRAEIDNV KKQCANLQNA IADAEQRGEL ALKDARNKLA ELEEALQKAK QDMARLLREY   60
QELMNTKLAL DVEIATYRKL LEGE                                          84

SEQ ID NO: 17           moltype = AA   length = 82
FEATURE                 Location/Qualifiers
source                  1..82
                        mol_type = protein
                        organism = synthetic construct
SEQUENCE: 17
LEIELQSQLS MKASLENSLE ETKGRYAMQL AQIQEMIGSV EEQLAQLRCE MEQQNQEYKI   60
LLDVKTRLEQ EIATYRRLLE GE                                            82

SEQ ID NO: 18           moltype = DNA   length = 122
FEATURE                 Location/Qualifiers
source                  1..122
                        mol_type = other DNA
                        organism = synthetic construct
SEQUENCE: 18
aaaattaata cgactcacta tagggagaat aaacgactca ctattgcccg atagtagata   60
ataaggaggt aaaaatgggc agccatcatc atcatcatca cgagaacctg tacttccaat  120
cc                                                                 122

SEQ ID NO: 19           moltype = DNA   length = 30
FEATURE                 Location/Qualifiers
source                  1..30
                        mol_type = other DNA
                        organism = synthetic construct
SEQUENCE: 19
ggtagcgtga gtagcggtgg tagtagtaaa                                    30

SEQ ID NO: 20           moltype = DNA   length = 20
FEATURE                 Location/Qualifiers
source                  1..20
                        mol_type = other DNA
                        organism = synthetic construct
SEQUENCE: 20
cttgaaattg aattgcaatc                                               20

SEQ ID NO: 21           moltype = DNA   length = 25
FEATURE                 Location/Qualifiers
source                  1..25
                        mol_type = other DNA
                        organism = synthetic construct
SEQUENCE: 21
aaaattaata cgactcacta taggg                                         25

SEQ ID NO: 22           moltype = DNA   length = 24
FEATURE                 Location/Qualifiers
source                  1..24
                        mol_type = other DNA
                        organism = synthetic construct
SEQUENCE: 22
gactacaaag acgatgacga taaa                                          24

SEQ ID NO: 23           moltype = DNA   length = 273
FEATURE                 Location/Qualifiers
source                  1..273
                        mol_type = other DNA
                        organism = synthetic construct
SEQUENCE: 23
tcatcaggta gcggtagcag tcgactcctt gaaattgaat tgcaatcaca actgtcgatg   60
aaggcttccc tggaaaactc gttagaagag actaagggac gatatgcgat gcagcttgct  120
cagattcagg agatgattgg aagtgtggag gagcaactgg cccaattacg ttgtgaaatg  180
gaacaacaga atcaggaata taaaattttg ctggacgtca agacacgatt ggaacaggag  240
attgcaacgt atcgtcgttt gttagaaggg gaa                               273

SEQ ID NO: 24           moltype = DNA   length = 21
FEATURE                 Location/Qualifiers
source                  1..21
                        mol_type = other DNA
                        organism = synthetic construct
SEQUENCE: 24
```

```
ttccccttct aacaaacgac g                                              21

SEQ ID NO: 25           moltype = DNA   length = 66
FEATURE                 Location/Qualifiers
source                  1..66
                        mol_type = other DNA
                        organism = synthetic construct
SEQUENCE: 25
gagtcgggag cgtccggatc tagtggcgac tacaaagacg atgacgataa atcatccggt     60
agcggt                                                               66

SEQ ID NO: 26           moltype = DNA   length = 48
FEATURE                 Location/Qualifiers
source                  1..48
                        mol_type = other DNA
                        organism = synthetic construct
SEQUENCE: 26
gccactagat ccggacgctc ccgactcttc cccttctaac aaacgacg                 48

SEQ ID NO: 27           moltype = DNA   length = 28
FEATURE                 Location/Qualifiers
modified_base           28
                        mod_base = OTHER
                        note = 3' Inverted thymine
source                  1..28
                        mol_type = other DNA
                        organism = synthetic construct
SEQUENCE: 27
gagtcgactg ctaccgctac ctgatgat                                       28

SEQ ID NO: 28           moltype = DNA   length = 28
FEATURE                 Location/Qualifiers
modified_base           28
                        mod_base = OTHER
                        note = 3' Inverted thymine
source                  1..28
                        mol_type = other DNA
                        organism = synthetic construct
SEQUENCE: 28
gagtcgggag cgtccggatc tagtggct                                       28

SEQ ID NO: 29           moltype = DNA   length = 28
FEATURE                 Location/Qualifiers
source                  1..28
                        mol_type = other DNA
                        organism = synthetic construct
SEQUENCE: 29
aaaattaata cgactcacta tagggaga                                       28

SEQ ID NO: 30           moltype = DNA   length = 22
FEATURE                 Location/Qualifiers
source                  1..22
                        mol_type = other DNA
                        organism = synthetic construct
SEQUENCE: 30
tttactacta ccaccgctac tc                                             22

SEQ ID NO: 31           moltype = DNA   length = 39
FEATURE                 Location/Qualifiers
source                  1..39
                        mol_type = other DNA
                        organism = synthetic construct
SEQUENCE: 31
atcgcatatc gtcccttagt ctcctccaca cttccaatc                           39

SEQ ID NO: 32           moltype = DNA   length = 42
FEATURE                 Location/Qualifiers
source                  1..42
                        mol_type = other DNA
                        organism = synthetic construct
SEQUENCE: 32
agttttccag ggaagccttt tccatttcac aacgtaattg gg                       42

SEQ ID NO: 33           moltype = DNA   length = 50
FEATURE                 Location/Qualifiers
source                  1..50
                        mol_type = other DNA
                        organism = synthetic construct
SEQUENCE: 33
```

```
cagttgtgat tgcaattcaa tttccagcaa aattttatat tcctgattct          50

SEQ ID NO: 34          moltype = DNA  length = 38
FEATURE                Location/Qualifiers
source                 1..38
                       mol_type = other DNA
                       organism = synthetic construct
SEQUENCE: 34
gctaccgcta ccggatgaaa tctcctgttc caatcgtg                       38

SEQ ID NO: 35          moltype = DNA  length = 37
FEATURE                Location/Qualifiers
source                 1..37
                       mol_type = other DNA
                       organism = synthetic construct
SEQUENCE: 35
gccactagat ccggacgaac aaacgacgat acgttgc                        37
```

TARGET BINDING MOIETY COMPOSITIONS AND METHODS OF USE

CROSS-REFERENCE

This application is a continuation of U.S. patent application Ser. No. 17/031,260, filed Sep. 24, 2020, which is a continuation of International Patent Application No. PCT/US2019/023820, filed Mar. 25, 2019, which claims the benefit of U.S. Provisional Patent Application No. 62/648,218, filed Mar. 26, 2018, and U.S. Provisional Patent Application No. 62/686,858, filed Jun. 19, 2018, each of which is entirely incorporated herein by reference.

REFERENCE TO A SEQUENCE LISTING XML

The instant application contains a Sequence Listing which has been submitted electronically in XML format and is hereby incorporated by reference in its entirety. Said XML file, created on Dec. 14, 2022, is named 53563-702_302_SL.xml and is 41,031 bytes in size.

BACKGROUND OF THE INVENTION

Methods have been developed to interrogate the repertoire of antibodies. These methods fall into two main categories: (1) sequencing the coding region of the antibodies of interest and (2) using a large library of molecules (e.g., peptides) to examine which of these molecules can be bound by the antibodies of interest. These two categories are referred to as the "Sequencing Approach" and the "Binding Approach" herein, respectively.

With the help of NextGen Sequencing, the Sequencing Approach may be relatively easy to carry out but yields little insight into what the antibodies of interest may bind to.

The Binding Approach can include protein and peptide arrays. Cloning and expression of the different regions of target genes and purifying the recombinant truncated proteins may be the conventional method to map the antigen epitopes. However, this process can be time-consuming and some recombinant proteins can be difficult to purify. Printing synthetic peptides on a solid support to prepare a peptide array may have low sensitivity due to low binding affinity and can have a low library size. Therefore, the success of the Binding Approach can be limited in part because it can be challenging to prepare a library of molecules (e.g., peptides) that is large enough and/or with a high sensitivity.

SUMMARY OF THE INVENTION

Recognized herein is a need to generate a library of target-binding molecules (e.g., peptides for binding with an antibody) having a large library size and/or a high sensitivity. According to an aspect of the present disclosure, provided herein is a composition comprising a polynucleotide-barcoded target binding moiety, wherein the polynucleotide-barcoded target binding moiety comprises (a) a nucleic acid sequence linked by a linker to (b) a target binding unit comprising (i) a first peptide sequence comprising a first binding region, and (ii) a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody; wherein the nucleic acid sequence encodes the first peptide sequence and/or the second peptide sequence; and wherein the composition is soluble.

According to another aspect of the present disclosure, provided herein is a composition comprising a plurality of polynucleotide-barcoded target binding moieties, each polynucleotide-barcoded target binding moiety of the plurality comprising (a) a nucleic acid sequence linked by a linker to (b) a target binding unit comprising (i) a first peptide sequence comprising a first binding region, and (ii) a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody; wherein the nucleic acid sequence of each polynucleotide-barcoded target binding moiety of the plurality is unique; and wherein the composition is soluble.

In some embodiments, the single molecule comprises a first antigen binding domain and a second antigen binding domain; wherein the first binding region and the second binding region are spaced at a distance such that the first binding region binds to the first antigen binding domain and the second binding region binds to the second antigen binding domain. In some embodiments, the first binding region and second binding region have a same sequence. In some embodiments, the first binding region and second binding region have a same structure recognized by the single molecule. In some embodiments, the nucleic acid sequence of each polynucleotide-barcoded target binding moiety of the plurality comprises a unique barcode sequence. In some embodiments, the nucleic acid sequence further comprises a barcode. In some embodiments, the nucleic acid sequence is single stranded. In some embodiments, the nucleic acid sequence is double stranded. In some embodiments, the nucleic acid sequence is a deoxyribonucleic acid (DNA). In some embodiments, the nucleic acid sequence is a ribonucleic acid (RNA). In some embodiments, the nucleic acid is hybridized to a primer. In some embodiments, the polynucleotide-barcoded target binding moiety comprises a single target binding unit. In some embodiments, the polynucleotide-barcoded target binding moiety comprises two or more target binding units. In some embodiments, the composition comprises a plurality of polynucleotide-barcoded target binding moieties. In some embodiments, each polynucleotide-barcoded target binding moiety of the plurality comprises a single target binding unit. In some embodiments, at least one polynucleotide-barcoded target binding moiety of the plurality comprises a single target binding unit. In some embodiments, two or more polynucleotide-barcoded target binding moieties of the plurality comprise a single target binding unit. In some embodiments, each polynucleotide-barcoded target binding moiety of the plurality comprises two or more target binding units. In some embodiments, at least one polynucleotide-barcoded target binding moiety of the plurality comprises two or more target binding units. In some embodiments, two or more polynucleotide-barcoded target binding moieties of the plurality comprise two or more target binding units. In some embodiments, the plurality of polynucleotide-barcoded target binding moieties comprises at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1 \times 10^6$, or more polynucleotide-barcoded target binding moieties. In some embodiments, the composition comprises two or more target binding units. In some embodiments, the composition comprises from 2 to 1000 target binding units. In some embodiments, the composition comprises three or more target binding units. In some embodiments, the spacer is a polymer. In some embodiments, the spacer is a polyethylene glycol. In some embodiments, the spacer comprises a same amino acid sequence. In some embodiments, the spacer comprises a folded polypeptide, a secondary structure and/or a tertiary structure. In some embodiments, the spacer comprises a coiled coil structure or a beta sheet structure. In some embodiments, the spacer comprises two or more separate peptide chains, wherein at least one of the two or more separate peptide chains comprise an alpha-helix or a beta-strand. In some embodiments, the spacer comprises a single peptide chain folded into at least two alpha-helices or at least two beta-strands. In some embodiments, the single peptide chain comprises four alpha-helices or four beta-strands. In some embodiments, the spacer comprises a first peptide chain, a second peptide chain, and a third peptide chain, wherein the second peptide chain interacts with a first portion of the first peptide chain, and wherein the third peptide chain interacts with a second portion of the first peptide chain. In some embodiments, the first peptide chain, the second peptide chain, and/or the third peptide chain folds into an alpha-helix. In some embodiments, the second peptide chain and the third chain are linked to opposite ends of a double-stranded polynucleotide. In some embodiments, the spacer comprises an oligonucleotide. In some embodiments, the oligonucleotide is a double-stranded oligonucleotide. In some embodiments, the oligonucleotide comprises from 20 to 40 nucleotides or base pairs.

In some embodiments, the first binding region and the second binding region comprise a same epitope. In some embodiments, the first peptide sequence has a sequence that is at least about 70%, at least about 75%, at least about 80%, at least about 85%, at least about 90%, at least about 95%, at least about 98%, at least about 99%, or 100% identical to a sequence of the second peptide sequence. In some embodiments, the nucleic acid sequence is a double-stranded DNA-RNA hybrid. In some embodiments, the linker comprises a puromycin or a derivative thereof. In some embodiments, the polynucleotide-barcoded target binding moiety is a linear polymer chain or a branched polymer chain. In some embodiments, the first peptide sequence, the second peptide sequence, and the spacer are contiguous in a single polypeptide chain. In some embodiments, the first peptide sequence and the second peptide sequence are linked to the spacer through a non-peptide bond. In some embodiments, the antigen binding domain is a scFv, a Fab, or a F(ab)2. In some embodiments, the first peptide sequence and the second peptide sequence are at least 5 amino acid residues in length. In some embodiments, the polynucleotide-barcoded target binding moiety or each polynucleotide-barcoded target binding moiety of the plurality is within a vessel. In some embodiments, each polynucleotide-barcoded target binding moiety of the plurality is within a different vessel of a plurality of vessels. In some embodiments, the vessel is a droplet. In some embodiments, the droplet is a water-in-oil droplet. In some embodiments, the antibody is a biomarker.

According to another aspect of the present disclosure, provided herein is a solid support comprising a plurality of discrete regions wherein each discrete regions of the plurality comprises a target binding moiety attached thereto by a linker, wherein the target binding moiety comprises (a) a first peptide sequence comprising a first binding region, and (b) a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody. In some embodiments, the plurality of discrete regions comprise at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about $10^3$, at least about $10^4$, at least about $10^5$, or at least about $10^6$ discrete regions. In some embodiments, the target binding moiety comprises a first reaction group. In some embodiments, the solid support comprises a second reaction group attached thereto. In some embodiments, the linker is produced by reacting the first reactive group with the second reactive group. In some embodiments, the spacer comprises a polymer chain. In some embodiments, the polymer chain comprises a polynucleotide, a polypeptide, or a polyethylene glycol. In some embodiments, the polynucleotide is a double-stranded DNA, a double-stranded RNA, or a double-stranded DNA-RNA hybrid. In some embodiments, the polypeptide comprises a folded polypeptide, a secondary structure and/or a tertiary structure. In some embodiments, the spacer comprises a coiled coil structure or a beta sheet structure. In some embodiments, the spacer comprises two or more separate peptide chains, wherein at least one of the two or more separate peptide chains comprise an alpha-helix or a beta-strand. In some embodiments, the spacer comprises a single peptide chain folded into at least two alpha-helices or at least two beta-strands. In some embodiments, the single peptide chain comprises four alpha-helices or four beta-strands. In some embodiments, the spacer comprises a first peptide chain, a second peptide chain, and a third peptide chain, wherein the second peptide chain interacts with a first portion of the first peptide chain, and wherein the third peptide chain interacts with a second portion of the first peptide chain. In some embodiments, the first peptide chain, the second peptide chain, and/or the third peptide chain folds into an alpha-helix. In some embodiments, the second peptide chain and the third chain are linked to opposite ends of a double-stranded polynucleotide. In some embodiments, the single molecule comprises a first antigen binding domain and a second antigen binding domain; wherein the first binding region and the second binding region are spaced at a distance such that the first binding region binds to the first antigen binding domain and the second binding region binds to the second antigen binding domain. In some embodiments, the first binding region and second binding region have a same sequence. In some embodiments, the first binding region and second binding region have a same structure recognized by the single molecule. In some embodiments, the antigen binding domain is a scFv, a Fab, or a F(ab)2. In some embodiments, the first peptide sequence has a sequence that is at least 70%, at least 75%, at least 80%, at least 85%, at least 90%, at least 95%, at least 98%, or at least 99%, or 100% identical to a sequence of the second peptide sequence. In some embodiments, the target binding moiety comprises two or more peptide sequences, each of the two or more peptide sequences comprising a binding region.

Also provided herein is a method of manufacturing a target binding moiety by RNA display. Also provided herein is a method of manufacturing a target binding moiety by in vitro compartmentalization. Also provided herein is a method of using a target binding moiety. Also provided herein is a method of using a target binding moiety in profiling a mixture of antibodies. Also provided herein is a method of using a target binding moiety in diagnosing a disease. In some embodiments, the disease is a cancer or an autoimmune disease.

According to another aspect of the present disclosure, provided herein is a method comprising translating an RNA sequence of an RNA, wherein the RNA sequence encodes a peptide sequence, wherein the RNA is linked to a peptide acceptor at a 3' end of the RNA, linking the peptide acceptor to an amino acid residue of a translated peptide comprising the peptide sequence, thereby forming a nucleic acid-peptide fusion molecule, wherein the nucleic acid-peptide fusion molecule comprises a polynucleotide barcoded target binding moiety comprising: (a) a first peptide sequence comprising a first binding region, and (b) a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody. In some embodiments, the method further comprises providing a DNA, wherein the DNA encodes the RNA. In some embodiments, the method further comprises transcribing the DNA. In some embodiments, the method further comprises reverse transcribing the RNA. In some embodiments, the DNA molecule and/or the RNA sequence encodes the first peptide sequence, the second peptide sequence and the spacer. In some embodiments, the nucleic acid-peptide fusion molecule comprises a plurality of nucleic acid-peptide fusion molecules. In some embodiments, each nucleic acid-peptide fusion molecule of the plurality comprises a unique nucleic acid sequence. In some embodiments, the first binding region and second binding region have a same sequence. In some embodiments, the first binding region and second binding region have a same structure recognized by the single molecule. In some embodiments, the spacer of each nucleic acid-peptide fusion molecule is the same or comprises a same amino acid sequence. In some embodiments, the spacer comprises a folded polypeptide, a secondary structure and/or a tertiary structure. In some embodiments, the spacer comprises a coiled coil structure or a beta sheet structure. In some embodiments, the first peptide sequence has a sequence that is at least about 70%, at least about 75%, at least about 80%, at least about 85%, at least about 90%, at least about 95%, at least about 98%, at least about 99%, or 100% identical to a sequence of the second peptide sequence. In some embodiments, antigen binding domain is a scFv, a Fab, or a F(ab)2. In some embodiments, the first peptide sequence and the second peptide sequence are from 4 to 30 amino acids, from 5 to 20 amino acids, from 6 to 10 amino acids, from 8 to 11 amino acids, or from 10 to 20 amino acids in length. In some embodiments, the translating comprises in vitro translating.

According to another aspect of the present disclosure, provided herein is a method comprising expressing a first peptide sequence encoded by a nucleic acid and a second peptide sequence encoded by a nucleic acid in each vessel of a plurality of vessels, wherein each vessel of the plurality comprises a scaffold comprising a first linking site and a second linking site separated by a spacer; and binding the first peptide sequence to the first linking site and the second peptide sequence to the second linking site, wherein the first peptide sequence bound to the first linking site and the second peptide sequence bound to the second linking site are spaced at a distance such that the first peptide sequence and the second peptide sequence simultaneously bind to a single molecule comprising an antigen binding domain of an antibody, thereby forming a plurality of target binding moieties. In some embodiments, the nucleic acid is linked to the scaffold by a linker. In some embodiments, a 5' end or a 3' end of the nucleic acid is linked to the scaffold by the linker. In some embodiments, the nucleic acid is a single nucleic acid molecule. In some embodiments, the nucleic acid is linked to the scaffold before or after generating the plurality of vessels. In some embodiments, the nucleic acid molecule is double-stranded or single-stranded. In some embodiments, the nucleic acid molecule is a DNA, a RNA, or a combination thereof. In some embodiments, expressing comprises transcribing and/or translating. In some embodiments, the first peptide sequence and the second peptide sequence comprise a same sequence. In some embodiments, the first peptide sequence has a sequence that is at least 70%, at least 75%, at least 80%, at least 85%, at least 90%, at least 95%, at least 98%, or at least 99%, or 100% identical to a sequence of the second peptide sequence. In some embodiments, the method further comprises pooling a plurality of polynucleotide-barcoded target binding moieties from the vessels. In some embodiments, the vessels are droplets. In some embodiments, the droplets are water-in-oil droplets. In some embodiments, the further comprises barcoding the target binding moieties of the plurality. In some embodiments, barcoding comprises attaching barcodes to the target binding moieties. In some embodiments, the scaffold is attached to a barcoded polynucleotide before expressing. In some embodiments, the scaffold is attached to the nucleic acid encoding the first peptide sequence and/or the nucleic acid encoding the second peptide sequence. In some embodiments, the scaffold is attached to the nucleic acid encoding the first peptide sequence and/or the nucleic acid encoding the second peptide sequence before expressing.

According to another aspect of the present disclosure, provided herein is a method comprising: contacting a mixture of antibodies with a population of target binding moieties, wherein each target binding moiety of the population comprises a target binding unit having a first binding region and a second binding region, wherein the first binding region and the second binding region are separated by a spacer and spaced at a distance such that the first binding region and the second binding region simultaneously bind to a single antibody molecule of the mixture. In some embodiments, the target binding unit further comprises a first peptide and/or peptoid sequence having the first binding region and a second peptide and/or peptoid sequence having the second binding region. In some embodiments, the first binding region and the second binding region have a same sequence. In some embodiments, the first binding region and the second binding region have a same structure that recognized by the single molecule. In some embodiments, the population of target binding moieties is provided on a solid support. In some embodiments, the population of target binding moieties is immobilized on the solid support. In some embodiments, the solid support has at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about $10^3$, at least about $10^4$, at least about $10^5$, or at least about $10^6$ discrete regions. In some embodiments, each of the discrete regions has a different target binding moieties from the population immobilized thereon. In some embodiments, the different target binding moieties from the population comprises a same binding region. In some embodiments, the different target binding moieties from the population comprises a same peptide and/or peptoid sequence. In some embodiments, each of the discrete regions has two or more copies of the different target binding moieties. In some embodiments, the method further comprises removing unbound antibodies of the mixture. In some embodiments, the method further comprises quantifying an amount of antibodies bound at each of the discrete regions. In some embodiments, the quantifying comprises detecting a fluorescent signal, an electrochemical signal, a chemiluminescent signal, a chromogenic signal, or a combination thereof. In some embodiments, the method further comprises obtaining a blood sample from a subject. In some embodiments, the method further comprises preparing a serum sample from the blood sample, wherein the serum sample comprises the mixture of antibodies. In some embodiments, the subject comprises a diseased subject and/or a healthy subject. In some embodiments, the method further comprises obtaining a first serum sample from the diseased subject and a second serum sample from the healthy subject, wherein the quantifying comprises quantifying an amount of antibodies bound at each of the discrete regions in the first serum sample on a first solid support and the second serum sample on a second solid support. In some embodiments, the method further comprises comparing the amount of antibodies bound at each of the discrete regions on the first solid support and the amount of antibodies bound at each of the discrete regions on the second solid support. In some embodiments, the method further comprises selecting a panel of peptides of the discrete regions having a difference in the amount of antibodies bound on the first solid support and the second solid support. In some embodiments, the population of target binding moieties is provided in solution. In some embodiments, each of the population of target binding moieties is linked to a coding moiety. In some embodiments, the coding moiety is a polynucleotide. In some embodiments, the polynucleotide is a deoxyribonucleic acid (DNA), a ribonucleic acid (RNA), or a combination thereof. In some embodiments, the polynucleotide is a single-stranded DNA, a single-stranded RNA, a double-stranded DNA, a double-stranded RNA, or a double-stranded DNA-RNA hybrid. In some embodiments, the coding moiety comprises a nucleic acid sequence that identifies a sequence of the target binding moiety. In some embodiments, the nucleic acid sequence encodes a peptide sequence of the two or more target binding moiety. In some embodiments, the population of target binding moieties comprises at least about 100, at least about $10^3$, at least about $10^4$, at least about $10^5$, or at least about $10^6$ different types of target binding moieties. In some embodiments, each type of target binding moieties from the population comprises a same peptide and/or peptoid sequence. In some embodiments, the coding moiety is unique to each type of target binding moieties of the population. In some embodiments, the method further comprises capturing, or enriching, or isolating an antibody-bound fraction of target binding moieties of the population. In some embodiments, the method further comprises amplifying a coding moiety of the antibody-bound fraction of target binding moieties. In some embodiments, the method further comprises quantifying the coding moiety or a copy of the coding moiety of the antibody-bound fraction. In some embodiments, quantifying comprises sequencing the coding moiety or a copy of the coding moiety of the antibody-bound fraction of target binding moieties. In some embodiments, the method further comprises obtaining a blood sample from a subject. In some embodiments, the method further comprises preparing a serum sample from the blood sample, wherein the serum sample comprises the mixture of antibodies. In some embodiments, the subject comprises a diseased subject and/or a healthy subject. In some embodiments, the method further comprises obtaining a first serum sample from the diseased subject and a second serum sample from the healthy subject, wherein the quantifying comprises quantifying an amount of the antibody-bound fraction of target binding moieties in the first serum sample and an amount of the antibody-bound fraction of target binding moieties in the second serum sample. In some embodiments, the method further comprises comparing the amount of the antibody-bound fraction of target binding moieties in the first serum sample and the amount of the antibody-bound fraction in the second serum sample. In some embodiments, the method further comprises selecting a panel of peptides, wherein each peptide of the panel has a difference in the amount of antibody-bound fraction of target binding moieties in the first serum sample and the second serum sample. In some embodiments, each peptide of the panel is identified abundantly in the first serum sample but not in the second serum sample, or is identified abundantly in the second serum sample but not in the first serum sample. In some embodiments, the method further comprises making the population of target binding moieties each linked to the coding moiety by RNA display. In some embodiments, each of the population of target binding moieties further comprises a puromycin moiety or a variant thereof. In some embodiments, the first peptide and/or peptoid sequence has a sequence that is at least about 70%, at least about 75%, at least about 80%, at least about 85%, at least about 90%, at least about 95%, at least about 98%, at least about 99%, or 100% identical to a sequence of the second peptide and/or peptoid sequence. In some embodiments, the first peptide sequence, the second peptide sequence, and the spacer are linked by a peptide bond. In some embodiments, the first peptide and/or peptoid sequence, the second peptide and/or peptoid sequence, and the spacer are linked by a non-peptide bond. In some embodiments, the target binding moiety comprises two or more target binding units. In some embodiments, the first peptide and/or peptoid sequence, or the second peptide and/or peptoid sequence is at least 5 residues in length. In some embodiments, the spacer comprises a polymer. In some embodiments, the spacer comprises a pre-designed amino acid sequence. In some embodiments, the spacer is a polypeptide, a polynucleotide, or a polyethylene glycol. In some embodiments, the spacer comprises a folded polypeptide, a secondary structure, and/or a tertiary structure. In some embodiments, the folded polypeptide comprises a coiled coil structure or a beta sheet. In some embodiments, the coiled coil structure is formed by two separate peptide strands, wherein each of the two separate peptide strands folds into an alpha-helix. In some embodiments, the coiled coil structure is formed by a single peptide strand comprising at least two regions folded into alpha-helices. In some embodiments, the single peptide strand comprises four regions folded into alpha-helices. In some embodiments, the coiled coil structure is formed by a first peptide strand, a second peptide strand, and a third peptide strand, wherein the second peptide strand interacts with a first portion of the first peptide strand, and the third peptide strand interacts with a second portion of the first peptide strand. In some embodiments, the second peptide strand and the third peptide strand are linked to opposite ends of a double-stranded polynucleotide. In some embodiments, the spacer comprises a double-stranded deoxyribonucleic acid. In some embodiments, the mixture of antibodies is a mixture of monoclonal antibodies, a mixture of polyclonal antibodies, or a combination thereof. In some embodiments, the mixture of antibodies comprises a biomarker.

According to another aspect of the present disclosure, provided herein is a method for selecting a panel of peptides, comprising: (a) providing two or more copies of an array comprising a first array and a second array (b) obtaining a first mixture of antibodies from a diseased subject and a second mixture of antibodies from a healthy subject; (c) contacting the first mixture with the first array and the second mixture with the second array, wherein each array has at least 104 discrete regions, wherein each of the discrete regions has a unique type of target binding moieties having a first target binding region and a second target binding region, wherein the first binding region and the second binding region are separated by a spacer and spaced at a distance such that the first binding region and the second binding region simultaneously bind to a single antibody molecule of the mixture; (d) removing an unbound fraction of antibodies on both the first and the second array; (e) quantifying an amount of bound antibodies on each of the discrete regions on the first array and the second array; and (f) identifying peptides of the second array not bound by an antibody on the first array.

According to another aspect of the present disclosure, provided herein is a method for selecting a panel of peptides, comprising: (a) providing a first solution and a second solution; (b) obtaining a first mixture of antibodies from a diseased subject and a second mixture of antibodies from a healthy subject; (c) contacting the first mixture with the first solution and the second mixture with the second solution, wherein each of the first and the second solution comprises a plurality of polynucleotide-barcoded target binding moieties, wherein each polynucleotide-barcoded target binding moiety of the plurality comprising a nucleic acid sequence linked by a linker to a target binding unit comprising a first peptide sequence comprising a first binding region, and a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody; (d) capturing antibody-bound compositions of the population in the first solution and the second solution; (e) sequencing coding moieties captured from the first solution and the second solution; and (0 selecting the panel of peptides.

According to another aspect of the present disclosure, provided herein is a method for profiling a mixture of antibodies from a subject, comprising: contacting the mixture of antibodies with an array having at least 10 discrete regions, wherein each of the discrete regions has a unique type of target binding moieties, wherein each of the unique type of target binding moieties comprises a first binding region and a second binding region, wherein the first binding region and the second binding region are separated by a spacer and spaced at a distance such that the first binding region and the second binding region simultaneously bind to a single antibody molecule of the mixture. In some embodiments, the method further comprises removing an unbound fraction of antibodies of the mixture. In some embodiments, the method further comprises detecting a bound fraction antibodies of the mixture on the array, wherein a signal is observed at each of the discrete regions having antibodies bound thereon, thereby generating a signal pattern on the array. In some embodiments, the method further comprises identifying a disease of the subject. In some embodiments, the disease is an auto-immune disease, a cancer, or an infectious disease. In some embodiments, each of the unique type of target binding moieties further comprises a first peptide and/or peptoid sequence having the first binding region and a second peptide and/or peptoid sequence having the second binding region. In some embodiments, the first binding region and the second binding region have a same sequence. In some embodiments, the first binding region and the second binding region have a same structure that recognized by the single molecule. In some embodiments, the first peptide and/or peptoid sequence has a sequence that is at least 70%, at least 75%, at least 80%, at least 85%, at least 90%, at least 95%, at least 98%, or at least 99%, or 100% identical to a sequence of the second peptide and/or peptoid sequence. In some embodiments, the first peptide sequence, the second peptide sequence, and the spacer are linked by a peptide bond. In some embodiments, the first peptide and/or peptoid sequence, the second peptide and/or peptoid sequence, and the spacer are linked by a non-peptide bond. In some embodiments, the target binding moiety comprises two or more binding regions. In some embodiments, the first peptide and/or peptoid sequence, or the second peptide and/or peptoid sequence is at least 5 residues in length. In some embodiments, the spacer comprises a polymer. In some embodiments, the spacer comprises a same amino acid sequence. In some embodiments, the spacer is a polypeptide, a polynucleotide, or a polyethylene glycol. In some embodiments, the spacer comprises a folded polypeptide, a secondary structure, and/or a tertiary structure. In some embodiments, the folded polypeptide comprises a coiled coil structure or a beta sheet. In some embodiments, the coiled coil structure is formed by two separate peptide strands, wherein each of the two separate peptide strands folds into an alpha-helix. In some embodiments, the coiled coil structure is formed by a single peptide strand comprising at least two regions folded into alpha-helices. In some embodiments, the single peptide strand comprises four regions folded into alpha-helices. In some embodiments, the coiled coil structure is formed by a first peptide strand, a second peptide strand, and a third peptide strand, wherein the second peptide strand interacts with a first portion of the first peptide strand, and the third peptide strand interacts with a second portion of the first peptide strand. In some embodiments, the second peptide strand and the third peptide strand are linked to opposite ends of a double-stranded polynucleotide. In some embodiments, the spacer comprises a double-stranded deoxyribonucleic acid. In some embodiments, the mixture of antibodies is a mixture of monoclonal antibodies, a mixture of polyclonal antibodies, or a combination thereof. In some embodiments, the mixture of antibodies comprises a biomarker.

According to another aspect of the present disclosure, provided herein is a plurality of nucleic acid molecules, wherein each nucleic acid molecule of the plurality encodes a polypeptide target binding moiety, which peptide target binding moiety comprises: (i) a first peptide sequence comprising a first binding region, and (ii) a second peptide sequence comprising a second binding region; wherein the first binding region and the second binding region are (i) separated by a spacer, and (ii) spaced at a distance such that the first peptide sequence and the second peptide sequence simultaneously bind to a single molecule; wherein the plurality of nucleic acid molecules comprises at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, or at least about $10^{15}$ unique sequences. In some embodiments, the single molecule comprises an antigen binding domain. In some embodiments, the plurality of nucleic acid molecules is a plurality of double-stranded DNA molecules. In some embodiments, the plurality of nucleic acid molecules is a plurality of single-stranded RNA molecules. In some embodiments, each nucleic acid molecule of the plurality is a circular molecule. Also provided herein is a method of making a library of polynucleotide-peptide fusion molecules using the library of nucleic acid molecules described herein. The method comprises: providing a plurality of nucleic acid molecules and expressing the plurality of nucleic acid molecules to generate a plurality of peptides in an RNA display assay, wherein each nucleic acid molecule is linked to a peptide expressed from said nucleic acid molecule via a linker. In some embodiments, said linker comprises a puromycin or a derivative thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
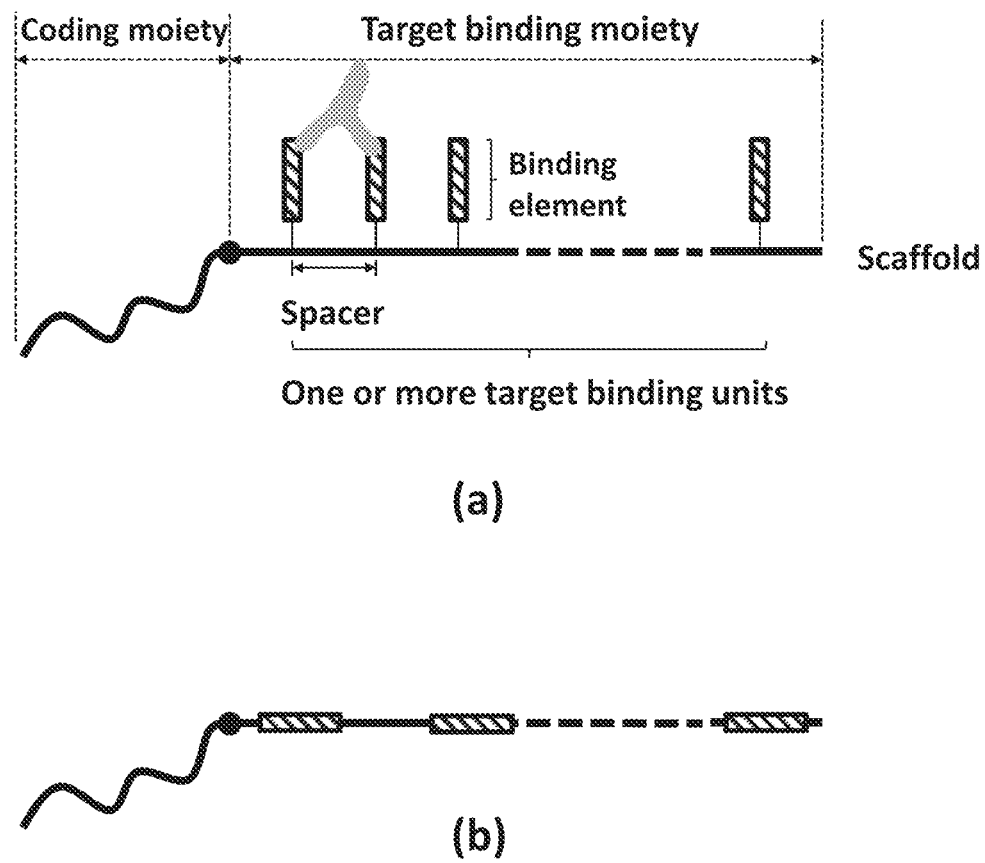
FIG. 1 illustrates two example structures of target binding moieties or target binding moieties linked with coding moieties described herein.

In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

Overview

Determining the specific antigen binding regions or epitopes of an antibody may benefit not only antibody based testing platforms, but also their therapeutic applications, development of vaccines, study of protein interactions, auto-immune diseases, etc. Methods to interrogate the repertoire of antibodies can comprise (1) sequencing the coding region of the antibodies of interest, (2) using a large library or molecules (e.g., peptides, peptoids, or proteins, which are collectively called potential immunoreceptor-binding molecules, or PIRMs, in this present disclosure) to examine which of these molecules can be bound by the targets of interest (e.g., antibodies of interest). To overcome the problems associated with the methods known in the art, the compositions and methods provided herein can be used to generate a library of PIRMs having a large library size and/or a high sensitivity. For example, the methods provided herein can generate a library of FIRM comprising at least about 100, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, or at least about $10^{20}$ different species (e.g., unique sequences).

Provided herein are compositions and methods for screening/identifying binding elements that analytes bind. For examples, provided herein are compositions and methods for screening/identifying peptides or peptoid sequences that antibodies bind. The compositions and methods disclosed herein offer several advantages over traditional peptide arrays, including high library size and high sensitivity. The identified peptide sequences can subsequently be used to manufacture an array with a library of addressable peptide sequences for antibody profiling in a given sample. In various embodiments disclosed herein, two peptides are provided in a pair as one target binding unit, wherein the two peptides are spaced at a distance such that they can bind to a single molecule simultaneously.

In one aspect, provided herein are compositions comprising a target binding unit, wherein the target binding unit comprises two binding elements separated by a spacer, wherein the two binding elements bind to a single molecule having an antigen binding domain of an antibody simultaneously. In various embodiments, the binding elements are peptide sequences or peptoid sequences. The two peptides of a target binding unit are separated by the spacer so that they are positioned to bind to the two antigen binding domains (e.g., Fab) of an antibody simultaneously. The methods provided herein take advantage of the two antigen binding domains of an antibody and can improve the binding affinity by at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold. In some embodiments, the two peptides of the target binding unit have a same sequence. Also provided herein are compositions comprising a target binding moiety, wherein the target binding moiety comprises one or more target binding units. The one or more target binding units in each target binding moiety can be linked. A target binding moiety comprises two or more binding elements (e.g., peptide sequences or peptoids sequences). In some embodiments, a target binding moiety comprises a first peptide sequence and a second peptide sequence, wherein the first peptide sequence and the second peptide sequence are separated by a spacer so that they can bind to a single antibody molecule simultaneously. In some embodiments, the two or more peptide sequences of the target binding moiety have a same sequence.

In another aspect, provided herein are methods of using the target binding unit or target binding moiety to screen and identify peptide or peptoid sequences that bind to antibodies in a patient sample and antibodies in a healthy sample with a difference. For example, in the peptide screening and identification methods, a plurality of target binding units will be provided, wherein each of the target binding unit comprises two peptides having a same sequence or binding region (e.g., an epitope). In some cases, compositions comprising a target binding unit are provided in solution. In such cases, the target binding unit or the target binding moiety can be further linked to a coding moiety. In some applications, the coding moiety serves as a barcode that corresponds to or identifies the peptide or peptoid sequence of the target binding unit. In some other applications, the coding moiety comprises a sequence that can both encode the peptides of the target binding unit and serve as a barcode to identify the peptide sequence. The coding moiety enables identification of peptide sequences through high-throughput sequencing. In some cases, compositions comprising a target binding unit or a target binding moiety are provided on a solid surface. In such cases, the target binding unit or the target binding moiety having a unique binding element (e.g., a peptide sequence) will be immobilized on a discrete region of the solid surface separated from another target binding unit having a different binding element. Therefore, a coding moiety may not be needed when the target binding unit is provided on a solid surface.

In another aspect, provided herein are methods of using the identified peptide or peptoid sequences to profile antibodies in a sample from a subject, which can be used to infer whether the subject has a disease. Because the peptides or peptoids are identified by the screening/identification methods disclosed herein, the peptides or peptoids are known to be able to differentiate a patient sample from a healthy sample, and the peptides or peptoids are also linked to the disease associated with the patient sample. The identified peptides can be provided on a solid surface (e.g., an array), a signature pattern can be generated on the solid surface when profiling antibodies in the sample. In some cases, the signature pattern may be similar to the patient sample, indicating the subject is likely to have a disease. In some other cases, the signature pattern may be similar to the healthy sample, indicating the subject is healthy. As disclosed herein, the peptide sequences on the solid surface are provided as target binding units, wherein each target binding unit comprises two peptides having a same sequence or epitope, wherein the two peptides are spaced by a spacer.

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide," "nucleic acid," and "oligonucleotide" are used interchangeably. They can refer to a polymeric form of nucleotides of various lengths, either deoxyribonucleotides or ribonucleotides, or analogs thereof. A polynucleotide may include one or more nucleotides selected from adenosine (A), cytosine (C), guanine (G), thymine (T) and uracil (U), or variants thereof. A polynucleotide provided herein can be double-stranded or single-stranded. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), circular RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. In some cases, a polynucleotide provided herein is a coding moiety what can be used to indicate the identity of another moiety. In some other cases, a polynucleotide provided herein is a spacer which can be used to link two entities.

Polynucleotides may include one or more nucleotide variants, including nonstandard nucleotide(s), non-natural nucleotide(s), nucleotide analog(s), and/or modified nucleotides. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Polynucleotides can be modified at one or more positions to enhance stability introduced during chemical synthesis or subsequent enzymatic modification or polymerase copying. These modifications include, but are not limited to, the inclusion of one or more alkylated nucleic acids, locked nucleic acids (LNAs), peptide nucleic acids (PNAs), phosphonates, phosphothioates, and the like in the oligomer Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine and the like. Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes.

As used herein, the term "polypeptide" is two or more amino acids joined together through peptide bonds (or amide bonds) and is alternatively referred to as a "peptide". A peptide bond, also known as an amide bond, is a covalent chemical bond linking two consecutive amino acid monomers along a peptide or protein chain. In the context of this specification it should be appreciated that the amino acids may be the L-optical isomer or the D-optical isomer. The amino acids can be non-naturally encoded amino acids. A peptide can comprise one or more non-naturally encoded amino acid. A "non-naturally encoded amino acid" refers to an amino acid that is not one of the common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g., post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine. Peptides are two or more amino acid monomers long, and often can be more than 20 amino acid monomers long. A polypeptide can be linearly unstructured or folded in three-dimensional structure. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. A structured polypeptide can be a protein. As used herein, "protein" refers to a long polymer of amino acid residues linked via peptide bonds and which may be composed of one or more polypeptide chains. More specifically, the term "protein" refers to a molecule composed of one or more amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, antibodies, and any fragments thereof. A protein can be a portion of the protein, for example, a domain, a subdomain, or a motif of the protein. A protein can be a variant (or mutation) of the protein, wherein one or more amino acid residues are inserted into, deleted from, and/or substituted into the naturally occurring (or at least a known) amino acid sequence of the protein. A protein can be a modified protein. Non-limiting examples of protein modification include phosphorylation, acetylation, glycosylation, amidation, hydroxylation, methylation, alkylation, acylation, ubiquitylation, pyrrolidone carboxylic acid, and sulfation. A protein or a variant thereof can be naturally occurring or recombinant.

As used herein, the term "peptoids", also referred as poly-N-substituted glycines, are a class of peptidomimetics whose side chains are appended to the nitrogen atom of the peptide backbone, rather than to the α-carbons (as they are in amino acids). In peptoids, the side chain is connected to the nitrogen of the peptide backbone, instead of the α-carbon as in peptides. Notably, peptoids lack the amide hydrogen which is responsible for many of the secondary structure elements in peptides and proteins. Peptoids can be used to mimic protein/peptide products to aid in the discovery of protease-stable small molecule drugs. In synthesizing peptoids, each residue can be installed in two steps in an approach called submonomer approach: acylation and displacement. In the acylation step a haloacetic acid, typically bromoacetic acid activated by diisopropylcarbodiimide reacts with the amine of the previous residue. In the displacement step (a classical $SN_2$ reaction), an amine displaces the halide to form the N-substituted glycine residue. The submonomer approach allows the use of any commercially available or synthetically accessible amine for combinatorial chemistry. Peptoids are generally resistant to proteolysis, and are therefore advantageous for therapeutic applications where proteolysis is a major issue. Since secondary structure in peptoids generally does not involve hydrogen bonding, it is not typically denatured by solvent, temperature, or chemical denaturants such as urea. Peptoid oligomers can be conformationally unstable, due to the flexibility of the main-chain methylene groups and the absence of stabilizing hydrogen bond interactions along the backbone. Nevertheless, through the choice of appropriate side chains it is possible to form specific steric or electronic interactions that favor the formation of stable secondary structures like helices, especially peptoids with C-α-branched side chains are known to adopt structure analogous to polyproline I helix. Different methods can be employed to predict and characterize peptoid secondary structure, with the ultimate goal of developing fully folded peptoid protein structures. The cis/trans amide bond isomerization can lead to a conformational heterogeneity which may not allow for the formation of homogeneous peptoid foldamers. Nonetheless trans-inducer N-Aryl side chains promoting polyproline type II helix, and strong cis-inducer such as bulky naphthylethyl and tert-butyl side chains have been found. In various embodiments provided herein, the peptide sequence of the target binding unit can be replaced by a peptoid sequence.

The term "coiled coil" or "coiled coil structure" refers to a structural motif in which a plurality of alpha-helices are coiled together like the strands of a rope (e.g., dimers and trimers are examples of common types). For example, a leucine zipper is a coiled coil structure.

The terms "functional group", "active moiety", "activating group", "leaving group", "reactive site", "reactive group", "chemically reactive group" and "chemically reactive moiety" refer to distinct, definable portions or units of a molecule. The terms are used herein to indicate the portions of molecules that perform some function or activity or are reactive with other molecules.

The term "linkage" or "linker" refers to groups or bonds that normally are formed as the result of a chemical reaction.

The term "spaced" or "separated" can be used interchangeably herein. When describing two peptide/peptoid sequences are spaced or separated by a spacer, it is intended to mean that the two peptides are not directly linked with each other but are linked through the spacer.

The term "sequence" and its grammatical equivalents as used herein can refer to a polypeptide sequence or a polynucleotide sequence. A polynucleotide or nucleotide sequence can be DNA or RNA; can be linear, circular or branched; and can be either single-stranded or double stranded. A sequence can be mutated. A sequence can be of any length, for example, between 2 and 1,000,000 or more amino acids or nucleotides in length (or any integer value there between or there above), e.g., between about 100 and about 10,000 nucleotides or between about 200 and about 500 amino acids or nucleotides.

"Solid support", "support", "solid phase support", "substrate" and other grammatical equivalents herein refer to any material that can be modified to contain discrete individual sites appropriate for the attachment or association of molecules and can be amenable to at least one detection method. They can be a material or group of materials having a rigid or semi-rigid surface or surfaces. The number of possible substrates can be very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In some cases, the substrates allow optical detection and may not themselves fluoresce. The substrate can be flat (planar), although other configurations of substrates may be used as well; for example, three dimensional configurations can be used, for example by embedding the target binding moieties in a porous block of plastic that allows sample access to the target binding moieties. In some embodiments, the target binding moieties can be placed on the inside surface of a tube, for flow-through sample analysis to minimize sample volume. Substrates can include optical fiber bundles, and flat planar substrates such as glass, polystyrene and other plastics and acrylics. In some embodiments, the solid support or substrate can be a multi-well plate. In some embodiments, at least one surface of the solid support can be substantially flat, although in some embodiments it may be useful to physically separate regions for different molecules or reactions with, for example, wells, raised regions, pins, etched trenches, or the like. In some embodiments, the solid support(s) can take the form of beads, resins, gels, microspheres, or other geometric configurations.

"Addressable" in reference to target binding unit or target binding moiety means that the peptide/peptoid sequence of the target binding unit or target binding moiety, or perhaps other physical or chemical characteristics, can be determined from its address, e.g., a one-to-one correspondence between the sequence or other property of the target binding unit or target binding moiety and a spatial location on, or characteristic of, the solid phase support to which it is attached.

"Array", or "microarray" refers to a solid phase support having a planar surface, which can carry an array of nucleic acids or peptides, each spatially defined region or site of the array comprising copies of an oligonucleotide or peptide immobilized to the spatially defined region or site, which does not overlap with those of other regions or sites of the array; that is, the regions or sites are spatially discrete. Spatially defined binding sites may additionally be "addressable" in that its location and the identity of its immobilized oligonucleotide or peptide are known or predetermined, for example, prior to its use. Microarrays can comprise at least one planar solid phase support, such as a glass microscope slide. In some embodiments, the oligonucleotides or peptides are covalently attached to the solid phase support. In some embodiments, oligonucleotides can be attached to the solid support by a 5'-end or a 3'-end. In some embodiments, peptides can be attached indirectly through an oligonucleotide or through an unnatural amino acid incorporated in the peptides. For reviews of microarray technology see: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). A "random microarray" refers to a microarray whose spatially discrete regions of oligonucleotides or peptides may not be spatially addressed. For example, the identity of the attached oligonucleotides or peptides may not be discernable, at least initially, from its location. In some aspects, random microarrays are planar arrays of microbeads wherein each microbead has attached a single kind of oligonucleotides or peptides. Arrays of microbeads may be formed in a variety of ways, e.g., Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides/peptides thereof, in a random array may be identified in a variety of ways, including by optical labels, e.g., fluorescent dye ratios or quantum dots, shape, sequence analysis, or the like.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label can be any composition detectable by spectroscopic, photochemical, biochemical, immunochemical, electrical, optical or chemical means.

A "sample" refers to a quantity of material from a biological, environmental, medical, or patient source in which detection or measurement of an analyte is sought. A sample may include a specimen or culture (e.g., microbiological cultures). A sample may include biological and environmental samples. A sample may include a specimen of synthetic origin. Biological samples may include materials taken from a patient or a healthy subject including, but not limited to, blood, saliva, spinal fluid, pleural fluid, milk, lymph, sputum, semen, needle aspirates, plasma, serum, the external sections of the skin, respiratory, intestinal, and genitourinary tracts, tears, cells (including but not limited to blood cells), tumors, organs, and also samples of in vitro cell culture constituents. Biological samples may be obtained from all of the various families of domestic animals, as well as feral or wild animals, including, but not limited to, such animals as ungulates, bear, fish, rodents, etc. Environmental samples may include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present disclosure.

The term "vessel" as used herein refers to a compartment (e.g., a microfluidic channel, a well, or a droplet) in which a biochemical reaction (e.g., target protein and antibody binding, nucleic acid hybridization and primer extension) may occur. The terms "vessel" and "compartment" can be used interchangeably. The volume of the compartment may be as large as 1 mL or may be as small as 1 picoLiter. In some embodiments, the median size of the compartments of a plurality of compartments is from about 1 to about 10 picoLiter, from about 10 to about 100 picoLiter, from about 100 picoLiter to about 1 nanoLiter, from about 1 to about 10 nanoLiter, from about 10 to about 100 nanoLiter, from about 100 nanoLiter to about 1 microLiter, from about 1 to about 10 microLiter, from about 10 to about 100 microLiter, or from about 100 to about 1000 microLiter. The volume of the aqueous content in the compartment can be smaller than or about equal to the volume of the compartment. In some embodiments, the median volume of the aqueous content in the compartments is 1 microLiter or less.

"Droplets" refer to compartments surrounded by liquid rather than solid. Droplets may be water-in-oil; water-in-oil-in-water, or water in a lipid layer (liposome). In some embodiments, droplets can be of uniform size or heterogeneous size. In some embodiments, the median diameter of the droplets in a plurality of droplets can range from about 0.001 μm to about 1 mm. In some embodiments, the median volume of the droplets in a plurality of droplets can range from about 0.01 nanoLiter to about 1 microLiter.

The term "epitope" refers to any protein or peptide capable of being specifically bound to an immunoglobulin or antibody. Epitopic determinants can comprise chemically active surface groupings of molecules such as amino acids or sugar side chains and can have three dimensional structural characteristics, as well as charge characteristics. An antibody may specifically bind an antigen when the dissociation constant is ≤1 μM, or ≤100 nM or ≤10 nM. As used herein, epitope can also be used to refer to a peptoid capable of being specifically bound to an immunoglobulin or antibody.

The term "partition," as used herein, may be a verb or a noun. When used as a verb (e.g., "to partition," or "partitioning"), the term generally refers to the fractionating (e.g., subdividing) a species or sample (e.g., a polynucleotide sample) between vessels that can be used to sequester one fraction (or subdivision) from another. Such vessels are referred to using the noun "partition." Partitioning may be performed, for example, using microfluidics, dilution, dispensing, vortexing, and the like. A partition may be, for example, a well, a microwell, a hole, a droplet (e.g., a droplet in an emulsion), a continuous phase of an emulsion, a test tube, a spot, a capsule, a bead, a surface of a bead in dilute solution, or any other suitable container for sequestering one fraction of a sample from another. A partition may also comprise another partition.

Percent (%) sequence identity with respect to a reference polypeptide sequence (or nucleic acid sequence) refers to the percentage of amino acid residues (or nucleotides in case of nucleic acid sequence) in a candidate sequence that are identical with the amino acid residues (or nucleotides) in the reference polypeptide sequence (or nucleic acid sequence), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Analyte

Provided herein are compositions and methods for identifying a binding element (e.g., peptide sequence or peptoid sequence) that can bind to an analyte from a sample. As used herein, the analyte can refer to a target or a target molecule. The binding element can be a peptide sequence or peptoid sequence. The analyte can be a polypeptide. The analyte can be a protein. The analyte can be an endogenous protein or an artificial protein. The analyte can be a recombinant protein. An analyte described herein can be obtained or isolated from a subject. In various embodiments, the methods provided herein comprise contacting an analyte with a target binding moiety or target binding unit described herein.

The analyte can be an antibody or an immunoglobulin. In some embodiments, the analyte is an antibody fragment. In some embodiments, the antibody or a fragment thereof described in the compositions and methods comprises two antigen-binding (Fab) fragments. In some embodiments, the two Fab fragments bind to the same antigen. In some embodiments, the antibody is a bispecific antibody. In some embodiments, the antibody is a bispecific antibody, wherein the bispecific antibody comprises two Fab fragments which bind to different antigens. In some embodiments, the antibody or a fragment thereof comprises an unconventional amino acid. In some embodiments, the antibody is a monoclonal antibody, a polyclonal antibody, or a combination thereof. In some embodiments, the analyte is a mixture of antibodies. In some embodiments, the analyte is a mixture of monoclonal antibodies. In some embodiments, the analyte is a mixture of polyclonal antibodies. In some embodiments, a mixture of antibodies comprises a monoclonal antibody and a polyclonal antibody. In some embodiments, a mixture of antibodies is contained in a blood sample. In some embodiments, a mixture of antibodies is contained in a serum sample.

In some embodiments, an analyte described herein can be a molecule that binds to an antigen binding domain of an antibody. In some embodiments, an analyte described herein can be a molecule that comprises an antigen binding domain of an antibody. The antigen binding domain can be a scFv, a Fab, or a F(ab')$_2$. Other examples of antigen binding domain include, inter alia, Fab, Fab', F(ab')$_2$, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The term "diabodies," as used herein, refers to small antibody fragments with two antigen-binding sites, which fragments comprise a heavy-chain variable domain ($V_H$) Connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

An analyte described herein can be obtained or isolated from a subject. In some applications, the analyte is obtained or isolated from a blood sample from a subject. In some applications, the analyte is obtained or isolated from a serum sample from a subject. In some applications, an antibody is obtained or isolated from a blood sample from a subject. In some applications, an antibody is obtained or isolated from a serum sample from a subject.

In some embodiments, the methods provided herein comprise contacting an analyte with a target binding moiety or target binding unit. For example, a method can comprise contacting an antibody with a target binding moiety or target binding unit. In some embodiments, the antibody is a mixture of antibodies. Contacting the mixture of antibodies with one or more target binding moiety can be used to identify a target binding moiety that binds to an antibody of the mixture of antibodies. Identification of a target binding moiety that binds to an analyte can be performed in solution or on a surface.

In some embodiments, the analyte can be a biomarker. In some embodiment, the amount of the analyte from a patient sample is different from the amount of the analyte from a healthy sample. In some embodiments, quantification of the amount of an analyte from a patient sample and a healthy sample can be used for disease diagnosis and prognosis. An array comprising target binding moieties or target binding units described herein can be used to detect or quantify an analyte from a patient sample and a healthy sample.

Antibody

In some embodiments, an analyte is an immunoglobulin, an antibody or an antigen binding domain thereof. A whole immunoglobulin or antibody typically can consist of four polypeptides: two identical copies of a heavy (H) chain polypeptide and two identical copies of a light (L) chain polypeptide. In mammals, antibodies are divided into five isotypes: IgG, IgM, IgA, IgD and IgE. The isotypes differ in their biological properties, functional locations and ability to deal with different antigens. The type of heavy chain present defines the class of an antibody. There are five types of mammalian Ig heavy chain denoted by Greek letters: α, δ, ε, γ and μ. These chains are found in IgA, IgD, IgE, IgG and IgM antibodies, respectively. Heavy chains differ in size and composition; α and γ contain approximately 450 amino acids, while μ and ε have approximately 550 amino acids. Each of the heavy chains can contain one N-terminal variable ($V_H$) region and three C-terminal constant ($C_H1$, $C_H2$, and $C_H3$) regions, and each light chain can contain one N-terminal variable ($V_L$) region and one C-terminal constant ($C_L$) region. Immunoglobulin light chains can be assigned to one of two distinct types, either kappa (κ) or lambda (λ), based upon the amino acid sequences of their constant domains. In a typical immunoglobulin, each light chain can be linked to a heavy chain by disulfide bonds, and the two heavy chains can be linked to each other by disulfide bonds. In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin. The light chain variable region can be aligned with the variable region of the heavy chain, and the light chain constant region can be aligned with the first constant region of the heavy chain. The remaining constant regions of the heavy chains can be aligned with each other.

The variable regions of each pair of light and heavy chains can form the antigen binding site of an antibody. $V_H$ and $V_L$ regions can have the same general structure, with each region comprising four framework (FW or FR) regions, connected by three complementarity determining regions (CDRs). The term "framework region," as used herein, can refer to the relatively conserved amino acid sequences within the variable region which are located between the hypervariable or complementarity determining regions (CDRs). In a typical immunoglobulin, there can be four framework regions in each variable domain, which are designated FR1, FR2, FR3, and FR4. The framework regions form 13 sheets that provide the structural framework of a variable region (see, e.g., C. A. Janeway et al. (eds.), Immunobiology, 5th Ed., Garland Publishing, New York, N.Y. (2001)). In a typical immunoglobulin, there can be three complementarity determining regions (CDRs) in each variable domain, which are designated CDR1, CDR2, and CDR3. The CDRs form the "hypervariable region" of an antibody, which is responsible for antigen binding. The CDRs form loops connecting, and in some cases comprising part of, the β-sheet structure formed by the framework regions. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol., 196:901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th ed. (1991)). With the exception of CDR1 in $V_H$, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (See, e.g., Fransson, Front. Biosci., 13:1619-1633(2008)). Unless otherwise indicated, residues in the variable domain are numbered herein according to Kabat et al., supra. A variable region is a domain of an antibody heavy or light chain that is involved in binding the antibody to antigen (See, e.g., Kindt et al., Kuby Immunology, 6th ed., W.H. Freeman and Co., p. 91 (2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See, e.g., Portolano et al., J. Immunol., 150:880-887 (1993); Clarkson et al., Nature 352:624-628 (1991)).

Antibodies can comprise an antigen-binding fragment (Fab) and a fragment crystallizable region (Fc). The Fc region can interact with cell surface receptors which can allow antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment can be essential for Fc receptor-mediated activity. The N-glycans attached to this site can predominantly be core-fucosylated diantennary structures of the complex type. Examples of antibody fragments include, but are not limited to, (1) a Fab fragment, which is a monovalent fragment consisting of the $V_L$, $V_H$, $C_L$, and $C_H1$ domains, (2) a F(ab')$_2$ fragment, which is a bivalent fragment comprising two Fab fragments linked by a disulfide bridge at the hinge region, (3) a Fv fragment consisting of the $V_L$ and $V_H$ domains of a single arm of an antibody, (4) a Fab' fragment, which results from breaking the disulfide bridge of an F(ab')$_2$ fragment using mild reducing conditions, (5) a disulfide-stabilized Fv fragment (dsFv), and (6) a single domain antibody (sdAb), which is an antibody single variable region domain ($V_H$ or $V_L$) polypeptide that specifically binds antigen.

While the constant regions of the light and heavy chains may not be directly involved in binding of the antibody to an antigen, the constant regions can influence the orientation of the variable regions. The constant regions can also exhibit various effector functions, such as participation in antibody-dependent complement-mediated lysis or antibody-dependent cellular toxicity via interactions with effector molecules and cells.

An antibody can also include chimeric antibodies, humanized antibodies, and recombinant antibodies, human antibodies generated from a transgenic non-human animal, as well as antibodies selected from libraries using enrichment technologies available to the artisan.

An antibody can be a protein that is found in blood or other bodily fluids of vertebrates, which is used by the immune system to identify and neutralize foreign objects, such as bacteria and viruses. An antibody can include monoclonal antibodies, polyclonal antibodies, multispecific antibodies (for example, bispecific antibodies and polyreactive antibodies), and antibody fragments. Thus, an antibody can include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). Antibody fragments are produced by recombinant DNA techniques, or by enzymatic or chemical cleavage of intact antibodies. An antibody other than a "bispecific" or "bifunctional" antibody is understood to have each of its binding sites identical. A monoclonal antibody can be obtained from a population of substantially homogeneous antibodies, i.e., the individual antibodies comprising the population are identical except for possible naturally occurring mutations that may be present in minor amounts. A polyclonal antibody can be a preparation that includes different antibodies directed against different determinants (epitopes).

Antibody Biomarkers

An antibody can serve as a biomarker for a disease diagnosis or prognosis. In some embodiments, an antibody can be a biomarker for a cancer diagnosis or prognosis. In some embodiments, an antibody can be a biomarker for an infectious disease diagnosis or prognosis. In some embodiments, an antibody can be a biomarker for an autoimmune disease diagnosis or prognosis.

Circulating antibodies elicited by a patient's own immune system after exposure to cancer proteins can be biomarkers for the early detection of cancer. In some embodiments, such circulating antibodies are autoantibodies. An advantage of autoantibodies as biomarkers can be their production in large quantities despite the presence of a relatively small amount of corresponding antigen. Autoantibodies can also be expected to have persistent concentrations and long half-lives due to limited proteolysis and clearance. The immune system constantly monitors the body for the invasion of microorganisms and foreign molecules. A tightly regulated network of antibodies, T-lymphocytes, antigen-presenting cells, cytokines, and microenvironment signals secures the development of an appropriately targeted immune response to combat infections. Foreign extracellular and surface antigens are recognized by B-lymphocytes, which respond by secreting antibodies. To mount a sustained antibody response, B cells can utilize an additional signal from T helper cells, which present the relevant antigen as peptide fragments 15-25 amino acids in length that are in complex with major histocompatibility complex (MHC) class II. Antigens can also stimulate CD8+ T lymphocytes. These cells are activated by intracellular and membrane proteins that are processed by the endogenous processing pathway and presented as peptides 8-12 amino acids in complex with MHC class I. The two systems are highly coordinated, and in most cases, high affinity immunoglobulin G (IgG) antibody responses may require recognition of the antigen by both B and T lymphocytes. During the initial development of the immune system, more than half of the newly generated B cell receptors are estimated to be capable of binding autoantigens. Most autoreactive B cells are eliminated during B cell maturation, however, preventing mature B cells from reacting with self-molecules. This selection provides the basis for the development of self-tolerance, the ability of the immune system to recognize and ignore the body's own cells and tissues. Sometimes this mechanism fails and the immune system reacts with one's own antigens as a consequence of over-expression, mutations, changes in protein half-lives, misfolding, aberrant degradation of self-proteins, or altered post-translational modifications (e.g., glycosylation and phosphorylation) of the protein. Autoantibodies have long been recognized in autoimmune diseases, including systemic lupus erythematosus, myasthenia gravis, and rheumatoid arthritis. In some of the diseases, autoantibodies play a central role in its pathogenesis (e.g., myasthenia gravis). In rheumatoid arthritis, for example, the test for an anti-IgG antibody, also known as the rheumatoid factor, is useful and has a sensitivity of approximately 80%. Autoantibodies directed against various antigens can be detected in cancer patients. The antigens are present predominantly in cancer cells while scarcely present in healthy cells.

Examples of tumor associated antibodies that can be used as biomarkers include, but are not limited to, anti-IL6, anti-IL8, anti-CA-125, anti-c-myc, anti-p53, anti-CEA, anti-CA 15-3, anti-MUC-1, anti-survivin, anti-bHCG, anti-osteopontin, anti-PDGF, anti-Her2/neu, anti-Akt1, and anti-cytokeratin 19 antibodies. In some embodiments, the presence of abnormal levels of two or more antibodies in a sample from a patient's blood indicates the presence of cancer in the patient. An array also can be provided to quantitate levels of antibody biomarkers in a patient's blood. In some embodiments, a method of predicting onset of cancer comprising determining the change in concentration over time of two or more antibodies in a sample from a patient's blood.

Target Binding Unit

Provided herein are compositions and methods comprising a target binding unit. The target binding unit can be a structural arrangement of two binding elements (e.g., peptide or peptoid sequences), each comprising a target binding region. For example, the target binding unit can be a structural arrangement of two peptide sequences. As used herein, the binding element can refer to potential immuno-receptor-binding molecule, or PIRM. In various embodiments, the peptide sequences can be replaced with peptoid sequences. The target binding unit may be the smallest unit desired to bind to a molecule of an analyte (e.g., antibody or a fragment thereof).

According to an aspect of the present disclosure, a target binding unit comprises a first peptide sequence and a second peptide sequence, wherein the first peptide sequence and the second peptide are separated by a spacer and are spaced at a distance such that the first peptide sequence and the second peptide sequence simultaneously bind to a single molecule comprising an antigen binding domain of an antibody. The first peptide sequence may have the same sequence as the second peptide sequence. The first peptide sequence may have a different sequence from the second peptide sequence. For example, the first peptide sequence has a sequence that is at least about 70%, at least about 75%, at least about 80%, at least about 85%, at least about 90%, at least about 95%, at least about 98%, at least about 99%, or 100% identical to a sequence of the second peptide sequence. In some embodiments, the first peptide sequence comprises a first binding region and the second peptide sequence comprises a second binding region. As used herein, "binding region" and "target binding region" can be used interchangeably and refer to the regions of the binding element which interacts with the analyte, for example, an epitope. In some embodiments, the first binding region and the second binding region are separated by a spacer, and are spaced at a distance such that the first binding region and the second binding region simultaneously bind to a single molecule comprising an antigen binding domain of an antibody. The binding region can be a part of the peptide sequence that physically interacts or attaches to the antigen binding domain of the molecule. For example, the binding region can be an epitope which directly interacts or attaches to the Fab of an antibody. In some embodiments, the first binding region and the second binding region have a same sequence. In some embodiments, the first binding region and the second binding region have a same epitope. In some embodiments, the first binding region and the second binding region have a same structure recognized by the single molecule.

According to another aspect of the present disclosure, a target binding unit comprises a first peptoid sequence and a second peptoid sequence, wherein the first peptoid sequence and the second peptoid sequence simultaneously bind to a single molecule comprising an antigen binding domain of an antibody.

In some embodiments, the first peptide sequence, the second peptide sequence, and the spacer are contiguous and are comprised in a single peptide chain. For example, the C-terminal end of the first peptide sequence and the N-terminal end of the spacer, the C-terminal end of the spacer and the N-terminal end of the second peptide sequence is linked by a peptide bond.

In some embodiments, the first peptide sequence, the second peptide sequence, and the spacer are not comprised in a single peptide chain. For example, the spacer can function as a scaffold and the first peptide sequence and the second peptide sequence are each linked to the opposite ends of the spacer. In some embodiments, the first peptide sequence, the second peptide sequence, and the spacer are linked by a non-peptide bond.

The spacer can be any type of polymer and can be used to separate the first peptide sequence and the second peptide sequence such that the first peptide sequence and the second peptide sequence simultaneously bind to a single molecule of an analyte. The spacer can comprise one or more chains/strands of a polymer. In some embodiments, the spacer comprises one or more chains/strands of a same type of polymer. In some embodiments, the spacer comprises one or more chains/strands of different types of polymers. In some embodiments, the polymer can be a polypeptide, a polynucleotide, or a polyalkylene glycol. The polyalkylene glycol can include polyethylene glycol (PEG) and polypropylene glycol (PPG). Other examples of polymer include, but are not limited to, cellulose acetates (including cellulose diacetate), ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosa, and copolymers, terpolymers, fibrin, gelatin, collagen, and any combinations thereof.

In some cases, the two peptide or peptoid sequences are linked to the spacer by a linker. In some cases, the linker is formed by a first reactive on the peptide or peptoid sequence, and a second reactive group on the spacer. For example, the spacer can comprise two reactive groups that can be linked to two peptide or peptoid sequences.

The spacer can be an unstructured linker. In some embodiments, a spacer folds into a structure. The structure can be a double helix structure of polynucleotide, or any secondary structure or tertiary structure of a polypeptide or a polynucleotide. In some embodiments, the spacer comprises a pre-designed amino acid sequence. For example, the pre-designed amino acid can comprise sets of glycine and serine repeats such as $(Gly_4Ser)_n$, where n is a positive integer equal to or greater than 1 (SEQ ID NO: 1). In some embodiments, the spacer comprises a folded polypeptide. In some embodiments, the spacer comprises a secondary structure and/or a tertiary structure. In some embodiments, the spacer comprises a coiled coil structure or a beta sheet structure. In some embodiments, the spacer comprises two or more separate peptide chains, wherein at least one of the two or more separate peptide chains comprise an alpha-helix or a beta-strand. In some embodiments, the spacer comprises two separate peptide chains, wherein each of the two peptide chains comprise an alpha-helix, and the two alpha-helices form a coiled coil structure. In some embodiments, the spacer comprises two separate peptide chains, wherein each of the two peptide chains comprise a beta-strand, and the two beta-strands form a beta sheet. In some embodiments, the spacer comprises a single peptide chain folded into at least two alpha-helices or at least two beta-strands. In some embodiments, the spacer comprises a single peptide chain folded into a coiled coil structure or a beta sheet structure. In some embodiments, the spacer comprises a single peptide chain, and the single peptide chain folds into four alpha-helices or four beta-strands.

In some embodiments, the spacer comprises a coiled coil structure formed by three separate peptide chains. For example, the spacer comprises a first peptide chain, a second peptide chain, and a third peptide chain, wherein the second peptide chain interacts with a first portion of the first peptide chain, and wherein the third peptide chain interacts with a second portion of the first peptide chain. In such cases, the first peptide chain, the second peptide chain, and the third peptide chain folds into an alpha-helix. In some embodiments, the second peptide chain and the third peptide chain are linked to opposite ends of a double-stranded polynucleotide. In some embodiments, the spacer comprises an oligonucleotide. In some embodiments, the spacer comprises an oligonucleotide, wherein the oligonucleotide is a double-stranded oligonucleotide.

The length of the spacer can be designed to separate two binding elements at a distance such that the two binding elements simultaneously bind to a single molecule having an antigen binding domain of an antibody. In some embodiments, the spacer is a polynucleotide. In such cases, the length of the spacer can be from 20 to 40 nucleotides, from 30 to 50 nucleotides, from 40 to 60 nucleotides, from 50 to 70 nucleotides, from 60 to 80 nucleotides, from 70 to 90 nucleotides, from 80 to 100 nucleotides, from 90 to 110 nucleotides, from 100 to 120 nucleotides, from 110 to 130 nucleotides, from 120 to 140 nucleotides, or from 130 to 150 nucleotides. In some cases, the length of the spacer can be at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, at least 100 nucleotides, or more. The polynucleotide can be double-stranded or single-stranded. In case of double-stranded polynucleotide, the length using "nucleotide" as a unit can mean "base pair". For example, 20 nucleotides in length can mean 20 base pairs in length. In some embodiments, the spacer is a polypeptide. In such cases, the length of the spacer can be from 20 to 40 amino acid residues, from 30 to 50 amino acid residues, from 40 to 60 amino acid residues, from 50 to 70 amino acid residues, from 60 to 80 amino acid residues, from 70 to 90 amino acid residues, from 80 to 100 amino acid residues, from 90 to 110 amino acid residues, from 100 to 120 amino acid residues, from 110 to 130 amino acid residues, from 120 to 140 amino acid residues, from 130 to 150 amino acid residues, from 140 to 160 amino acid residues, from 150 to 170 amino acid residues, from 160 to 180 amino acid residues, from 170 to 190 amino acid residues, or from 180 to 200 amino acid residues. In some cases, the length of the spacer can be at least 20 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 residues, at least 120 amino acid residues, at least 150 amino acid residues, or more.

The target binding unit can comprise two binding elements. In some embodiments, the binding element is a peptide sequence or a peptoid sequence. In some embodiments, the binding element can be a peptide sequence having a length from 4 to 30 amino acids, from 5 to 20 amino acids, from 6 to 10 amino acids, from 8 to 11 amino acids, or from 10 to 20 amino acids in length. In some embodiments, the binding element can be a peptide sequence having a length from 5 to 15 amino acids, from 6 to 16 amino acids, from 7 to 17 amino acids, from 8 to 18 amino acids, from 9 to 19 amino acids, from 10 to 20 amino acids, from 11 to 21 amino acids, from 12 to 22 amino acids, from 13 to 23 amino acids, from 14 to 24 amino acids, from 15 to 25 amino acids, from 16 to 26 amino acids, from 17 to 27 amino acids, from 18 to 28 amino acids, from 19 to 29 amino acids, or from 20 to 30 amino acids. In some embodiments, the binding element can be a peptide sequence having a length of at least 5 amino acids, at least 10 amino acids, at least 15 amino acids, at least 20 amino acids, at least 25 amino acids, at least 30 amino acids, at least 35 amino acids, at least 40 amino acids, at least 45 amino acids, at least 50 amino acids, or more. In some embodiments, the binding element is a peptide sequence having a folded structure. For example, the binding element can be a protein or a portion thereof. In such cases, the binding element can have a length of at least 50 amino acids, at least 60 amino acids, at least 70 amino acids, at least 80 amino acids, at least 90 amino acids, at least 100 amino acids, at least 150 amino acids, at least 200 amino acids, at least 250 amino acids, at least 300 amino acids, at least 400 amino acids, at least 500 amino acids, or more.

In some embodiments, the binding element is a peptoid sequence. In some embodiments, the binding element can be a peptoid sequence having a length from 4 to 30 residues, from 5 to 20 residues, from 6 to 10 residues, from 8 to 11 residues, or from 10 to 20 residues. In some embodiments, the binding element can be a peptoid sequence having a length from 5 to 15 residues, from 6 to 16 residues, from 7 to 17 residues, from 8 to 18 residues, from 9 to 19 residues, from 10 to 20 residues, from 11 to 21 residues, from 12 to 22 residues, from 13 to 23 residues, from 14 to 24 residues, from 15 to 25 residues, from 16 to 26 residues, from 17 to 27 residues, from 18 to 28 residues, from 19 to 29 residues, or from 20 to 30 residues. In some embodiments, the binding element can be a peptoid sequence having a length of at least 5 residues, at least 10 residues, at least 15 residues, at least 20 residues, at least 25 residues, at least 30 residues, at least 35 residues, at least 40 residues, at least 45 residues, at least 50 residues, or more.

Target Binding Moiety

A target binding moiety refers to a construct comprising one or more target binding units linked together. In some cases, the target binding moiety comprises only one target binding unit, and in such cases, the target binding unit and target binding moiety are equivalent.

Provided herein are compositions and methods comprising a target binding moiety, wherein the target binding moiety comprises one or more target binding units. A target binding unit can comprise two binding elements (e.g., peptides or peptoids) separated by a spacer.

Also provided herein are compositions and methods comprising a polynucleotide-barcoded target binding moiety, wherein the polynucleotide-barcoded target binding moiety comprises one or more target binding unit. In some cases, the polynucleotide can function as barcode which identifies or corresponds to the identity of the target binding moiety, for example, the peptide or peptoid sequence of the target binding moiety. In some cases, the polynucleotide can encode (e.g., can be transcribed and/or translated to) the peptide sequences of the target binding moiety. The polynucleotide can be detected by any methods available in the art in order to determine the sequence of the polynucleotide and hence the sequence of the corresponding peptide sequence. For example, the polynucleotide can be detected by sequencing.

In some embodiments, provided herein is a polynucleotide-barcoded target binding moiety comprises a nucleic acid sequence linked by a linker to a target binding unit comprising a first peptide sequence comprising a first binding region, and a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody; wherein the nucleic acid sequence encodes the first peptide sequence and/or the second peptide sequence.

In some embodiments, the target binding moiety comprises a first peptide and a second peptide, wherein the first peptide and the second peptide are spaced such that the first peptide and the second peptide bind to a single analyte molecule simultaneously.

The target binding moiety can comprise a linear chain or a branched chain.

In some cases, the target binding moiety comprises a linear chain, wherein the target binding units are contiguous in a single peptide chain. As described above, in such cases, the first peptide sequence, the second peptide sequence, and the spacer of each target binding unit are contiguous and are comprised in a single peptide chain. In some embodiments, the target binding moiety is a linear polymer chain. In some embodiments, the target binding moiety is a linear polypeptide chain. The first peptide, the second peptide, and the spacer of a target binding unit can be contiguous in the linear polypeptide chain. In some embodiments, the target binding moiety is a linear polypeptide chain comprising one or more target binding units, wherein the one or more target binding units are contiguous in the linear polypeptide chain.

In some other cases, the target binding moiety comprises a branched polymer chain having a main chain and two or more side chains. The main chain can be a scaffold. The two or more side chains can comprise a peptide sequence. The two or more side chains can be linked to the scaffold through a bond or a linker. In some embodiments, the scaffold of the target binding moiety is a polypeptide chain. In some embodiments, the scaffold of the target binding moiety is a polyalkylene glycol chain. In some other embodiments, the scaffold of the target binding moiety is a polynucleotide chain.

In some embodiments, the target binding moiety comprises a scaffold. In some embodiments, the scaffold comprises a polypeptide chain. A polypeptide chain can be in any length. For example, the polypeptide chain can be from 2 to 50000 amino acid residues in length. In some embodiments, a polypeptide chain can be at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid residues in length. In some embodiments, a polypeptide chain can be at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500 or more amino acid residues in length. In some embodiments, a polypeptide chain can be at most about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or less amino acid residues in length.

In some embodiments, a polypeptide chain has a total length of at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 150, at least 200, at least 250, at least 300, at least 350, at least 400, at least 450, or at least 500 amino acids. In some embodiments, a polypeptide chain has a total length of at least 500, at least 600, at least 700, at least 800, at least 900, at least 1000, at least 1200, at least 1500, at least 2000, at least 3000, at least 4000, at least 5000, at least 6000, at least 7000, at least 8000, at least 9000, or at least 10000 amino acid residues in length. In some embodiments, a polypeptide chain has a total length of at least 10000, at least 20000, at least 30000, at least 40000, or at least 5000 amino acid residues in length.

In some embodiments, a polypeptide chain has a total length of at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 40, at most 50, at most 60, at most 70, at most 80, at most 90, at most 100, at most 150, at most 200, at most 250, at most 300, at most 350, at most 400, at most 450, or at most 500 amino acids. In some embodiments, a polypeptide chain has a total length of at most 500, at most 600, at most 700, at most 800, at most 900, at most 1000, at most 1200, at most 1500, at most 2000, at most 3000, at most 4000, at most 5000, at most 6000, at most 7000, at most 8000, at most 9000, or at most 10000 amino acid residues in length. In some embodiments, a polypeptide chain has a total length of at most 10000, at most 20000, at most 30000, at most 40000, or at most 5000 amino acid residues in length.

In some embodiments, the scaffold comprises a polynucleotide chain. A polynucleotide chain can be in any length. In some embodiments, the polynucleotide chain is from 1 nucleotide to about 3,000,000 nucleotides in length, from 1 nucleotide to about 2,500,000 nucleotides in length, from 1 nucleotide to about 2,000,000 nucleotides in length, from 1 nucleotide to about 1,500,000 nucleotides in length, from 1 nucleotide to about 1,000,000 nucleotides in length, from 1 nucleotide to about 500,000 nucleotides in length, from 1 nucleotide to about 250,000 nucleotides in length, from 1 nucleotide to about 200,000 nucleotides in length or from 1 nucleotide to about 150,000 nucleotides in length. Examples of polynucleotide can also be from 1 nucleotide to about 100,000 nucleotides in length, from 1 nucleotide to about 10,000 nucleotides in length, from 1 nucleotide to about 5,000 nucleotides in length, from 4 nucleotides to about 2,000 nucleotides in length, from 6 nucleotides to about 2,000 nucleotides in length, from 10 nucleotides to about 1,000 nucleotides in length, from 10 nucleotides to about 500 nucleotides in length, from 10 nucleotides to about 300 nucleotides in length, from 10 nucleotides to about 200 nucleotides in length, or from 20 nucleotides to about 100 nucleotides in length, and any range or value in between whether overlapping or not. In some embodiments, the polynucleotide chain can be from 5 to 20 nucleotides in length, from 10 to 30 nucleotides in length, from 15 to 35 nucleotides in length, from 20 to 40 nucleotides in length, from 25 to 50 nucleotides in length, from 30 to 60 nucleotides in length, from 50 to 100 nucleotides in length, from 60 to 150 nucleotides in length, from 100 to 200 nucleotides in length, from 200 to 300 nucleotides in length, from 300 to 400 nucleotides in length, or from 400 to 500 nucleotides in length.

In some embodiments, the scaffold is a polyalkylene glycol chain. As used herein, the term "polyalkylene glycol" or "poly(alkene glycol)" refers to polyethylene glycol (poly (ethylene glycol)), polypropylene glycol, polybutylene glycol, and derivatives thereof. Other example embodiments are listed, for example, in commercial supplier catalogs, such as Shearwater Corporation's catalog "Polyethylene Glycol and Derivatives for Biomedical Applications" (2001).

Various linkers can be used to link a peptide sequence to the scaffold. As described above, in case of target binding unit, various linkers can be used to link a peptide sequence to the spacer. In some embodiments, the linker is formed by a first reactive group on the peptide sequence and a second reactive group on the scaffold or the spacer.

In some embodiments, the linker is an organic moiety that connects two parts of a compound. Such linkers can comprise a direct bond or an atom such as oxygen or sulfur, a unit such as NH, C(O), C(O)NH, SO, $SO_2$, $SO_2$NH, SS, or a chain of atoms, such as substituted or unsubstituted C1-C6 alkyl, substituted or unsubstituted $C2-C_6$ alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by O, S, S(O), SO2, NH, C(O).

A linker may be a cleavable linker. Examples of cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S) (R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases, e.g., —NHCHR$^A$C(O)NHCHR$^B$C (O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In addition to covalent linkages, two parts of a compound can be linked together by an affinity binding pair. The term "affinity binding pair" or "binding pair" refers to first and second molecules that specifically bind to each other. One member of the binding pair is conjugated with first part to be linked while the second member is conjugated with the second part to be linked. As used herein, the term "specific binding" refers to binding of the first member of the binding pair to the second member of the binding pair with greater affinity and specificity than to other molecules.

Example binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin, biotin-neutravidin, hormone (e.g., thyroxine and cortisol-hormone binding protein), receptor-receptor agonist, receptor-receptor antagonist (e.g., acetylcholine receptor-acetylcholine or an analog thereof), IgG-protein A, IgG-protein G, IgG-synthesized protein AG, lectin-carbohydrate, enzyme-enzyme cofactor, enzyme-enzyme inhibitor, and complementary oligonucleotide pairs capable of forming nucleic acid duplexes), and the like. The binding pair can also include a first molecule which is negatively charged and a second molecule which is positively charged.

An example of using binding pair conjugation is the biotin-avidin, biotin-streptavidin or biotin-neutravidin conjugation. In this approach, one of the molecules (e.g., the peptide) can be biotinylated and the other (e.g., the scaffold) can be conjugated with avidin or streptavidin. For another example, the scaffold is biotinylated and the peptide is conjugated with avidin or streptavidin. Many commercial kits can be used for biotinylating molecules.

Another example of using binding pair conjugation is the biotin-sandwich method. See, e.g., example Davis et al., Proc. Natl. Acad. Sci. USA, 103: 8155-60 (2006). The two molecules to be conjugated together can be biotinylated and then conjugated together using at least one tetravalent avidin-like molecule (e.g., avidin, streptavidin, or neutravidin) as a linker. Accordingly, in some embodiments, both the peptides and the scaffold can be biotinylated and then linked together using an avidin-like molecule (e.g., avidin, streptavidin, or neutravidin). In some embodiments, neutravidin and/or streptavidin is used as a linker to bridge together the biotinylated molecules.

Another example of using binding pair conjugation is double-stranded nucleic acid conjugation. In this approach, the first part to be linked can be conjugated with the first strand of the double-stranded nucleic acid and the second part to be linked can be conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branchpoints and nucleotide residues, groups or bridges.

Another example of using binding pair conjugation is coiled coil conjugation. In this approach, the first part to be linked is conjugated with a first peptide chain folded into an alpha-helix, and the second part to be linked is conjugated with a second peptide chain folded into an alpha-helix. The two alpha-helices interact to form a coiled coil structure to link two parts together.

Additional examples of binding pair conjugation include HaloTag, CLIP-Tag, and SNAP-Tag.

In some embodiments, the linker can be a linker molecule. Examples of linker molecules can include, but are not limited to, a polymer, sugar, nucleic acid, peptide, protein, hydrocarbon, lipid, polyethelyne glycol, crosslinker, or combination thereof.

Non-limiting examples of crosslinkers that can be used as linker molecules can include, but are not limited to, amine-to-amine crosslinkers (e.g., but are not limited to the ones based on NHS-ester and/or imidoester reactive groups), amine-to-sulfhydryl crosslinkers, carboxyl-to-amine crosslinkers (e.g., but are not limited to, carbodiimide crosslinking agents such as DCC, and/or EDC (EDAC); and/or N-hydroxysuccinimide (NHS)), photoreactive crosslinkers (e.g., but not limited to, aryl azide, diazirine and any art-recognized photoreactive (light-activated) chemical crosslinking reagents), sulfhydryl-to-carbohydrate crosslinkers (e.g., but are not limited to the ones based on malemide and/or hydrazide reactive groups), sulfhydryl- to hydroxyl crosslinkers (e.g., but are not limited to the ones based on maleimide and/or isocyanate reactive groups), sulfhydryl-to-sulfhydryl crosslinkers (e.g., but are not limited to, maleimide and/or pyridyldithiol reactive groups), sulfo-SMCC crosslinkers, sulfo-SBED biotin label transfer reagents, sulfhydryl-based biotin label transfer reagents, photoreactive amino acids (e.g., but are not limited to diazirine analogs of leucine and/or methionine), NHS-azide Staudinger ligation reagents (e.g., but are not limited to, activated azido compounds), NHS-phosphine Staudinger ligation reagents (e.g., but are not limited to, activated phosphine compounds), and any combinations thereof.

Examples of suitable reactive groups include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

Coding Moiety

In various embodiments, provided herein is a coding moiety linked to a target binding moiety. The coding moiety can be a polynucleotide or a nucleic acid sequence. The coding moiety linked to a target binding moiety can refer to a "polynucleotide-barcoded target binding moiety".

According to an aspect, the coding moiety is a single stranded polynucleotide. According to another aspect, the coding moiety is a double stranded polynucleotide. In some cases, the coding moiety may comprise a first polynucleotide portion that is single-stranded and a second polynucleotide portion that is double-stranded. The coding moiety can be a deoxyribonucleic acid, a ribonucleic acid, or a combination thereof.

The length of the coding moiety can vary. According to certain aspects, the length of the coding moiety can be from 1 nucleotide to about 3,000,000 nucleotides in length, from 1 nucleotide to about 2,500,000 nucleotides in length, from 1 nucleotide to about 2,000,000 nucleotides in length, from 1 nucleotide to about 1,500,000 nucleotides in length, from 1 nucleotide to about 1,000,000 nucleotides in length, from 1 nucleotide to about 500,000 nucleotides in length, from 1 nucleotide to about 250,000 nucleotides in length, from 1 nucleotide to about 200,000 nucleotides in length or from 1 nucleotide to about 150,000 nucleotides in length. Examples of target polynucleotide can also be from 1 nucleotide to about 100,000 nucleotides in length, from 1 nucleotide to about 10,000 nucleotides in length, from 1 nucleotide to about 5,000 nucleotides in length, from 4 nucleotides to about 2,000 nucleotides in length, from 6 nucleotides to about 2,000 nucleotides in length, from 10 nucleotides to about 1,000 nucleotides in length, from 10 nucleotides to about 500 nucleotides in length, from 10 nucleotides to about 300 nucleotides in length, from 10 nucleotides to about 200 nucleotides in length, or from 20 nucleotides to about 100 nucleotides in length, and any range or value in between whether overlapping or not. In some cases, the length of the coding moiety can be equal to or greater than about 100, 200, 300, 400, 500, 600, 700, 800, 1,000, 2,000, 3,000, 4,000, 5,000, 6,000, 7,000, 8,000, 9,000, 10,000, 15,000, 20,000, 30,000, or more nucleotides in length. In some cases, the length of the coding moiety can be equal to or greater than about 5, 10, 20, 30, 40, 50, 60, 70, 80, 90, 100, or more nucleotides in length. In case of double-stranded polynucleotides, the "nucleotides in length" means the "number of base pairs" or the length of one of the two strands in the double-stranded polynucleotides.

In some embodiments, the coding moiety is a polynucleotide comprising a barcode. The barcode can be used to determine the identity of the corresponding peptide or peptoid sequence on the target binding moiety. By sequencing, or otherwise detecting the barcode, the identity (e.g., sequence) of the peptide or peptoid comprising the target binding region can be determined.

The coding moiety can encode a peptide sequence of the target binding moiety. In various embodiments, the encoded peptide sequence is the binding element. In some embodiments, the encoded peptide sequence is the binding element fused to a peptide linker. In some embodiments, the coding moiety is a polynucleotide encoding a binding element. In some embodiments, the coding moiety is a polynucleotide encoding a binding element and a linker such that the encoded binding element can be fused to a peptide linker after expression. In some embodiments, the coding moiety is a polynucleotide encoding a peptide sequence. In such cases, the polynucleotide can be transcribed and/or translated to a polypeptide sequence. And in such cases, the target binding moiety is transcribed and/or translated from the polynucleotide. In some embodiments, the polynucleotide-barcoded target binding moiety can be manufactured by RNA display. In some embodiments, the polynucleotide-barcoded target binding moiety can be manufactured by in vitro compartmentalization, for example, by using emulsion.

Manufacturing of Target Binding Moiety

A target binding moiety, with or without a linked coding moiety, can be manufactured by several different methods. In some cases, a target binding moiety is not linked to a coding moiety, and in such cases, various methods can be used to link peptide or peptoid sequences to a scaffold as described herein, for example, through a linker and binding pairs. In some cases, a target binding moiety is attached on a solid surface, and in such cases, various methods can be used to link a target binding moiety onto a solid surface. Those methods include, but are not limited to, using a linker generated by two functional groups to link two different entities. In some other cases, a target binding moiety is linked to a coding moiety, e.g., a polynucleotide, to form a polynucleotide-barcoded target binding moiety. Described herein are three non-limiting examples of manufacturing a polynucleotide-barcoded target binding moiety, including RNA display, in vitro compartmentalization, and split-and-pool synthesis.

As described herein, in some embodiments, a target binding moiety is a polypeptide chain. To make a library of target binding moieties, a library of nucleic acid templates can be prepared first. The library of nucleic acid templates can then be used to in vitro transcribed and/or translated to make a library of target binding moieties. For example, a library of DNA templates can be prepared and then transcribed into RNA templates which can then be translated to the polypeptide chains, each having two or more binding elements. For another example, a library of RNA templates can be prepared and then translated to the polypeptide chains, each having two or more binding elements. The library of nucleic acid templates can be prepared using methods as shown in the example section, for example, Examples 3 and 11. In some cases, each of the nucleic acid templates within the library of nucleic acid template can comprise two or more subsequences that have an identical nucleic acid sequence or encode a same peptide sequence. As used herein, "library size" can be used to refer to how many unique species (e.g., target binding moieties, or unique binding element sequences) can be generated by the library of nucleic acid templates. The unique target binding moiety may refer to a target binding moiety having a unique sequence of the binding elements. In a library of target binding moieties, the sequence of the spacer and scaffold can be the same among all target binding moieties. For example, the library size of nucleic acid templates can be at least about $10^3$ species, at least about $10^4$ species, at least about $10^5$ species, at least about $10^6$ species, at least about $10^7$ species, at least about $10^8$ species, at least about $10^9$ species, at least about $10^{10}$ species, at least about $10^{11}$ species, at least about $10^{12}$ species, at least about $10^{13}$ species, at least about $10^{14}$ species, at least about $10^{15}$ species, at least about $10^{16}$ species, or more species. Using the library of nucleic acid templates, a plurality or a library of target binding moieties can be generated which have at least about $10^3$ species, at least about $10^4$ species, at least about $10^5$ species, at least about $10^6$ species, at least about $10^7$ species, at least about $10^8$ species, at least about $10^9$ species, at least about $10^{10}$ species, at least about $10^{11}$ species, at least about $10^{12}$ species, at least about $10^{13}$ species, at least about $10^{14}$ species, at least about $10^{15}$ species, at least about $10^{16}$ species, or more species.

RNA Display

The compositions containing a target binding moiety described herein can be prepared by RNA display. Using RNA display, a nucleic acid sequence encoding a peptide sequence can be physically linked to its encoded peptide sequence. In RNA display, an encoded polypeptide (e.g., protein or peptide) can be covalently attached to the RNA, for example, using a 3' puromycin tagged RNA. Puromycin is a translation inhibitor that is able to enter the ribosome during translation and form a stable covalent bond with the nascent protein/peptide. This can allow a stable covalent linkage to be formed between the RNA display template and the protein/peptide it encodes, resulting in an RNA-displayed protein/peptide.

In RNA display, members of the RNA library can be directly attached to the polypeptide of interest it encodes, e.g., by a stable covalent linkage to puromycin, an antibiotic that can mimic the aminoacyl end of tRNA. Puromycin is an aminonucleoside antibiotic, active in either prokaryotes or eukaryotes, derived from *Streptomyces alboniger*. Peptide synthesis can be inhibited by premature chain termination during translation taking place in the ribosome. Part of the molecule can act as an analog of the 3' end of a tyrosyl-tRNA, where a part of its structure can mimic a molecule of adenosine and another part mimics a molecule of tyrosine. It can enter the A site and transfer to the growing chain, causing the formation of a puromycylated nascent chain and premature chain release. The 3' position can contain an amide linkage instead of the normal ester linkage of tRNA, making the molecule much more resistant to hydrolysis and stopping procession along the ribosome.

Other puromycin analog or derivative inhibitors of protein synthesis include O-demethylpuromycin, O-propargyl-puromycin, 9-{3'-deoxy-3'-[(4-methyl-L-phenylalanyl)amino]-P-D-ribofuranosyl}-6-(N,N'-dimethylamino)purine [L-(4-

Me)-Phe-PANS] and 6-dimethylamino-9-[3-(p-azido-L-beta-phenylalanylamino)-3-deoxy-beta-ribofuranosyl] purine.

Members of the RNA library can be ligated to puromycin via a linker such as, but not limited to, a polynucleotide or a chemical linker, e.g., polyethylene glycol. In some embodiments, the polynucleotide linker is linked at the 3' terminal end to puromycin. In other embodiments, the PEG linker is linked to puromycin. As puromycin that is linked to the 3' terminal end of a RNA molecule enters a ribosome, it can establish a covalent bond to the nascent protein (encoded by the RNA molecule) as a result of peptidyl transferase activity in the ribosome. In turn, a stable amide linkage can form between the protein and the O-methyl tyrosine portion of puromycin. The RNA library of RNA-puromycin fusions can undergo in vitro translation, as described herein, to generate RNA-puromycin-protein complexes (e.g., polynucleotide-barcoded target binding moiety).

Affinity selection can be performed on the RNA-displayed peptide library to screen for proteins/peptides having given properties, such as specific binding to an analyte. The RNA display can be performed in solution or on a solid support. The selected RNA-displayed protein/peptide of interest can be purified by standard methods known in the art such as affinity chromatography. The RNA can be cloned, PCR amplified, and/or sequenced to determine the coding sequence of the selected protein/peptide of interest. In some aspects, members of a library of nucleic acid members are linked to puromycin, where each member encodes a prospective protein/peptide of interest having a primary amino acid sequence different from the other proteins/peptides encoded by the other nucleic acid members. The RNA display system can contain a population or mixture of different complexes such that each complex has a different RNA linked to puromycin, the ribosome, and a prospective protein/peptide of interest.

As provided herein, RNA display can be used to generate a library of nucleic acid-peptide fusion molecules. Libraries of diverse nucleic acid-peptide fusion molecules can be provided, wherein each molecule of the library can comprise an encoding nucleic acid linked to an encoded peptide, and wherein one or more peptides of the library can contain at least one unnatural amino acid residue. As used herein, the term "encoding nucleic acid" refers to a nucleotide sequence that comprises two or more codons that can be translated into a peptide. Similarly, the term "encoded peptide" refers to an amino acid sequence that can be translated from an encoding nucleic acid. In some cases, the encoding nucleic acid is an RNA molecule, which can be any RNA molecule that can be a template for translation of a peptide as disclosed herein, for example, an mRNA molecule transcribed from a DNA or RNA template, or a chemically synthesized RNA molecule.

According to an aspect, provided herein is a method comprising translating an RNA sequence of an RNA, wherein the RNA sequence encodes a peptide sequence, wherein the RNA is linked to a peptide acceptor at a 3' end of the RNA, linking the peptide acceptor to an amino acid residue of a translated peptide comprising the peptide sequence, thereby forming a nucleic acid-peptide fusion molecule. In some embodiments, the nucleic acid-peptide fusion molecule comprises a polynucleotide barcoded target binding moiety comprising: (i) a first peptide sequence comprising a first binding region, and (ii) a second peptide sequence comprising a second binding region; wherein the first binding region and the second binding region are (i) separated by a spacer, and (ii) spaced at a distance such that the first peptide sequence and the second peptide sequence simultaneously bind to a single molecule comprising an antigen binding domain of an antibody. In some cases, the method further comprises providing a DNA, wherein the DNA encodes the RNA. In some cases, the method further comprises transcribing the DNA. In some cases, the method may further comprise reverse transcribing the RNA. A DNA strand generated by reverse transcribing the single-stranded RNA can hybridize to the single-stranded RNA in order to stabilize the single-stranded RNA. In some embodiments, the DNA molecule and/or the RNA sequence encodes the first peptide sequence, the second peptide sequence and the spacer. In some embodiments, the nucleic acid-peptide fusion molecule comprises a plurality of nucleic acid-peptide fusion molecules. In some cases, each nucleic acid-peptide fusion molecule of the plurality comprises a unique nucleic acid sequence. The first binding region and second binding region can have a same sequence. The first binding region and second binding region can have a same structure recognized by the single molecule. The spacer of each nucleic acid-peptide fusion molecule can be the same or comprise a same amino acid sequence. In some embodiments, the spacer comprises a folded polypeptide, a secondary structure and/or a tertiary structure. For example, the spacer can comprise a coiled coil structure or a beta sheet structure. In some cases, the first peptide sequence and the second peptide sequence have a same sequence. In some cases, the first peptide sequence has a sequence that is at least about 70%, at least about 75%, at least about 80%, at least about 85%, at least about 90%, at least about 95%, at least about 98%, at least about 99%, or 100% identical to a sequence of the second peptide sequence. The antigen binding domain can be a fragment from an antibody. The antigen binding domain can be a scFv, a Fab, or a $F(ab)_2$. In some cases, the first peptide sequence and the second peptide sequence are from 4 to 30 amino acids, from 5 to 20 amino acids, from 6 to 10 amino acids, from 8 to 11 amino acids, or from 10 to 20 amino acids in length. In some cases, the first peptide sequence or the second peptide sequence is at least about 4, 5, 6, 7, 8, 9, 10, 11, 12, 13, 14, 15, 16, 17, 18, 19, 20, 21, 22, 23, 24, 25, 30, 35, 40, 45, 50, or more amino acids in length. In some embodiments, the translating comprises in vitro translating.

An advantage of the RNA display system can be that an encoding nucleic acid is translationally linked to its encoded peptide. As used herein, the term "translationally linked" refers to the joining of an encoding nucleic acid and its encoded peptide during translation of the peptide due to the catalytic activity of a ribosomal peptidyl transferase. In some cases, the encoding nucleic acid molecule can be linked, either directly or indirectly via its 3' terminus, to the encoded peptide, e.g., at the C-terminus of the peptide, during translation of the peptide. A peptide and nucleic acid can be translationally linked using a peptide acceptor. As used herein, the term "peptide acceptor" means a molecule that can be added to the C-terminus of a growing (nascent) peptide chain due to the catalytic activity of the ribosomal peptidyl transferase function. A peptide acceptor, which is exemplified by puromycin, can contain a nucleotide or nucleotide-like moiety such as adenosine or an adenosine analog (e.g., adenosine di-methylated at the N-6 amino position) linked to an amino acid or an analog or derivative thereof (e.g., O-methyl tyrosine; see, also, Ellman et al., Meth. Enzymol. 202:301, 1991, which is incorporated herein by reference), wherein the linkage is, for example, an ester, amide, or ketone linkage. A peptide acceptor also can contain a nucleophile, which can be, for example, an amino group, a hydroxyl group, or a sulfhydryl group. A peptide acceptor also can comprise a nucleotide mimetic, amino acid mimetic, or a mimetic of a combined nucleotide-amino acid structure.

A peptide acceptor can be positioned at the 3' terminus of an encoding nucleic acid molecule. As such, the peptide acceptor molecule can be positioned immediately following the final codon of the peptide coding sequence, or can be separated from the final codon by a linker, for example, an intervening nucleotide sequence, which can be DNA or RNA. In some cases, the 3' terminus of the peptide coding sequence, or the linker, when present, comprises a translation pause site. A peptide acceptor can be covalently bound to the peptide coding sequence of the nucleic acid, or can be linked non-covalently, for example, through hybridization using a second nucleotide sequence that selectively hybridizes at or near the 3' end of the peptide coding sequence and that itself is bound to a peptide acceptor molecule, or that bridges and selectively hybridizes at or near the 3' end of the peptide coding sequence and at or near a first end of a second nucleotide sequence, wherein the peptide acceptor is linked at or near the second end of the second nucleotide sequence.

An example peptide acceptor is puromycin, which resembles tyrosyl adenosine and acts to attach a growing peptide to its encoding mRNA (see U.S. Pat. No. 6,281,344). Puromycin is an antibiotic that can act as a chain terminator. As a mimetic of aminoacyl-tRNA, puromycin can act as a universal inhibitor of protein synthesis by binding the translation complex A site, accepting the growing peptide chain, and falling off the ribosome (at a $K_d=10^{-4}$ M; Traut and Monro, J. Mol. Biol. 10:63, 1964; Smith et al., J. Mol Biol. 13:617, 1965). Puromycin can form a stable amide bond to the growing peptide chain, thus allowing for more stable fusions than other peptide acceptors that form, for example, a less stable ester linkage. A peptidyl-puromycin molecule can contain a stable amide linkage between the C-terminus of the nascent peptide (i.e., the peptide while it is still bound in the translation complex) and the O-methyl tyrosine portion of the puromycin. The O-methyl tyrosine can be linked by a stable amide bond to the 3'-amino group of the modified adenosine portion of puromycin. As such, methods for translationally linking an encoding nucleic acid and encoded peptide are disclosed herein and include, for example, effecting the joining using a peptide acceptor such as puromycin, which can be linked at or near the 3' terminus of the encoding nucleic acid such that it can enter the ribosome complex during translation and be incorporated at the C-terminus of the growing (nascent) peptide, thereby terminating translation and linking the encoding nucleic acid and encoded peptide.

Additional peptide acceptors useful for translationally linking an encoding nucleic acid and an encoded peptide include, for example, tRNA-like structures at the 3' end of the mRNA, and other compounds that act in a manner similar to puromycin, for example, a compound that includes an amino acid residue linked to an adenine or an adenine-like compound (e.g., phenylalanyl-adenosine, tyrosyl adenosine, and alanyl adenosine), as well as amide-linked compounds such as phenylalanyl-3'-deoxy-3'-amino adenosine, alanyl-3'-deoxy-3'-amino adenosine, and tyrosyl-3'-deoxy-3'-amino adenosine. An example of a functional adenine-like compound is 7-deaza-adenosine (tubercidin) with a 3' amino acid attached (see Krayevsky and Kukhanova, Prog. Nucl. Acids Res. 23:2-51, 1979, which is incorporated herein by reference). Such peptide acceptors can contain a naturally occurring L-amino acid or contain an analog or derivative thereof, provided the peptide acceptor can translationally link the encoding nucleic acid and encoded peptide. A combined tRNA-like 3' structure-puromycin conjugate also can be used as a peptide acceptor.

In Vitro Compartmentalization

The compositions containing a target binding moiety described herein can be prepared by in vitro compartmentalization as an alternative method to RNA display.

A number of high-throughput display selection methods based on a physical linkage between the gene and the protein/peptide it encodes may be used (Griffiths, A. D. and Tawfik, D. S. (2000). Curr Opin Biotechnol 11, 338-53). These provide methods of selecting proteins or peptides that bind any given analyte. The present disclosure provides an in vitro system for compartmentalization of large molecular libraries (e.g., a library of target binding moieties comprising peptides) and provides methods for selection and isolation of target binding moieties having given activities (e.g., binding to an antibody) from such libraries. In the methods provided herein, a unique peptide sequence can be linked with a unique nucleic acid sequence in an individual compartment so that the unique nucleic acid sequence can be used to identify the peptide sequence after pooling. In some cases, the method to link a peptide sequence and a nucleic acid sequence can be to compartmentalize a nucleic acid sequence encoding a peptide into an individual compartment and perform in vitro transcription and translation to produce two or more copies of the peptides. In some embodiments, the nucleic acid sequence is a single molecule. In some embodiments, a single molecule comprises one or more clonal copies of a sequence. In some embodiments, the nucleic acid is two or more clonal copies of a single molecule. In some embodiments, the nucleic acid comprises two or more clonal copies of a sequence. In some embodiments, the two or more clonal copies of a single molecule can be linked to a solid support, e.g., a bead. As used herein, "clonal copy" refers to the copies originated from a single molecule template during amplification. In some embodiments, the nucleic acid can be RNA, and in such cases, only in vitro translation is performed. And the nucleic acid sequence can be linked to a scaffold containing a functional group at each end. After producing two or more copies of the peptide in the compartment, two copies of the peptide can be linked to the scaffold though the two functional groups of the scaffold. The peptides can comprise a functional group that can react with the functional group on the scaffold to form a covalent linkage.

In some embodiments, a compartment comprises a nucleic acid sequence, wherein the nucleic acid sequence is further linked to a scaffold. In some embodiments, the scaffold has a first linking site and second linking site, wherein the first linking site is linked to a first peptide sequence and the second linking site is linked to a second peptide sequence. The linker can be any type of suitable linker. For example, the linker can be covalent or non-covalent. For example, the linker can be a bond or a molecule. For another example, the linker can be a cross-linker or a binding pair conjugation. The peptide can be produced by in vitro transcription and translation (or just in vitro translation) from the nucleic acid sequence.

In some embodiments, provided herein is a plurality of compartments, each compartment of the plurality comprises a unique nucleic acid sequence linked to a scaffold.

The target binding moiety linked to a coding moiety produced by in vitro compartmentalization can be further pooled together for downstream applications.

In some embodiments, provided herein is a method comprising (a) expressing a first peptide sequence encoded by a nucleic acid and a second peptide sequence encoded by a nucleic acid in each vessel of a plurality of vessels, wherein each vessel of the plurality comprises a scaffold comprising a first linking site and a second linking site separated by a spacer; and (b) binding the first peptide sequence to the first linking site and the second peptide sequence to the second linking site, wherein the first peptide sequence bound to the first linking site and the second peptide sequence bound to the second linking site are spaced at a distance such that the first peptide sequence and the second peptide sequence simultaneously bind to a single molecule comprising an antigen binding domain of an antibody, thereby forming a plurality of target binding moieties. In some cases, the nucleic acid is linked to the scaffold by a linker. In some cases, a 5' end or a 3' end of the nucleic acid is linked to the scaffold by the linker. In some cases, the nucleic acid is a single nucleic acid molecule. The nucleic acid can be linked to the scaffold before or after generating the plurality of vessels. In some cases, the nucleic acid molecule is double-stranded or single-stranded. In some cases, the nucleic acid molecule is a DNA, a RNA, or a combination thereof. The expressing can comprise transcribing and/or translating. In some cases, a template is a DNA, then expressing comprises transcribing and translating. In some cases, a template is a RNA, then expressing comprises translating. In some cases, the first peptide sequence and the second peptide sequence comprise a same sequence. In some cases, the first peptide sequence has a sequence that is at least about 70%, at least about 75%, at least about 80%, at least about 85%, at least about 90%, at least about 95%, at least about 98%, at least about 99%, or 100% identical to a sequence of the second peptide sequence. In some cases, the method further comprises pooling a plurality of polynucleotide-barcoded target binding moieties from the vessels. In some cases, the vessels are droplets. For example, the droplets are water-in-oil droplets.

The method can further comprise barcoding the target binding moieties of the plurality. In some cases, barcoding comprises attaching barcodes to the target binding moieties. In some embodiments, the scaffold is attached to a barcoded polynucleotide before expressing. In some embodiments, the scaffold is attached to the nucleic acid encoding the first peptide sequence and/or the nucleic acid encoding the second peptide sequence. In some embodiments, the scaffold is attached to the nucleic acid encoding the first peptide sequence and/or the nucleic acid encoding the second peptide sequence before expressing.

As used herein, a compartment can be a vessel or a droplet.

In some cases, the methods provided herein comprise partitioning compositions into compartments so that in some compartments there can be only one nucleic acid sequence in a compartment. The nucleic acid sequence can be transcribed and/or translated into a peptide sequence. In some embodiments, at least 50%, 60%, 70%, 75%, 80%, 85%, 90%, 95%, 96%, 97%, 98%, 99%, or 100% of the compartments contain zero or only one nucleic acid sequence. The number of partitions or compartments employed can vary depending on the application. For example, the number of partitions or compartments can be about 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of partitions or compartments can be at least about 1, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of partitions or compartments can be less than about 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or less than about 20000000. The number of partitions or compartments can be from 5 to about 10000000, from 5 to about 5000000, from 5 to about 1000000, from 10 to about 10000, from 10 to about 5000, from 10 to about 1000, from about 1000 to about 6000, from about 1000 to about 5000, from about 1000 to about 4000, from about 1000 to about 3000, or from about 1000 to about 2000.

The number of nucleic acid molecules that are partitioned into compartments can be about 1, 2, 3, 4, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or more. The number of nucleic acid molecules that are partitioned into compartments can be at least about 1, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or $10^8$, $10^9$, $10^{10}$, $10^{11}$, $10^{12}$, $10^{13}$, $10^{14}$, $10^{15}$, $10^{16}$, or more. The number of nucleic acid molecules that are partitioned into compartments can be less than about 2, 5, 10, 50, 100, 250, 500, 750, 1000, 1500, 2000, 2500, 5000, 7500, or 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000, or $10^8$, $10^9$, $10^{10}$, $10^{11}$, $10^{12}$, $10^{13}$, $10^{14}$, $10^{15}$, or less than $10^{16}$. The number of nucleic acid molecules that are partitioned into compartments can be from 5 to about 10000000, from 5 to about 5000000, from 5 to about 1000000, from 10 to about 10000, from 10 to about 5000, from 10 to about 1000, from about 1000 to about 6000, from about 1000 to about 5000, from about 1000 to about 4000, from about 1000 to about 3000, or from about 1000 to about 2000. In some embodiments, each of the nucleic acid molecules has a unique sequence. In some embodiments, two or more of the nucleic acid molecules may have the same sequence.

In some embodiments, the partition is an emulsion formed passively using a microfluidics device. These methods can involve squeezing, dripping, jetting, tip-streaming, tip-multi-breaking, or similar. Passive microfluidic droplet generation can be modulated to control the particle number, size, and diameter by altering the competing forces of two different fluids. These forces can be capillary, viscosity, and/or inertial forces upon the mixing of two solutions.

In some embodiments, the compartments are wells in a standard microwell plate with separation aided by sorting. In some embodiments, the sorter is a fluorescence activated cell sorter (FACS). Additionally, partitioning can be coupled with automated library generation in separated microfluidics chambers, as is the case with the Fluidigm C1.

In some embodiments, the partition is a subnanoliter well and particles are sealed by a semipermeable membrane.

In some embodiments, the partition is a microfluidics droplet formed by active control of a microfluidics chip. In active control, droplet generation can be manipulated via external force application, such as electric, magnetic, or centripetal forces. A popular method for controlling active manipulation of droplets in a microfluidic chip is to modify intrinsic forces by tuning fluid velocities of two mixing solutions, such as oil and water.

Split-and-Pool Synthesis

Target binding moiety or polynucleotide-barcoded target binding moiety can also be manufactured using split-and-pool synthesis.

In some cases, a polynucleotide-barcoded target binding moiety comprising two or more binding elements is synthesized by split-and-pool. In this method, for example, a scaffold having two binding element initiators can be provided, wherein the scaffold can be further linked a polynucleotide initiator. Different chemical building blocks can be used for synthesizing two identical binding elements from the two binding element initiators in a combinatorial manner. While synthesizing the two binding elements, a polynucleotide chain can be synthesized from the polynucleotide initiator using short nucleotide segments as building blocks. Each short nucleotide segment having a unique sequence corresponds to a unique chemical building block. Since the binding elements and the polynucleotide chain can be synthesized simultaneously, the full sequence of the polynucleotide chain can be used to determine the order of the additional of each building block and therefore identifies the identity of the whole binding element. In some cases, the binding element is peptide. The building block can be at least 5, 10, 15, 20 or more different amino acids. Each amino acid can correspond to a short DNA sequence, and vice versa. After split-and-pool synthesis, the polynucleotide sequence can be used to determine the peptide sequence of the binding element. In some other cases, the binding element is peptoid, and the peptoid sequence can be synthesized using the split-and-pool described herein. In some other cases, the binding element may be a chemical other than peptide or peptoid, and can also be synthesized using the split-and-pool synthesis described herein.

Barcode

As described herein, the coding moiety identifies or corresponds to the target binding moiety. For example, the coding moiety can identify or correspond to the peptide or peptoid sequences of the target binding moiety.

The coding moiety described herein can function as a barcode. In some embodiments, the whole coding moiety functions as a barcode. In some embodiments, a portion of the coding moiety functions as a barcode. A barcode or barcode sequence can be a natural or synthetic nucleic acid sequence comprised by a polynucleotide allowing for unambiguous identification of the polynucleotide and other sequences (e.g., a peptide sequence linked to the polynucleotide) having the same barcode sequence. A barcode can be any suitable length, such as 2 to 100 nucleotides in length. A barcode can have random sequences or pre-determined sequences. A barcode sequence can comprise a sequence of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 45, at least 50, at least 55, at least 60, at least 65, at least 70, at least 75, at least 80, at least 85, at least 90, at least 95, or at least 100 consecutive nucleotides. A barcode sequence can comprise a sequence of at least about 5, 10, 15, 20, 25, 30, 35, 40, 45, 50, 100, 200, 300, 400, 500, 600, or more consecutive nucleotides. A barcode sequence can comprise a randomly assembled sequence of nucleotides. A barcode sequence can be a degenerate sequence. A barcode sequence can be a known sequence. A barcode sequence can be a predefined sequence. A barcode can comprise one or more barcode segments, wherein the one or more barcode segments are consecutive or separated by one or more predefined sequences. A barcode can be single-stranded or double-stranded nucleic acid.

A barcode can have a length within a range of from 2 to 36 nucleotides, or from 4 to 36 nucleotides, or from 6 to 30 nucleotides, or from 8 to 20 nucleotides, or from 2 to 20 nucleotides, or from 4 to 20 nucleotides, or from 6 to 20 nucleotides. In some embodiments, a barcode can have a length within a range of from 3 to 10 nucleotides, or from 10 to 50 nucleotides, or from 50 to 100 nucleotides. In certain aspects, the melting temperatures of barcodes within a set are within 10° C. of one another, within 5° C. of one another, or within 2° C. of one another. In certain aspects, the melting temperatures of barcodes within a set are not within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

In some cases, a barcode sequence can be flanked by a predefined sequence on 5' and/or 3' side of the barcode sequence. In some cases, a barcode sequence can be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 45, at least 50, or more nucleotides in length. In some cases, a barcode sequence can be from 2 to 4, from 3 to 10 nucleotides, from 5 to 10, from 6 to 12, from 10 to 15, from 15 to 20, from 20 to 30, from 30 to 40, from 40 to 50, or from 10 to 50 nucleotides in length. The predefined sequence flanking a barcode can be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 45, at least 50, or more nucleotides in length. In some cases, the predefined sequence flanking a barcode sequence can be from 2 to 4, from 3 to 10 nucleotides, from 5 to 10, from 6 to 12, from 10 to 15, from 15 to 20, from 20 to 30, from 30 to 40, from 40 to 50, or from 10 to 50 nucleotides in length.

In some embodiments, each barcode in a plurality of barcodes has at least 2 nucleotides. For example, each barcode in a plurality of barcodes can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each barcode in a plurality of barcodes has at most about 1000 nucleotides. For example, a barcode in a plurality of barcodes can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each a barcode in a plurality of barcodes has the same length of nucleotides. For example, a barcode in a plurality barcodes can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more barcodes in a plurality of barcodes have a different length of nucleotides. For example, one or more first barcodes in a plurality of barcodes can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second barcodes in a plurality of barcodes can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first barcodes is different than the one or more second barcodes.

The barcodes in a population of barcodes can have at least 10, 15, 20, 25, 30, 35, 40, 45, 50, 60, 70, 80, 90, 100, 200, 300, 400, 500, 600, 700, 800, 900, 1000 or more different sequences. For example, the barcodes in a population can have at least about 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences.

Methods of Using

Provided herein are methods to use the compositions described herein. According to an aspect, provided herein are methods to identify target binding units or moieties that can bind to analytes obtained from a healthy sample or a diseased sample. According to another aspect, provided herein are methods to use the identified target binding units or moieties to profile analytes in a sample obtained from a subject. In various embodiments, the analytes are antibodies.

According to some embodiments, provided herein are methods comprising: contacting a mixture of antibodies with a population of target binding moieties, wherein each target binding moiety of the population comprises a target binding unit having a first binding region and a second binding region, wherein the first binding region and the second binding region are separated by a spacer and spaced at a distance such that the first binding region and the second binding region simultaneously bind to a single antibody molecule of the mixture. In some cases, the target binding unit further comprises a first peptide and/or peptoid sequence having the first binding region and a second peptide and/or peptoid sequence having the second binding region. In some cases, the first binding region and the second binding region have a same sequence. In some cases, the first binding region and the second binding region have a same structure that recognized by the single molecule.

According to some embodiments, provided herein is a method for selecting a panel of peptides, comprising: (a) providing two or more copies of an array comprising a first array and a second array; (b) obtaining a first mixture of antibodies from a diseased subject and a second mixture of antibodies from a healthy subject; (c) contacting the first mixture with the first array and the second mixture with the second array, wherein each array has at least $10^4$ discrete regions, wherein each of the discrete regions has a unique type of target binding moieties having a first binding region and a second binding region, wherein the first binding region and the second binding region are separated by a spacer and spaced at a distance such that the first binding region and the second binding region simultaneously bind to a single antibody molecule of the mixture; (d) removing an unbound fraction of antibodies on both the first and the second array; (e) quantifying an amount of bound antibodies on each of the discrete regions on the first array and the second array; and (f) identifying peptides of the second array not bound by an antibody on the first array.

According to some other embodiments, provided herein is a method for selecting a panel of peptides, comprising: (a) providing a first solution and a second solution; (b) obtaining a first mixture of antibodies from a diseased subject and a second mixture of antibodies from a healthy subject; (c) contacting the first mixture with the first solution and the second mixture with the second solution, wherein each of the first and the second solution comprises a plurality of polynucleotide-barcoded target binding moieties, each polynucleotide-barcoded target binding moiety of the plurality comprising (i) a nucleic acid sequence linked by a linker to (ii) a target binding unit comprising a first peptide sequence comprising a first binding region, and a second peptide sequence comprising a second binding region; wherein the first binding region and the second binding region are separated by a spacer, and spaced at a distance such that the first peptide sequence and the second peptide sequence simultaneously bind to a single molecule comprising an antigen binding domain of an antibody; (d) capturing antibody-bound polynucleotide-barcoded target binding moieties of the plurality in the first solution and the second solution; (e) sequencing the nucleic acid sequence captured from the first solution and the second solution; and (f) selecting the panel of peptides.

On Array Identification

In some applications, the population of target binding moieties is provided on a solid support. In such cases, the method of using the target binding moieties can be similar to the methods of using a peptide array. For example, a peptide microarray (also known as peptide chip or peptide epitope microarray) is a collection of peptides displayed on a solid surface, e.g., a glass or plastic chip. The assay principle of peptide microarrays is similar to an ELISA protocol. The peptides (e.g., tens of thousands in multiple copies) can be linked to the surface of a glass chip having the size and shape of a microscope slide. This peptide chip can directly be incubated with a variety of different biological samples, such as purified enzymes, antibodies, patient or animal sera, or cell lysates, and then be detected through a label-dependent fashion, for example, by a primary antibody that targets the bound protein or modified substrates. After several washing steps a secondary antibody with the needed specificity (e.g., anti IgG human/mouse or anti phosphotyrosine or anti myc) can be applied. The secondary antibody can be tagged by a fluorescence label that can be detected by a fluorescence scanner. Other label-dependent detection methods that can be used include, but are not limited to, chemiluminescence, colorimetric or autoradiography. In some cases, the population of target binding moieties is immobilized on the solid support. The solid support can have at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about $10^3$, at least about $10^4$, at least about $10^5$, or at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, at least about $10^{20}$, or more discrete regions. In some cases, each of the discrete regions has a different target binding moieties from the population immobilized thereon. In some cases, the different target binding moieties from the population comprises a same binding region. In some cases, the different target binding moieties from the population comprises a same peptide and/or peptoid sequence. In some cases, each of the discrete regions has two or more copies of the different target binding moieties. The method can further comprise removing unbound antibodies of the mixture. For example, removing can comprise washing a surface of the solid support with a buffer. The method can further comprise quantifying an amount of antibodies bound at each of the discrete regions. The quantifying can comprise detecting a fluorescent signal, an electrochemical signal, a chemiluminescent signal, a chromogenic signal, or a combination thereof. Various methods can be used herein to quantify the amount of antibodies bound, for example, through an antibody-binding agent having a detectable label. The antibody-binding agent can be a polynucleotide, a polypeptide (e.g., a protein, an enzyme and a glycoprotein), an aptamer, a peptidomimetic, or a small molecule (e.g., a sugar and a lipid). The detectable label can be an optical label. In some cases, the optical label can be selected from the group consisting of a small-molecule dye, a fluorescent molecule or protein, a quantum dot, a colorimetric reagent, a chromogenic molecule or protein, a Raman label, a chromophore, and any combinations thereof. In some cases, the detectable label or optical label can be a fluorescent molecule or protein. The detectable label can generate a signal signature. Types of signal signature(s) can vary. For example, the detectable label can comprise an optical molecule or label, thus producing optical signatures. Examples of optical signatures can include, without limitations, signatures of fluorescent color (e.g., emission spectra under one or more excitation spectra), visible light, no-color or no-light, color (e.g., color defined by a visible light wavelength), Raman signatures, and any combinations thereof. In some embodiments, an optical signature can comprise signatures of one or more fluorescent colors, one or more visible lights, one or more no-colors or no-lights, one or more colors, one or more Raman signatures, or any combinations thereof. For example, an optical signature can comprise a plurality (e.g., at least 2 or more) of fluorescent colors (e.g., fluorescent dyes). The optical signatures can be detected by optical imaging or spectroscopy.

In some cases, the method further comprises obtaining a blood sample from a subject. In some cases, the method further comprises preparing a serum sample from the blood sample, wherein the serum sample comprises the mixture of antibodies. In some cases, the subject comprises a diseased subject and/or a healthy subject. In some cases, the method further comprises obtaining a first serum sample from the diseased subject and a second serum sample from the healthy subject, wherein the quantifying comprises quantifying an amount of antibodies bound at each of the discrete regions in the first serum sample on a first solid support and the second serum sample on a second solid support. In some cases, the method further comprises comparing the amount of antibodies bound at each of the discrete regions on the first solid support and the amount of antibodies bound at each of the discrete regions on the second solid support. In some cases, the method further comprises selecting a panel of peptides of the discrete regions having a difference in the amount of antibodies bound on the first solid support and the second solid support.

In Solution Identification

In some applications, the population of target binding moieties is provided in solution. In some cases, each of the population of target binding moieties is linked to a coding moiety. The coding moiety can be a polynucleotide. For example, the polynucleotide is a deoxyribonucleic acid (DNA), a ribonucleic acid (RNA), or a combination thereof. In some cases, the polynucleotide is a single-stranded DNA, a single-stranded RNA, a double-stranded DNA, a double-stranded RNA, or a double-stranded DNA-RNA hybrid. In some cases, the coding moiety comprises a nucleic acid sequence that identifies a sequence of the target binding moiety. In some cases, the nucleic acid sequence encodes a peptide sequence of the two or more target binding moieties. In some cases, the population of target binding moieties comprises at least about 100, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, at least about $10^{20}$, or more different types of target binding moieties. As used herein, each type of target binding moieties from the population comprises a same (or unique) target binding region. In some cases, each type of target binding moieties from the population comprises a same peptide and/or peptoid sequence. In some cases, the coding moiety is unique to each type of target binding moieties of the population. In some cases, the method further comprises capturing, enriching, or isolating an antibody-bound fraction of target binding moieties of the population. As used herein, "capturing", "enriching", "isolating" or equivalent can be used interchangeably and can refer to purifying a fraction from the rest of the population. Various methods can be used for capturing, enriching or isolating antibodies or antibody-bound target binding moieties, for example, using immunoglobulin-binding proteins such as protein A. In addition to protein A, other immunoglobulin-binding proteins such as Protein G, Protein A/G and Protein L can be used to purify, immobilize or detect immunoglobulins. In some cases, the method further comprises amplifying a coding moiety of the antibody-bound fraction of target binding moieties. In some cases, the method further comprises quantifying the coding moiety or a copy of the coding moiety of the antibody-bound fraction. In some cases, quantifying comprises sequencing the coding moiety or a copy of the coding moiety of the antibody-bound fraction of target binding moieties. In some cases, the method further comprises obtaining a blood sample from a subject. In some cases, the method further comprises preparing a serum sample from the blood sample, wherein the serum sample comprises the mixture of antibodies. In some cases, the subject comprises a diseased subject and/or a healthy subject. In some cases, the method further comprises obtaining a first serum sample from the diseased subject and a second serum sample from the healthy subject, wherein the quantifying comprises quantifying an amount of the antibody-bound fraction of target binding moieties in the first serum sample and an amount of the antibody-bound fraction of target binding moieties in the second serum sample. In some cases, the method further comprises comparing the amount of the antibody-bound fraction of target binding moieties in the first serum sample and the amount of the antibody-bound fraction in the second serum sample. A difference between the amount of the antibody-bound fraction of target binding moieties in the first serum sample and the second serum sample can be observed. In some cases, the method further comprises selecting a panel of peptides, wherein each peptide of the panel has a difference in the amount of antibody-bound fraction of target binding moieties in the first serum sample and the second serum sample. In some cases, each peptide of the panel is identified abundantly in the first serum sample but not in the second serum sample, or is identified abundantly in the second serum sample but not in the first serum sample. In some cases, the method further comprises making the population of target binding moieties each linked to the coding moiety by RNA display. And in such cases, each of the population of target binding moieties further comprises a puromycin moiety or a variant thereof.

In some embodiments, the first peptide and/or peptoid sequence has a sequence that is at least about 70%, at least about 75%, at least about 80%, at least about 85%, at least about 90%, at least about 95%, at least about 98%, at least about 99%, or 100% identical to a sequence of the second peptide and/or peptoid sequence. In some cases, the first peptide sequence, the second peptide sequence, and the spacer are linked by a peptide bond. In some cases, the first peptide and/or peptoid sequence, the second peptide and/or peptoid sequence, and the spacer are linked by a non-peptide bond, for example, in the format of a branched chain. In some cases, the target binding moiety comprises two or more target binding units. In some cases, the first binding region and/or the second binding region are from 4 to 30 residues, from 5 to 20 residues, from 6 to 10 residues, from 8 to 11 residues, or from 10 to 20 residues in length. In some cases, the first peptide/peptoid sequence, and/or the second peptide/peptoid sequence is at least 5 residues in length. In some cases, the spacer comprises a polymer. In some cases, the spacer comprises a pre-designed amino acid sequence. In some cases, the spacer of each target binding moiety comprises a same amino acid sequence. The spacer can be a polypeptide, a polynucleotide, or a polyethylene glycol. In some cases, the spacer region comprises a folded polypeptide, a secondary structure, and/or a tertiary structure. In some cases, the folded polypeptide comprises a coiled coil structure or a beta sheet. In some cases, the coiled coil structure is formed by two separate peptide strands, wherein each of the two separate peptide strands folds into an alpha-helix. In some cases, the coiled coil structure is formed by a single peptide strand comprising at least two regions folded into alpha-helices. In some cases, the single peptide strand comprises four regions folded into alpha-helices. In some cases, the coiled coil structure is formed by a first peptide strand, a second peptide strand, and a third peptide strand, wherein the second peptide strand interacts with a first portion of the first peptide strand, and the third peptide strand interacts with a second portion of the first peptide strand. In some cases, the second peptide strand and the third peptide strand are linked to opposite ends of a double-stranded polynucleotide. In some cases, the spacer region comprises a double-stranded deoxyribonucleic acid. In some cases, the mixture of antibodies is a mixture of monoclonal antibodies, a mixture of polyclonal antibodies, or a combination thereof. In some cases, the mixture of antibodies comprises a biomarker.

Antibody Profiling

The target binding units or moieties provided herein can be used to profile antibodies in a sample. For example, the target binding units or moieties can be used to distinguish serum antibody repertoires of diseased or healthy subjects.

In some embodiments, provided herein is a method for profiling a mixture of antibodies from a subject, comprising: contacting the mixture of antibodies with an array having at least 10 discrete regions, wherein each of the discrete regions has a unique type of target binding moieties, wherein each of the unique type of target binding moieties comprises a first binding region and a second binding region, wherein the first binding region and the second binding region are separated by a spacer and spaced at a distance such that the first binding region and the second binding region simultaneously bind to a single antibody molecule of the mixture. In some cases, the method further comprises removing an unbound fraction of antibodies of the mixture. In some cases, the method further comprises detecting a bound fraction antibodies of the mixture on the array, wherein a signal is observed at each of the discrete regions having antibodies bound thereon, thereby generating a signal pattern on the array. In some cases, the method further comprises identifying a disease of the subject. In some cases, the disease is an auto-immune disease, a cancer, or an infectious disease.

In some embodiments, each of the unique type of target binding moieties further comprises a first peptide and/or peptoid sequence having the first binding region and a second peptide and/or peptoid sequence having the second binding region. In some cases, the first binding region and the second binding region have a same sequence. In some cases, the first binding region and the second binding region have a same structure that recognized by the single molecule. In some cases, the first peptide and/or peptoid sequence has a sequence that is at least about 70%, at least about 75%, at least about 80%, at least about 85%, at least about 90%, at least about 95%, at least about 98%, at least about 99%, or 100% identical to a sequence of the second peptide and/or peptoid sequence. In some cases, the first peptide sequence, the second peptide sequence, and the spacer are linked by a peptide bond. In some other cases, the first peptide and/or peptoid sequence, the second peptide and/or peptoid sequence, and the spacer are linked by a non-peptide bond. In some cases, the target binding moiety comprises two or more binding regions. In some cases, the first peptide and/or peptoid sequence, or the second peptide and/or peptoid sequence is at least 5 residues in length. In some cases, the spacer comprises a polymer. In some cases, the spacer comprises a same amino acid sequence. The spacer can be a polypeptide, a polynucleotide, or a polyethylene glycol. In some cases, the spacer may not have a structure. In some other cases, the spacer comprises a folded polypeptide, a secondary structure, and/or a tertiary structure. The folded polypeptide can comprise a coiled coil structure or a beta sheet. In some cases, the coiled coil structure is formed by two separate peptide strands, wherein each of the two separate peptide strands folds into an alpha-helix. In some cases, the coiled coil structure is formed by a single peptide strand comprising at least two regions folded into alpha-helices. In some cases, single peptide strand comprises four regions folded into alpha-helices. In some cases, the coiled coil structure is formed by a first peptide strand, a second peptide strand, and a third peptide strand, wherein the second peptide strand interacts with a first portion of the first peptide strand, and the third peptide strand interacts with a second portion of the first peptide strand. In some cases, the second peptide strand and the third peptide strand are linked to opposite ends of a double-stranded polynucleotide. In some cases, the spacer comprises a double-stranded deoxyribonucleic acid. The mixture of antibodies can be any type of antibodies. For example, the mixture of antibodies is a mixture of monoclonal antibodies, a mixture of polyclonal antibodies, or a combination thereof. In some cases, the mixture of antibodies comprises a biomarker.

Attachment to Solid Support

Various methods can be used to attach target binding moiety to a solid support. For example, in various embodiments, the target binding moiety can be attached to a solid support through a linker. The linker can be formed by a first reactive group on the target binding moiety and a second reactive group immobilized on the solid support. In some cases, the reaction group of the target binding moiety is on the scaffold. In some cases, the scaffold is polynucleotide, and the reactive group of the target binding moiety is conjugated to the polynucleotide. In some cases, the scaffold is polypeptide, and the reactive group of the target binding moiety is conjugated to the polypeptide. Various methods can be used to conjugate reactive groups to polynucleotide or polypeptide.

A wide variety of suitable reactive groups can be used. Such suitable reactive groups can include but are not limited to, for example, amino, hydroxyl, carboxyl, carboxylate, aldehyde, ester, ether (e.g., thio-ether), amide, amine, nitrile, vinyl, sulfide, sulfonyl, phosphoryl, or similarly chemically reactive groups. Additional suitable reactive groups include, but are not limited to, maleimide, N hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acylimidazole, imidazolecarbamate, vinylsulfone, succinimidylcarbonate, arylazide, anhydride, diazoacetate, benzophenone, isothiocyanate, isocyanate, imidoester, fluorobenzene.

In some embodiments, one of the reactive groups is an electrophilic moiety, and the second reactive group is a nucleophilic moiety. Either the nucleophilic moiety or the electrophilic moiety can be attached to the target binding moiety. That reactive group can then be used in a reaction that couples the target binding moiety to the solid support. Suitable electrophilic moieties can be used to react with nucleophilic moieties to form a covalent bond. Such electrophilic moieties include, but are not limited to, e.g., carbonyl group, a sulfonyl group, an aldehyde group, a ketone group, a hindered ester group, a thioester group, a stable imine group, an epoxide group, an aziridine group, etc.

The product of the reaction between the nucleophile and the electrophile can incorporate the atoms originally present, e.g., in the nucleophilic moiety. In some embodiments, the electrophile is an aldehyde or ketone with the nucleophilic moiety including reaction products such as an oxime, an amide, a hydrazone, a reduced hydrazone, a carbohydrazone, a thiocarbohydrazone, a sufonylhydrazone, a semicarbazone, a thiosemicarbazone, or similar functionality, depending on the nucleophilic moiety used and the electrophilic moiety (e.g., aldehyde, ketone, and/or the like) that is reacted with the nucleophilic moiety. Linkages with carboxylic acids can be referred to as carbohydrazides or as hydroxamic acids. Linkages with sulfonic acids can be referred to as sulfonylhydrazides or N-sulfonylhydroxylamines. The resulting linkage can be subsequently stabilized by chemical reduction.

In some embodiments, one of the reactive groups is an electrophile, e.g., an aldehyde or ketone, and the second reactive group is a nucleophilic moiety. Either the nucleophilic moiety or the electrophilic can be attached to the target binding moiety; the remaining reactive group is then attached to the solid support. Suitable nucleophilic moieties that can react with aldehydes and ketones to form a covalent bond include, for example, aliphatic or aromatic amines, such as ethylenediamine. In other embodiments, the reactive group is —NR$^1$—NH$_2$ (hydrazide), —NR$^1$(C=O)NR$^2$NH$_2$ (semicarbazide), —NW (C=S)NR$_2$NH$_2$ (thiosemicarbazide), —(C)NR$^1$NH$_2$ (carbonylhydrazide), —(C=S)NR$^1$NH$_2$ (thiocarbonylhydrazide), —(SO$_2$)NR$^1$NH$_2$ (sulfonylhydrazide), —NR$^1$NR$^2$(C)NR$^3$NH$_2$ (carbazide), —NR$^1$NR$^2$(C=S)NR$^3$NH$_2$ (thiocarbazide), or —O—NH$_2$ (hydroxylamine), where each R$^1$, R$^2$, and R$^3$ is independently H, or alkyl having 1-6 carbons, preferably H. In some cases, the reactive group is a hydrazide, hydroxylamine, carbohydrazide or a sulfonylhydrazide.

Reactive group chemistries used herein are not limited to those itemized above. By way of example, in other embodiments, the reaction between the first and second reactive groups can proceed via a dipolarophile reaction. For example, the first reactive group can be an azide and the second reactive group can be an alkyne. Alternatively, the first reactive group can be an alkyne and the second reactive group can be an azide. The unique reactivity of azide and alkyne functional groups can make them useful reactants for the selective coupling of polypeptides to arrays and other solid supports. Organic azides, particularly alphatic azides, and alkynes can be stable toward common reactive chemical conditions. Because the Huisgen cycloaddition reaction involves a selective cycloaddition reaction (see, e.g., Huisgen, in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains can permit the resultant polypeptides to be modified with extremely high selectivity. Both the azide and the alkyne functional groups can be inert toward the 20 common amino acids found in naturally-occurring polypeptides. When brought into close proximity, however, the "spring-loaded" nature of the azide and alkyne groups can be revealed and they can react selectively and efficiently via Huisgen [3+2] cycloaddition reaction to generate the corresponding triazole. See, e.g., Chin et al., Science 301:964-7 (2003); Wang et al., J. Am. Chem. Soc., 125, 3192-3193 (2003); Chin et al., J. Am. Chem. Soc., 124:9026-9027 (2002). Cycloaddition reaction involving azide or alkyne-containing polypeptides can be carried out at room temperature under aqueous conditions by the addition of Cu(II) (e.g., in the form of a catalytic amount of CuSO$_4$) in the presence of a reducing agent for reducing Cu(II) to Cu(I), in situ, in catalytic amount. See, e.g., Wang et al., J. Am. Chem. Soc. 125, 3192-3193 (2003); Tornoe et al., J. Org. Chem. 67:3057-3064 (2002); Rostovtsev, Angew. Chem. Int. Ed. 41:2596-2599 (2002). Reducing agents include, but are not limited to, ascorbate, metallic copper, quinine, hydroquinone, vitamin K, glutathione, cysteine, Fe$^{2+}$, Co$^{2+}$, and an applied electric potential.

Other reactive chemistries that can be used include, but are not limited to, the Staudinger ligation and the olefin metathesis chemistries (see, e.g., Mahal et al., (1997) Science 276:1125-1128).

In some embodiments, the attachment between the target binding moiety and the solid support is a non-covalent attachment. For example, the target binding moiety having suitable acidic groups will form strong associations with solid supports carrying hydroxyl or other negatively charged groups. In other variations of this system, other types of moieties having a strong affinity for each other can be incorporated into the reactive groups on the target binding moiety and the solid support. For example, a target binding moiety can be coupled with biotin through a suitable reactive group, while the solid support can be coated with avidin, resulting in a strong non-covalent binding between the target binding moiety and the solid support.

Alternative non-covalent coupling systems can be used.

Solid supports (e.g., arrays) suitable for use with the present disclosure are not limiting. It is not intended that the present disclosure be limited to any particular type of solid support material or array configuration.

Solid supports can be flat or planar, or can have substantially different conformations. For example, the solid support can exist as particles, beads, strands, precipitates, gels, sol-gels, sheets, tubing, spheres, containers, capillaries, pads, slices, films, plates, dipsticks, slides, etc. Magnetic beads or particles, such as magnetic latex beads and iron oxide particles, are examples of solid substrates that can be used in the methods of the present disclosure. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.). The solid support is chosen to maximize signal to noise ratios, primarily to minimize background binding, for ease of washing and cost. In addition, certain solid supports such as beads can easily be used in conventional fluid handling systems such as microwell plates.

Examples of the solid supports include glasses or other ceramics, plastics, polymers, metals, metalloids, alloys, composites, organics, etc. For instance, the solid supports can comprise a material selected from a group consisting of: silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for use as solid supports. In addition, many ceramics and polymers can also be used as solid supports. Polymers which can be used as solid supports include, but are not limited to, the following: polystyrene; poly(tetra)-fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyatkenesulfone (PAS); polypropylene; polyethylene; polyhydroxyethylmethacrylate (HEMA); polydimethyl-siloxane; polyacrylamide; polyimide; and block-copolymers. In some cases, substrates used for the array include silicon, silica, glass, and polymers. The solid support can be composed of a single material (e.g., glass), mixtures of materials (e.g., co-polymers) or multiple layers of different material (e.g., metal coated with a monolayer of small molecules, glass coated with a BSA, etc.).

The configuration of a solid support can be any appropriate form, e.g., can comprise beads, spheres, particles, granules, a gel, a sol-gel, a self-assembled monolayer (SAM) or a surface (which can be flat, or can have shaped features). The term "solid support" includes semisolid supports. Surfaces of the solid support can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection means including scanning by laser or other illumination and CCD, confocal or deflective light gathering.

For example, in some embodiments, solid supports can be in the form of slides. Slides can be made of any material. In some cases, the slide can comprise a plastic or glass matrix. Slides can be used to support a solid phase deposition of compounds (e.g., polypeptides) and can be prepared to contain very large numbers of addressable locations, for example, many thousands of locations. The process of placing a compound for analysis on a slide can be called "printing." Slide systems can utilize fluorescent dye labeling for the detection of interactions, and can be created using automated machinery that can deposit very small spots and place them quite close to one another with high precision. For example, spot diameters can be in the range of 100 microns, and it is possible to place 10,000-30,000 spots on a standard 1"×3" glass slide. Slide arrays may tend to have a large numbers and very high density of addressable coordinates.

In some embodiments, the slides or other solid supports can include self-assembled monolayers (SAMs), which can be formed as a result of affinity interactions and/or covalent bonding of SAM molecules at a surface interface. SAMs can assemble in a fashion similar to bilayer structures of soap bubbles or cell membranes, but with a single molecular layer forming at a solid interface. SAMs can be assembled from molecules with an interface binding group linked to terminal groups. SAMs can be assemblages of molecules such as, e.g., alkane thiols, silanes, fatty acids, or phosphonates. The driving force for assembly of a SAM can be an affinity interaction of the interface binding group with groups on the surface. A polarized alignment of the molecules on the surface can be further enhanced by interactions of the terminal groups with the external environment. The interactions driving assembly can be, e.g., hydrophobic interactions, hydrophilic interactions, ionic attractions, chelations, and the like.

In some embodiments, the solid support is in the form of a bead (synonymous with particle), which finds use, e.g., in liquid phase array systems (sometimes called bead arrays). These systems can employ a microwell plate (sometimes referred to as a "microtiter tray") having any number of wells that hold a liquid volume. Examples of microwell configurations include, but are not limited to, the 96 well plate, 384 well plate, and 1536 well plate. Each well can hold the particular components that are being used in the parallel analysis, for example, beads. A bead can be made of any substrate material, including biological, non-biological, organic, inorganic, polymer, metal, or a combination of any of these. The surface of the bead can be chemically modified and subject to any type of treatment or coatings, e.g., coatings that contain reactive groups that permit binding interactions with the target binding moieties.

In some embodiments, the beads can be produced in a way that facilitates their rapid isolation and/or purification. For example, magnetic beads can be manipulated by applying a magnetic field to rapidly isolate the beads from a liquid phase within a plate well.

In some embodiments, a solid support comprises or consists of a sol-gel. Sol-gel technologies are well known, and described, e.g., in Kirk-Othmer Encyclopedia of Chemical Technology third and fourth editions, esp. volume 20, Martin Grayson, Executive Editor, Wiley-Interscience, John Wiley and Sons, NY, e.g., at volume 22 and the references cited therein. Sols can be dispersions of colloidal particles (typically nanoscale elements) in a liquid such as water, or a solvent. Sol particles may be small enough to remain suspended in the liquid, e.g., by Brownian motion. Gels can be viscoelastic bodies that have interconnected pores of submicrometeric dimensions. Sol-gels can be used in the preparation of glass, ceramics, composites, plastics or the like by preparation of a sol, gelation of the sol and removal of the liquid suspending the sols. This process can be used in the many relatively low-temperature processes for the construction of fibers, films, aerogels, and the like (any of which can be the solid support in the present disclosure). In some embodiments, gelatination of a dispersion of colloidial particles is performed. In some embodiments, hydrolysis and polycondensation of alkoxide or metal salt precursors is performed. In some embodiments, hydrolysis and polycondensation of alkoxide precursors followed by aging and drying at room temperature is performed.

The surface of the solid support can be prepared to create suitable reactive groups to which linkers can be attached, or target binding moieties can be directly attached. Techniques for placing reactive groups such as those listed above on a substrate by mechanical, physical, electrical or chemical methods can be used (see, e.g., U.S. Pat. No. 4,681,870).

In addition to directly reacting chemical moieties on the target binding moieties and the solid support, other tethering mechanisms for connecting a polypeptide or polynucleotide to an array of the present disclosure can be used. Such tethering methods include: chemical tethering, biotin-mediated binding, cross-linking to the solid support matrix (e.g., UV, or florescence activated cross-linking) and the use of 'soluble' matrix, such as PEG, which can be precipitated by EtOH or other solvents to recover bound material (see also, Wentworth, P., 1999, Trends in Biotechnolgy 17:448452).

Sequencing

As described herein, in some embodiments, a target binding moiety is provided in solution for peptide identification. In some cases, the target binding moiety is linked to a coding moiety, wherein the coding moiety identifies or corresponds to the target binding moiety. The coding moiety can identify or correspond to the peptide sequence linked to the target binding moiety.

The peptide identification methods provided herein comprise contacting a mixture of antibodies with a plurality of target binding moieties, wherein each target binding moiety comprises a first peptide and a second peptide, wherein the first peptide and the second peptide are spaced by a spacer such that the first peptide and the second peptide bind to a single antibody molecule. In some embodiments, each target binding moiety of the plurality can be linked to a coding moiety. After contacting, the target binding moieties which are bound by antibodies can be captured. There are various ways to capture the target binding moieties bound by antibodies, for example, using immunoglobulin binding proteins.

The coding moieties linked to the target binding moieties that are captured can be amplified and subject to sequencing.

Various sequencing methods can be used in the present disclosure. In some embodiments, the method described herein employs next generation sequencing technology (NGS) in which clonally amplified DNA templates or single DNA molecules are sequenced in a massively parallel fashion within a flow cell (e.g., as described in Volkerding et al. Clin Chem 55:641-658 [2009]; Metzker M Nature Rev 11:31-46 [2010]). In addition to high-throughput sequence information, NGS can provide digital quantitative information, in that each sequence read is a countable "sequence tag" representing an individual clonal DNA template or a single DNA molecule. This quantification allows NGS to expand the digital PCR concept of counting cell-free DNA molecules (Fan et al., Proc Natl Acad Sci USA 105:16266-16271 [2008]; Chiu et al., Proc Natl Acad Sci USA 2008; 105:20458-20463 [2008]). The sequencing technologies of NGS include pyrosequencing, sequencing-by-synthesis with reversible dye terminators, sequencing by oligonucleotide probe ligation and real time sequencing.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the methods of the current disclosure and include the SMRT™ technology of Pacific Biosciences, the Ion Torrent™ technology, and nanopore sequencing (for example, by Oxford Nanopore Technologies). While the automated Sanger method is considered as a 'first generation' technology, Sanger sequencing including the automated Sanger sequencing, can also be employed by the methods of the current disclosure. Additional sequencing methods that comprise the use of developing nucleic acid imaging technologies, e.g., atomic force microscopy (AFM) or transmission electron microscopy (TEM), are also encompassed by the methods of the present disclosure.

In some embodiments, the method employs massively parallel sequencing of millions of DNA fragments using Illumina's sequencing-by-synthesis and reversible terminator-based sequencing chemistry (e.g., as described in Bentley et al., Nature 6:53-59 [2009]). Illumina's sequencing technology relies on the attachment of template DNA (e.g., a coding moiety or a portion thereof) to a planar, optically transparent surface on which oligonucleotide anchors are bound. Template DNA can be end-repaired to generate 5'-phosphorylated blunt ends, and the polymerase activity of Klenow fragment can be used to add a single A base to the 3' end of the blunt phosphorylated DNA template. This addition can prepare the DNA template for ligation to oligonucleotide adapters, which have an overhang of a single T base at their 3' end to increase ligation efficiency. The adapter oligonucleotides can be complementary to the flow-cell anchors. Under limiting-dilution conditions, adapter-modified, single-stranded template DNA can be added to the flow cell and immobilized by hybridization to the anchors. Attached DNA templates can be extended and bridge amplified to create an ultra-high density sequencing flow cell with hundreds of millions of clusters, each containing about 1,000 copies of the same template. In some embodiments, the coding moiety or a portion thereof is amplified using nucleic acid amplification (e.g., PCR) before it is subjected to cluster amplification. Alternatively, an amplification-free library preparation can be used, and the template DNA (e.g., the coding moiety or a portion thereof) can be enriched using the cluster amplification alone (Kozarewa et al., Nature Methods 6:291-295 [2009]). The templates can be sequenced using a four-color DNA sequencing-by-synthesis technology that employs reversible terminators with removable fluorescent dyes. High-sensitivity fluorescence identification can be achieved using laser excitation and total internal reflection optics. Sequencing reads can be analyzed using any available data analysis pipeline software. After completion of the first read, the templates can be regenerated in situ to enable a second read from the opposite end of the fragments. Thus, either single-end or paired-end sequencing of the DNA templates can be used according to the method.

The sequence of the coding moiety can be used to identify the sequence identity of the peptide sequence of the target binding moiety. In some embodiments, the coding moiety is a nucleic acid sequence which encodes a peptide sequence, and in such cases, the peptide sequence can be obtained by translating the nucleic acid sequence into amino acid sequence. In some embodiments, the coding moiety functions as a barcode but may not encode the peptide of the target binding moiety, and in such cases, each unique peptide sequence is pre-designed and is pre-assigned a unique nucleic acid sequence. For example, one can prepare a reference library of target binding moieties, each comprising a unique pre-designed peptide sequence, and each of the target binding moieties can be linked to a unique coding moiety with known sequence. After sequencing the coding moiety in a sample, the sequences can be used to identify the peptide sequences according to the reference library.

Subject and Disease

The compositions and methods provided herein can be used to identify or quantify a biomarker in a sample from a subject having a disease/condition. The biomarker can be an antibody or a fragment thereof. In some embodiments, a blood sample is obtained from a subject having a disease. In some embodiments, a serum sample is obtained from a subject having a disease. In some embodiments, a mixture of antibodies is obtained from a subject having a disease. In some embodiments, a mixture of antibodies is obtained from a healthy subject as a control. In some embodiments, the disease is a cancer. In some other embodiments, the disease is an autoimmune disease. In some embodiments, the disease is an infectious disease.

The term "subject" used herein can refer to an individual, a host, or a patient. In some embodiments, the subject is a human. In some embodiments, the subject is a mammal. In some other embodiments, the subject can be any animal subject, including laboratory animals, livestock, and household pets. The subject may be diagnosed or suspected of being at high risk for a disease. In some cases, the subject may not be necessarily diagnosed or suspected of being at high risk for the disease.

Subjects can be, for example, mammal, humans, pregnant women, elderly adults, adults, adolescents, pre-adolescents, children, toddlers, infants, newborn, or neonates. A subject can be a patient. In some cases, a subject can be a human. In some cases, a subject can be a child (i.e. a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be an obese or overweight subject.

Cancer can include both solid tumors and hematological malignancies. Cancers include, but are not limited to, gynecological cancers, ovarian cancer, cancer of the fallopian tube(s), peritoneal cancer, breast cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma). Cancers include, but are not limited to, ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof.

In addition, a subject provided herein may have a condition including benign or malignant tumors (e.g., adrenal, liver, kidney, bladder, breast, gastric, ovarian, colorectal, prostate, pancreatic, lung, thyroid, hepatic, cervical, endometrial, esophageal and uterine carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Preferably the "subject" or "patient" is a human although, as used herein, the terms are expressly held to comprise any mammalian species.

In some embodiments, a subject may have a neoplastic condition. A neoplastic condition may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterior unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In certain embodiments, a proliferative disorder comprises a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other embodiments, a disease is small cell lung cancer (SCLC) and non-small cell lung cancer (NSCLC) (e.g., squamous cell non-small cell lung cancer or squamous cell small cell lung cancer). In one embodiment, the lung cancer may be refractory, relapsed or resistant to a platinum based agent (e.g., carboplatin, cisplatin, oxaliplatin, topotecan) and/or a taxane (e.g., docetaxel, paclitaxel, larotaxel or cabazitaxel).

In some embodiments, a disease can be tumors with neuroendocrine features or phenotypes including neuroendocrine tumors. True or canonical neuroendocrine tumors (NETs) arising from the dispersed endocrine system are relatively rare, with an incidence of 2-5 per 100,000 people, but highly aggressive. Neuroendocrine tumors occur in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma).

With regard to hematologic malignancies, a disease can be B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas.

Examples of autoimmune diseases include, but are not limited to, Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticarial, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, Polyglandular syndromes type II, Polyglandular syndromes type III, Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, and Wegener's granulomatosis (or Granulomatosis with Polyangiitis (GPA)).

Examples of infectious diseases include, but are not limited to, Acute Flaccid Myelitis (AFM), Anaplasmosis, Anthrax, Babesiosis, Botulism, Brucellosis, *Burkholderia mallei* (Glanders), *Burkholderia pseudomallei* (Melioidosis), Campylobacteriosis (*Campylobacter*), Carbapenem-resistant Infection (CRE/CRPA), Chancroid, Chikungunya Virus Infection (Chikungunya), *Chlamydia*, Ciguatera, *Clostridium Difficile* Infection, *Clostridium Perfringens* (Epsilon Toxin), Coccidioidomycosis fungal infection (Valley fever), Creutzfeldt-Jacob Disease (transmissible spongiform encephalopathy, CJD), Cryptosporidiosis (Crypto), Cyclosporiasis, Dengue Fever, Diphtheria, *E. coli* infection (*E. coli*), Eastern Equine Encephalitis (EEE), Ebola Hemorrhagic Fever (Ebola), Ehrlichiosis, Encephalitis (Arboviral or parainfectious), Enterovirus Infection (Non-Polio Enterovirus), Enterovirus Infection D68 (EV-D68), Giardiasis (Giardia), Gonococcal Infection (Gonorrhea), Granuloma inguinale, *Haemophilus* Influenza disease (Type B Hib or H-flu), Hantavirus Pulmonary Syndrome (HPS), Hemolytic Uremic Syndrome (HUS), Hepatitis A (Hep A), Hepatitis B (Hep B), Hepatitis C (Hep C), Hepatitis D (Hep D), Hepatitis E (Hep E), Herpes, Herpes Zoster, zoster VZV (Shingles), Histoplasmosis infection (Histoplasmosis), Human Immunodeficiency Virus/AIDS (HIV/AIDS), Human Papillomarivus (HPV), Influenza (Flu), Lead Poisoning, Legionellosis (Legionnaires Disease), Leprosy (Hansens Disease), Leptospirosis, Listeriosis (*Listeria*), Lyme Disease, Lymphogranuloma venereum infection (LVG), Malaria, Measles, Meningitis (Meningitis, viral), Meningococcal Disease (Meningitis, bacterial), Middle East Respiratory Syndrome Coronavirus (MERS-CoV), Mumps, Norovirus, Paralytic Shellfish Poisoning (Paralytic Shellfish Poisoning, Ciguatera), Pediculosis (Lice, Head and Body Lice), Pelvic Inflammatory Disease (PID), Pertussis (Whooping Cough), Plague (Bubonic, Septicemic, Pneumonic), Pneumococcal Disease (Pneumonia), Poliomyelitis (Polio), Powassan, Psittacosis, Pthiriasis (Crabs; Pubic Lice Infestation), Pustular Rash diseases (Small pox, monkeypox, cowpox), Q-Fever, Rabies, Ricin Poisoning, Rickettsiosis (Rocky Mountain Spotted Fever), Rubella (German Measles), *Salmonellosis* gastroenteritis (*Salmonella*), Scabies Infestation (Scabies), Scombroid, Severe Acute Respiratory Syndrome (SARS), Shigellosis gastroenteritis (*Shigella*), Smallpox, Staphyloccal Infection Methicillin-resistant (MRSA), Staphylococcal Food Poisoning (Staph Food Poisoning), Staphylococcal Infection Vancomycin Intermediate (VISA), Staphylococcal Infection Vancomycin Resistant (VRSA), Streptococcal Disease Group A (Strep A), Streptococcal Disease Group B (Strep-B), Streptococcal Toxic-Shock Syndrome (STSS, TSS), Syphilis (primary, secondary, early latent, late latent, or congenital), Tetanus Infection (Lock Jaw), Trichonosis Infection (Trichinosis), Tuberculosis (TB), Tuberculosis (Latent) (LTBI), Tularemia (Rabbit fever), Typhoid Fever, Typhus, Vaginosis (Yeast Infection), Varicella (Chickenpox), *Vibrio cholerae* (Cholera), Vibriosis (*Vibrio*), Viral Hemorrhagic Fever (Ebola, Lassa, Marburg), West Nile Virus, Yellow Fever, Yersenia (*Yersinia*), and Zika Virus Infection (Zika).

Kits

The current disclosure is also directed to compositions and kit or reagent systems useful for practicing the methods described herein.

The compositions of the current disclosure can be provided in kits for peptide/peptoid identification. In case of in solution identification, the kits can further comprise reagents useful for amplification and/or sequencing, for example, primers and buffers. In case of on array identification, one or more arrays can be provided in a kit. The array provided in the kit can comprise the target binding moieties described herein. The kit can comprise one or more target binding moieties described herein. The kit can comprise one or more polynucleotide-barcoded target binding moieties. The kit may comprise one or more components for a user to make a target binding moieties or a polynuclotide-barcoded target binding moiety. The kit can comprise a target binding unit. The kit can also comprise an additional reagent for a user to use the target binding moieties for analyte identification. The one or more reagents in a kit can be provided in one or more containers. In some cases, one or more reagents may be provided in a mixture.

The compositions of the current disclosed can be provided in kits for antibody profiling. In such cases, a kit can comprise a panel of specific peptide sequences that are known to be able to differentiate a sample from a patient and a sample from a healthy subject.

Kits can contain a reagent combination including the elements needed to conduct an assay according to the methods disclosed herein. The reagent system can be presented in a commercially packaged form, as a composition or admixture where the compatibility of the reagents will allow, in a test device configuration, or as a test kit. The kit can comprise a packaged combination of one or more containers, devices, or the like holding the necessary reagents. The kit can include written instructions for the performance of an assay or assays. The kit of the present disclosure may be adapted for any configuration of assay and may include compositions for performing any of the various assay formats described herein. Kits can comprise compositions including primer sets for amplifying a nucleic acid sequence of the coding moiety as described and, where applicable, reagents for purifying target binding moiety bound with antibodies, or reagents for purifying blood samples. The kit can include a plurality of primer sets to amplify a plurality of sequences. A kit can comprise other reagents and/or information for peptide identification in solution or on array and/or antibody profiling in a sample (e.g., buffers, nucleotides, instructions). The kits can also include a plurality of containers of appropriate buffers and reagents.

DETAILED DESCRIPTION OF FIGURES

FIG. 1 illustrates two example configurations of target binding moiety described in the present disclosure. As illustrated in (a), the target binding moiety can have a branched chain or configuration. As illustrated in (b), the target binding moiety can have a linear chain or configuration. In both configurations, the target binding moiety comprises one or more target binding units, or two or more binding elements. In configuration (a), the main chain used to link the binding elements is a scaffold. In configuration (b), the scaffold and the binding elements are comprised in the same chain. Two binding elements are separated by a spacer and are spaced such that they can simultaneously bind to a single molecule comprising an antigen binding domain of an antibody.

Figure 2:
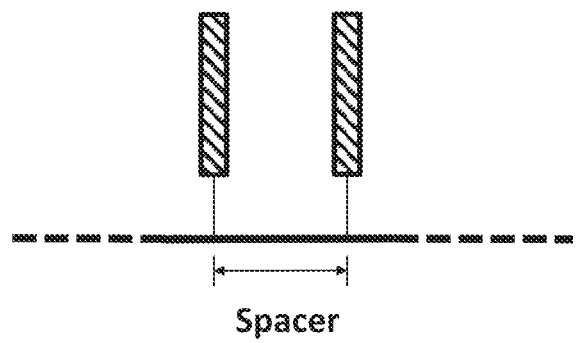
FIG. 2 illustrates example structures of a target binding unit described herein.
Figure 2:

FIG. 2 illustrates two examples configurations of target binding unit. A target binding unit can be the smallest unit for target binding. A target binding unit comprises two binding elements (e.g., peptides or peptoids).

Figure 3:
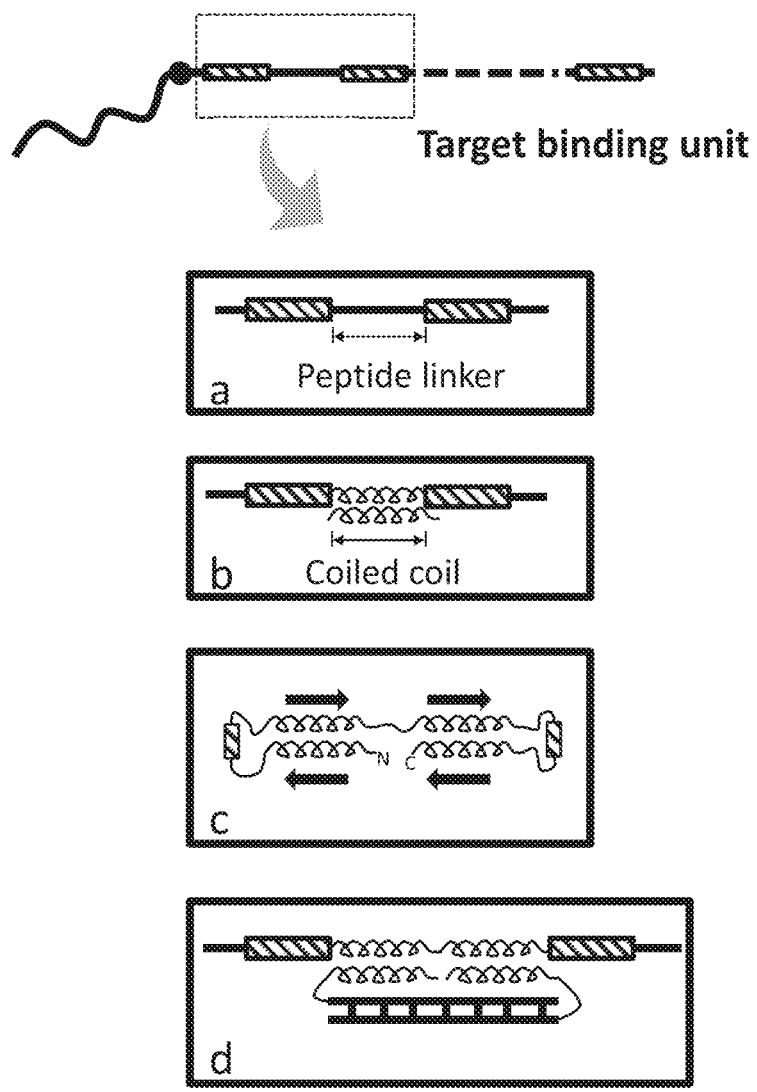
FIG. 3 illustrates example structures of a spacer described herein.

FIG. 3 illustrates four example structures of the spacer. As illustrated in (a), the spacer is an unstructured peptide. As illustrated in (b), the spacer comprises two peptides stands folded into alpha-helices, and the two peptide strands further interact to form a coiled coil structure. As illustrated in (c), the spacer comprises two coiled coil structures, and in this cases, the two coiled coil structured are folded by different regions of a single peptide chain. As illustrated in (d), the spacer comprises a coiled coil structure formed by three peptide strands including one longer peptide strand and two shorter peptide strands. The two shorter peptide strands can further be linked to two opposite ends of a double-stranded polynucleotide.

Figure 4:
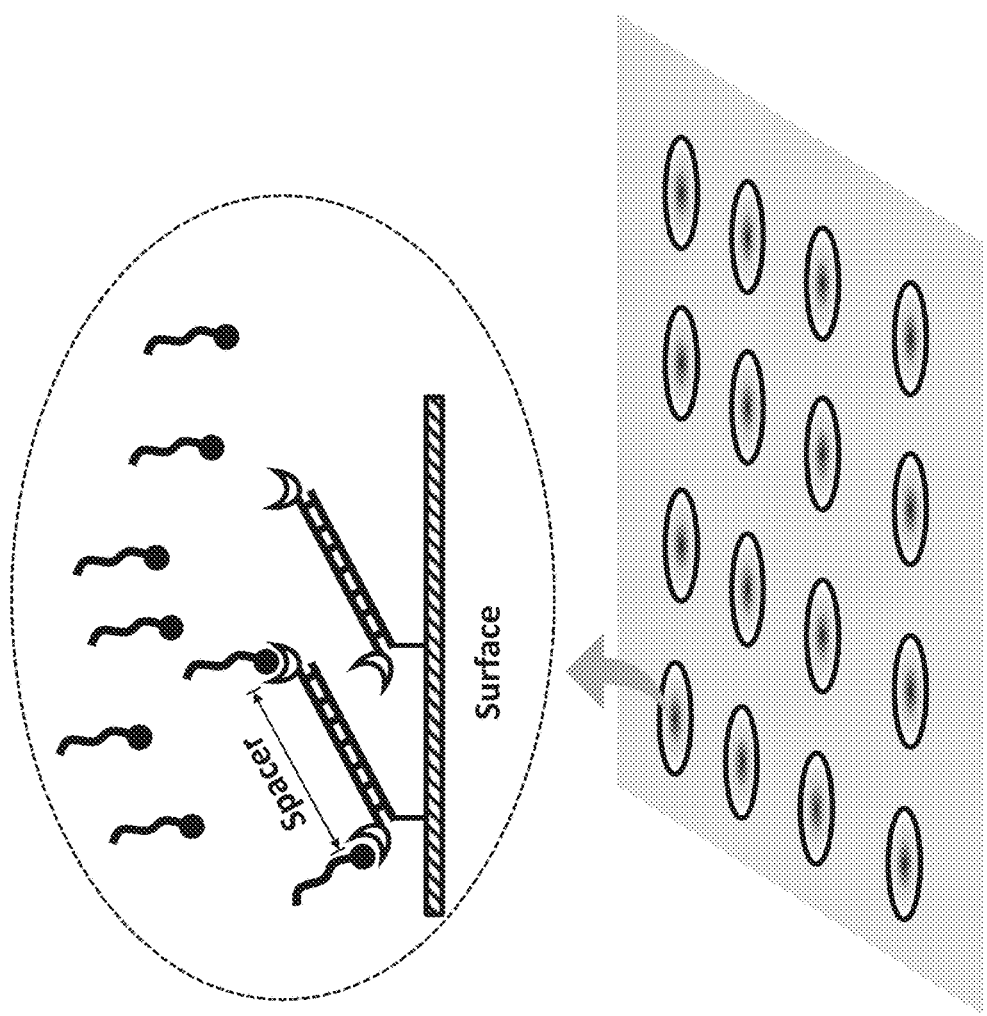
FIG. 4 illustrates an example of an array having different discrete regions and an example structure of a scaffold immobilized on a discrete region of the array.

FIG. 4 illustrates an example of an array having many discrete regions. Each discrete region has one or more copies of a unique type of target binding moieties attached thereto. For example, the one or more copies of the target binding moieties have a same sequence of the target binding regions, or have a same sequence of the binding elements. In this example, the spacer is a double-stranded polynucleotide.

Figure 5A:
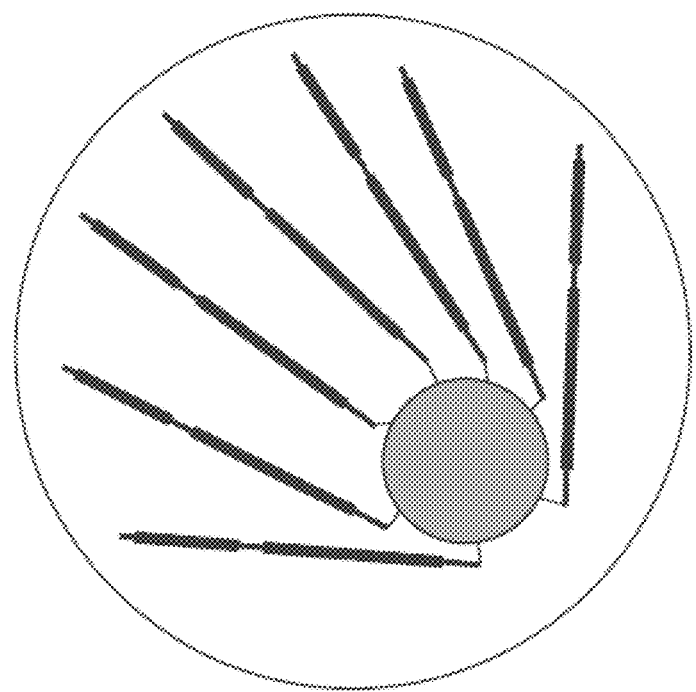
FIG. 5A illustrates an example embodiment for generating polynucleotide-barcoded target binding moieties using in vitro compartmentalization.
Figure 5B:
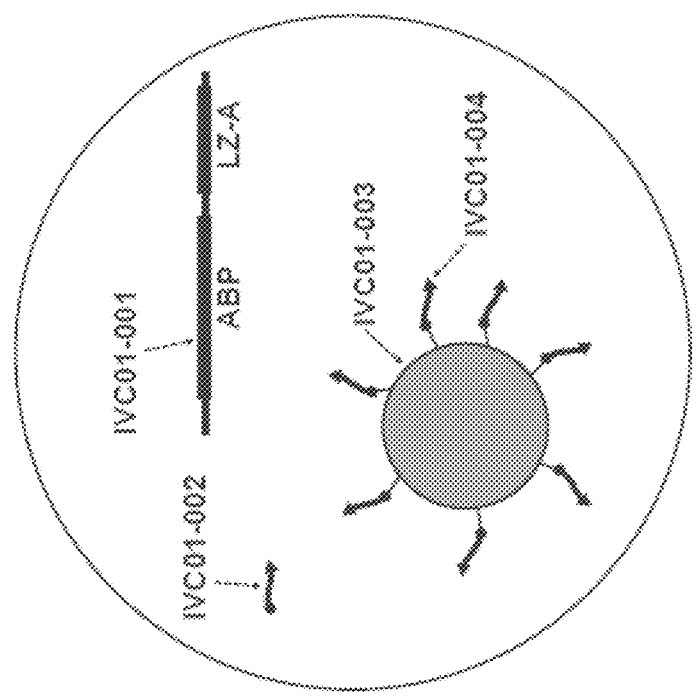
FIG. 5B illustrates an example embodiment for generating polynucleotide-barcoded target binding moieties using in vitro compartmentalization.
Figure 5C:
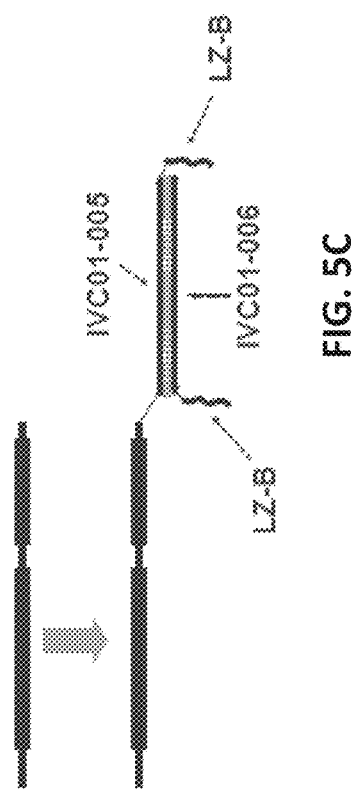
FIG. 5C illustrates an example embodiment for generating polynucleotide-barcoded target binding moieties using in vitro compartmentalization.

FIGS. 5A-C illustrate an example scheme of generating a polynucleotide-barcoded target binding moiety by in vitro compartmentalization. As illustrated in FIG. 5A, a coding moiety (IVC01-001) can be compartmentalized in a droplet with a first soluble primer and a bead having multiple copies of a second primers in order to generate clonal copies of the coding moiety. The coding moiety can encode for binding element and a peptide linker which can fold into an alpha-helix (LZ-A). As illustrated in FIG. 5B, multiple clonal copies of the coding moiety are attached to the bead. As illustrated in FIG. 5C, each clonal copy of the coding moiety is linked to a scaffold having an alpha-helix (LZ-B) linked on each end of the scaffold. LZ-A and LZ-B can interact to form a leucine zipper. For more details, see Example 6.

Figure 6B:
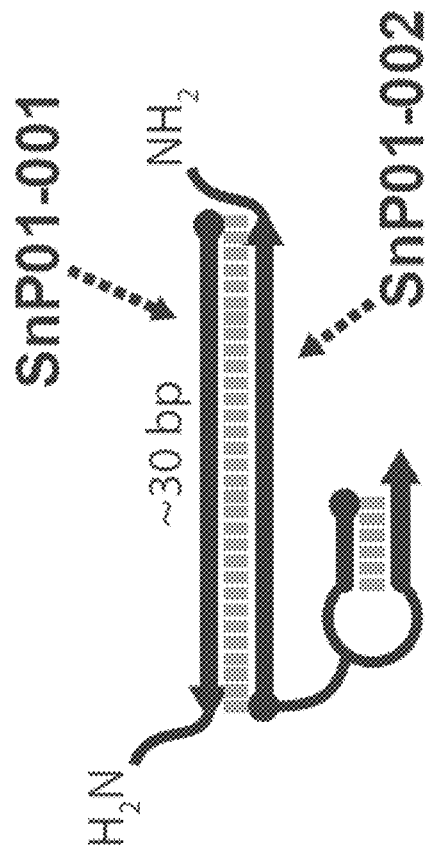
FIG. 6B illustrates an example structure used for generating polynucleotide-barcoded target binding moieties by split-and-pool synthesis.
Figure 6A:
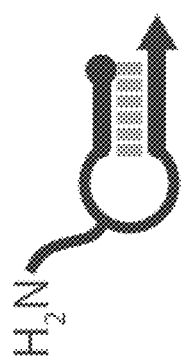
FIG. 6A illustrates an example structure used for generating polynucleotide-barcoded binding elements by split-and-pool synthesis.
Figure 7A:
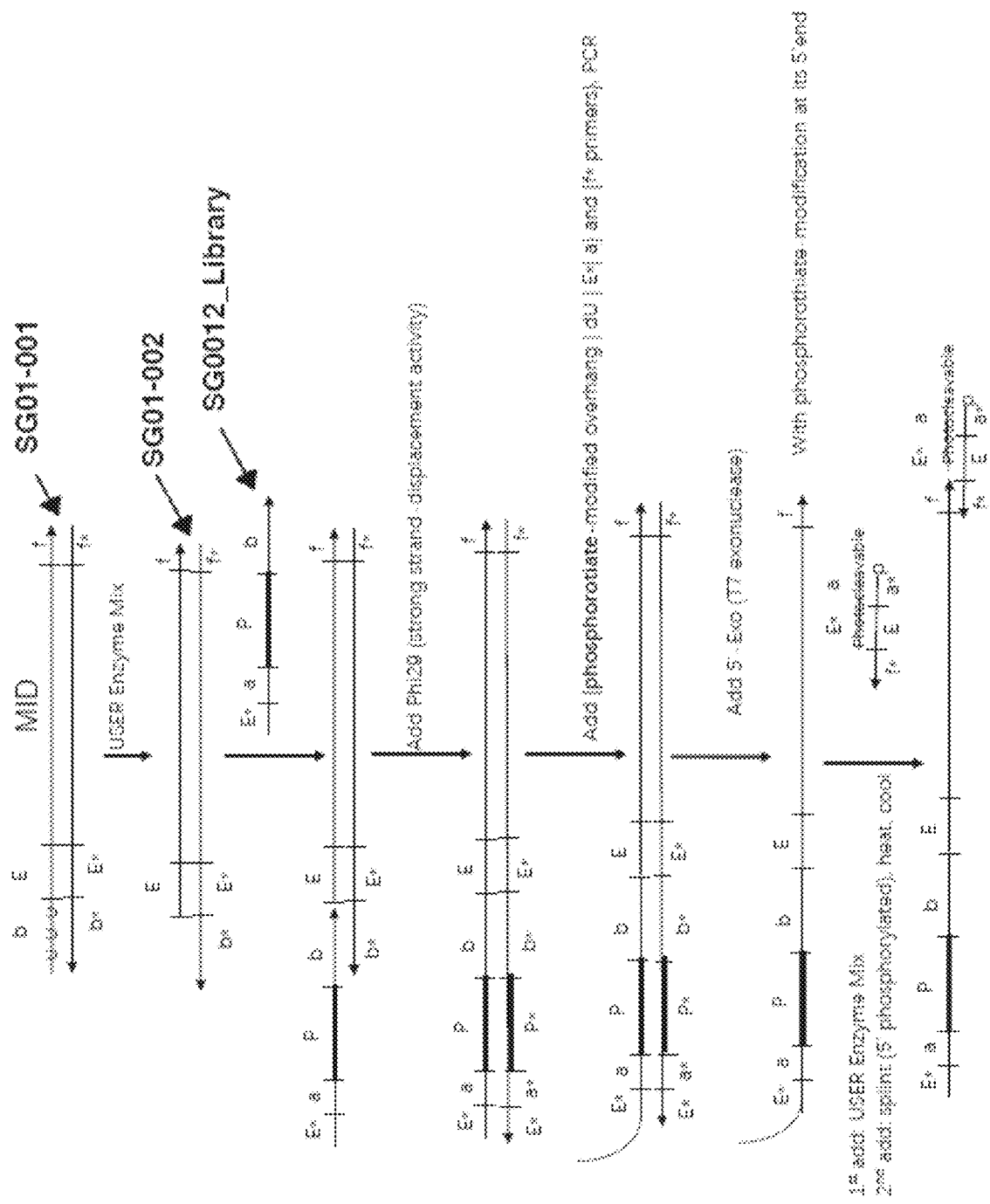
FIG. 7A illustrates an example scheme of generating a library of target binding moieties.
Figure 7B:
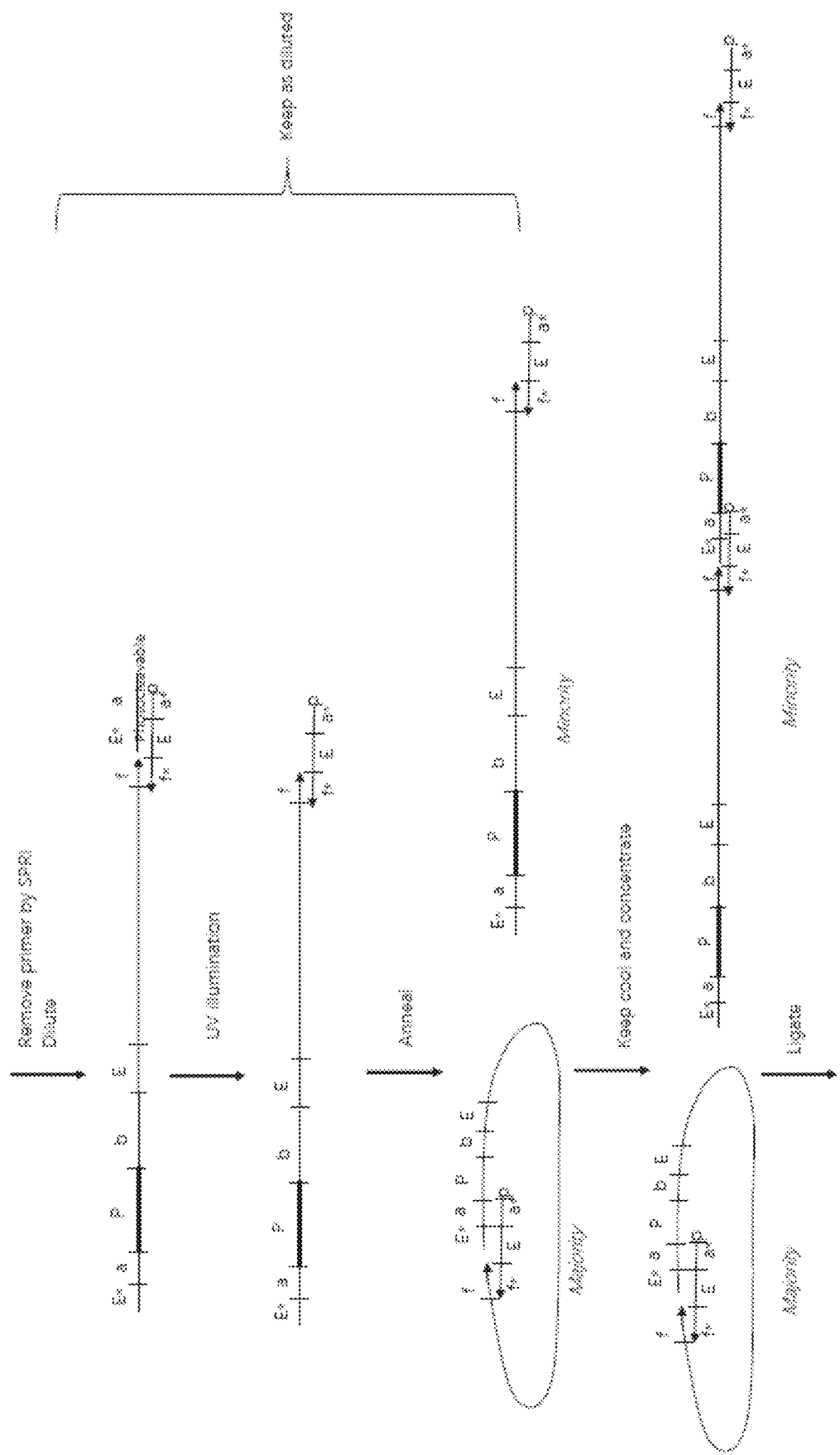
FIG. 7B illustrates an example scheme of generating a library of target binding moieties.
Figure 7C:
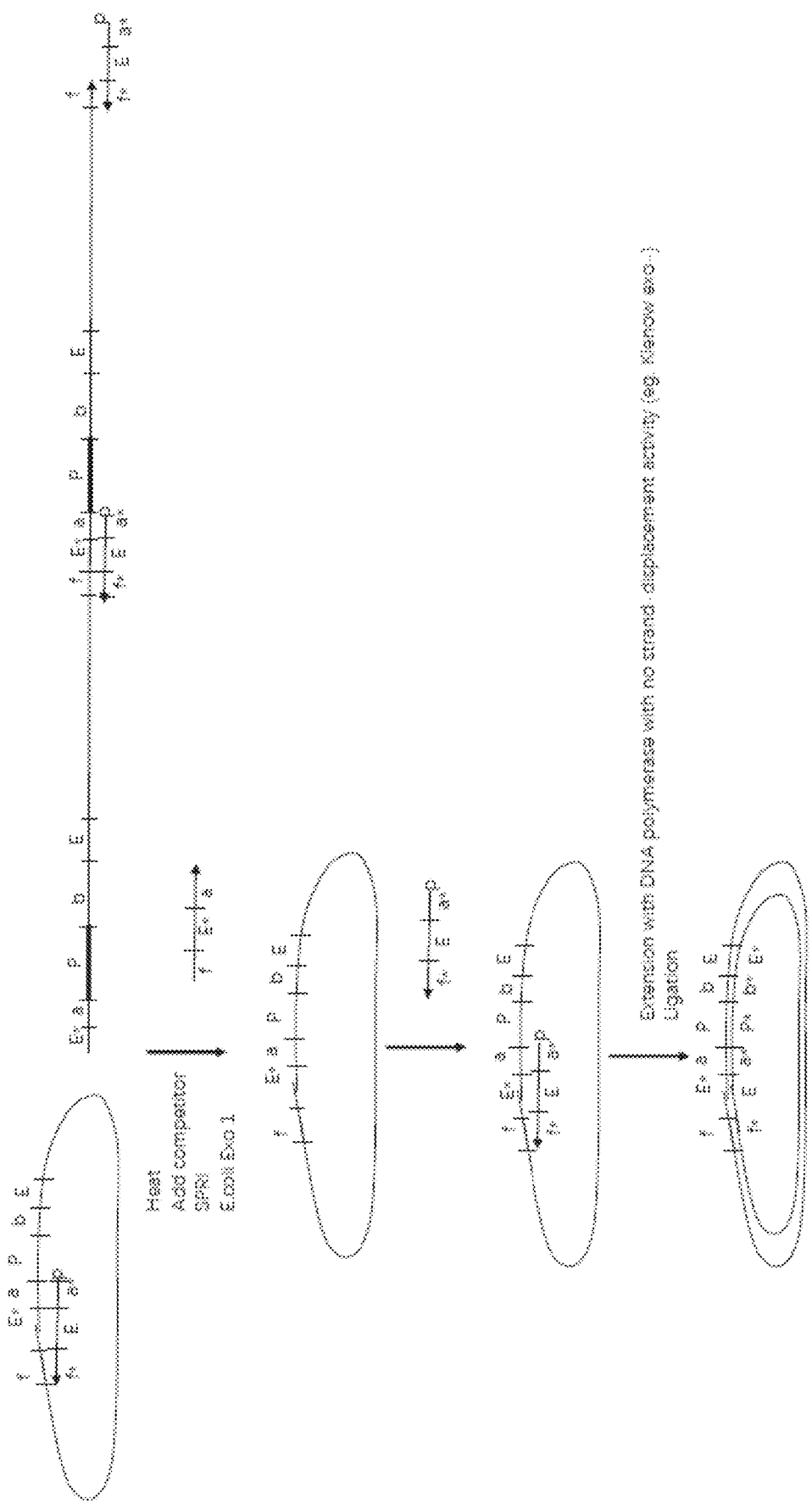
FIG. 7C illustrates an example scheme of generating a library of target binding moieties.
Figure 7D:
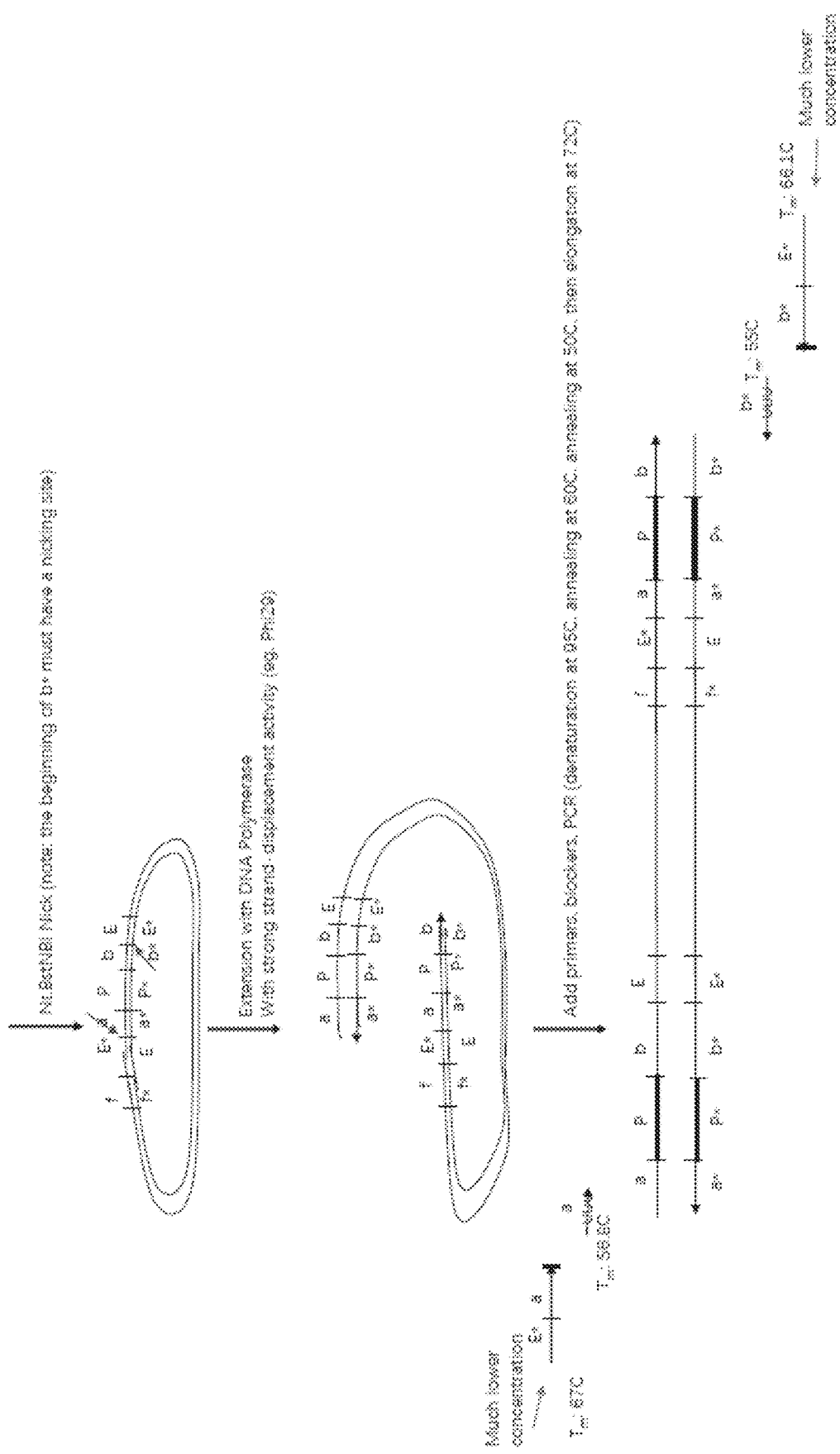
FIG. 7D illustrates an example scheme of generating a library of target binding moieties.
Figure 7E:
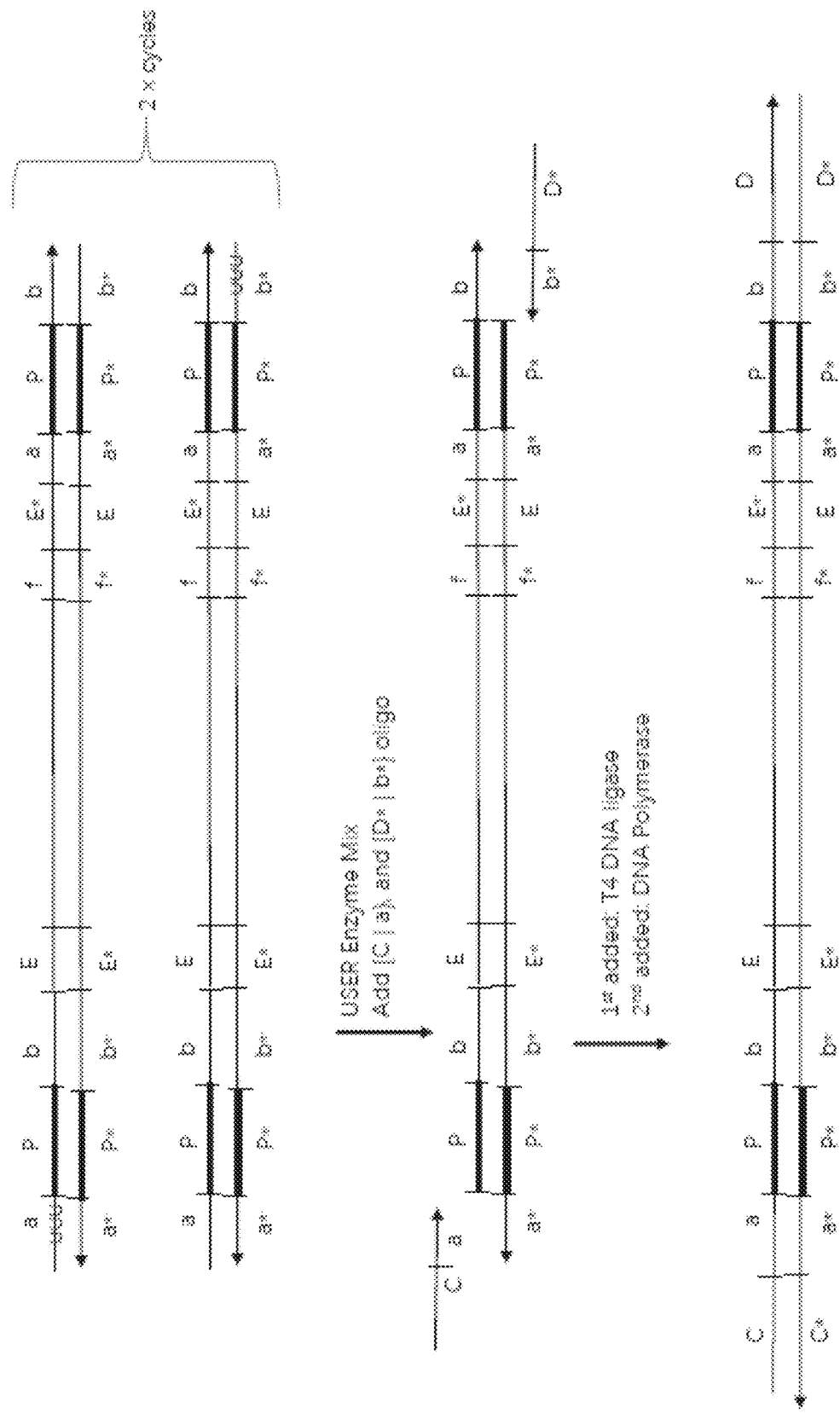
FIG. 7E illustrates an example scheme of generating a library of target binding moieties.

FIGS. 6A-B illustrate example structures that can be used to generate polynucleotide-barcoded binding element by split-and-pool synthesis. As illustrated in FIG. 6A, a structure known in the art can be used to generate polynucleotide-barcoded chemical library. For example, the DNA can be synthesized from the 3' end (as indicated by arrow), and the chemical building blocks can be synthesized from the free $NH_2$ group. As illustrated in FIG. 6B, a structure designed in the present disclosure having two free $NH_2$ groups can be used to generate polynucleotide-barcoded chemical library having two identical binding elements. Such polynucleotide-barcoded chemical library includes a library of polynucleotide-barcoded target binding moieties.

FIGS. 7A-E illustrate an example experimental procedure to generate a library of target binding moieties (e.g., as described in Example 3 for generating a library of HOPs).

Figure 8A:
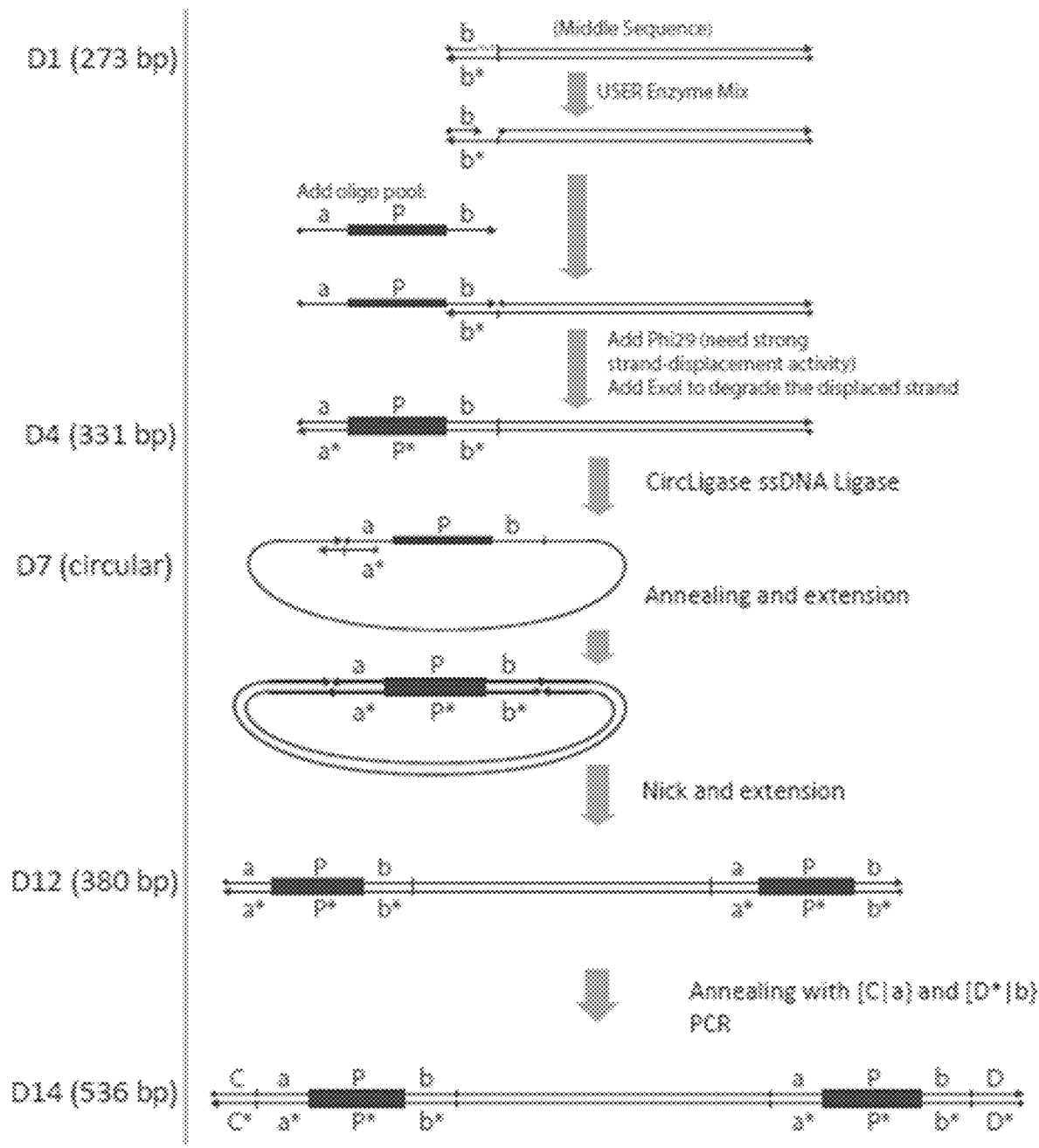
FIG. 8A illustrates an example scheme of generating a library of target binding moieties.

FIG. 8A illustrates an example experimental procedure to generate a library of target binding moieties (e.g., as described in Example 11 for generating a library of HOPs and PEHOPs).

Figure 8B:
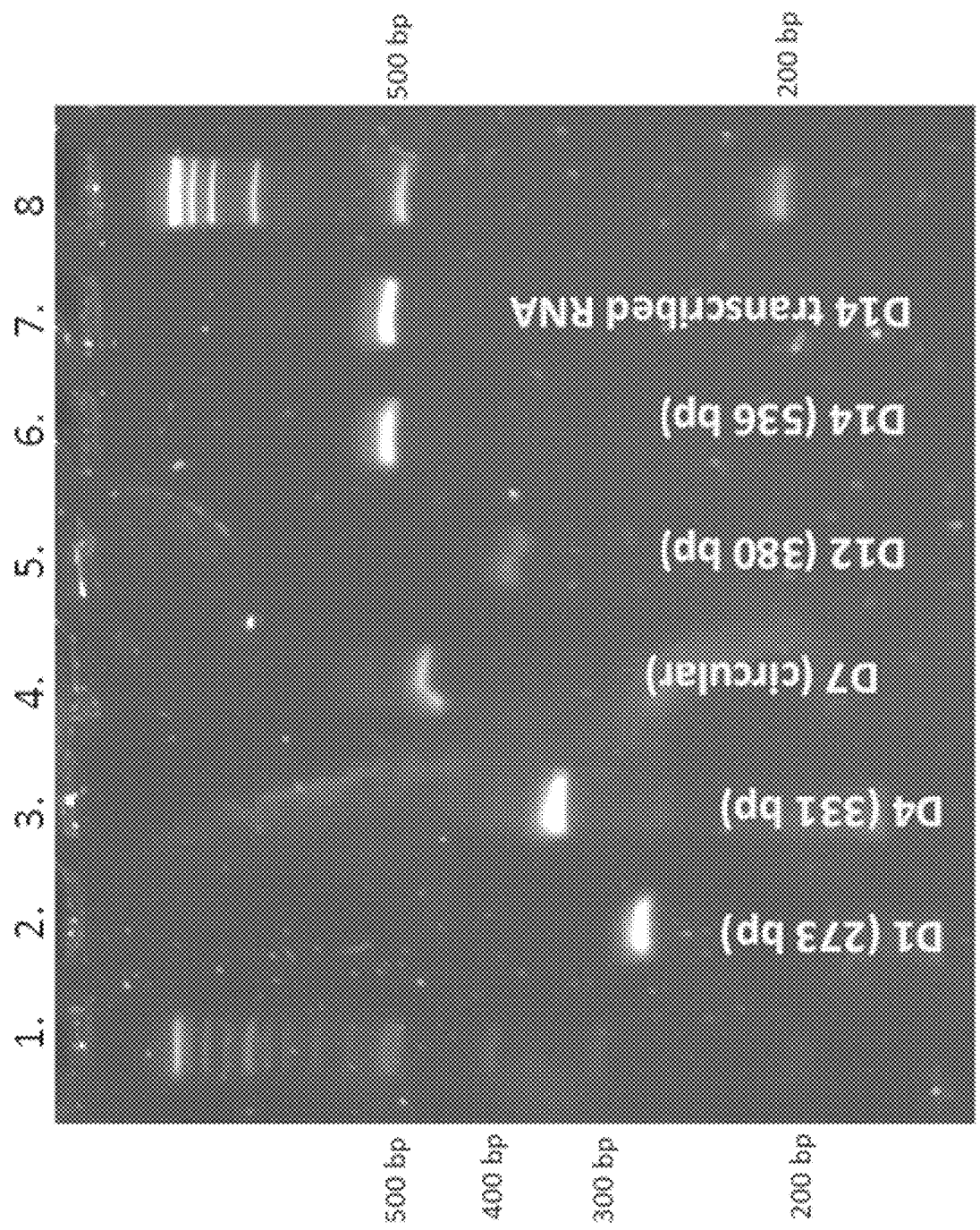
FIG. 8B illustrates a denaturing polyacrylamide gel image showing the presence of products with the desired size generated during different steps of the example scheme illustrated in FIG. 8A (e.g., D1, D4, D7, D12, and D14).

FIG. 8B shows an experimental gel image of products generated during different steps of the procedure shown in FIG. 8A and proves that a library of nucleic acid templates of the desired size (536 bp) can be made using the described procedure in FIG. 8A. The nucleic acid templates are DNAs which can be further transcribed into RNAs to be used to generate a library of PEHOPs.

Figure 9:
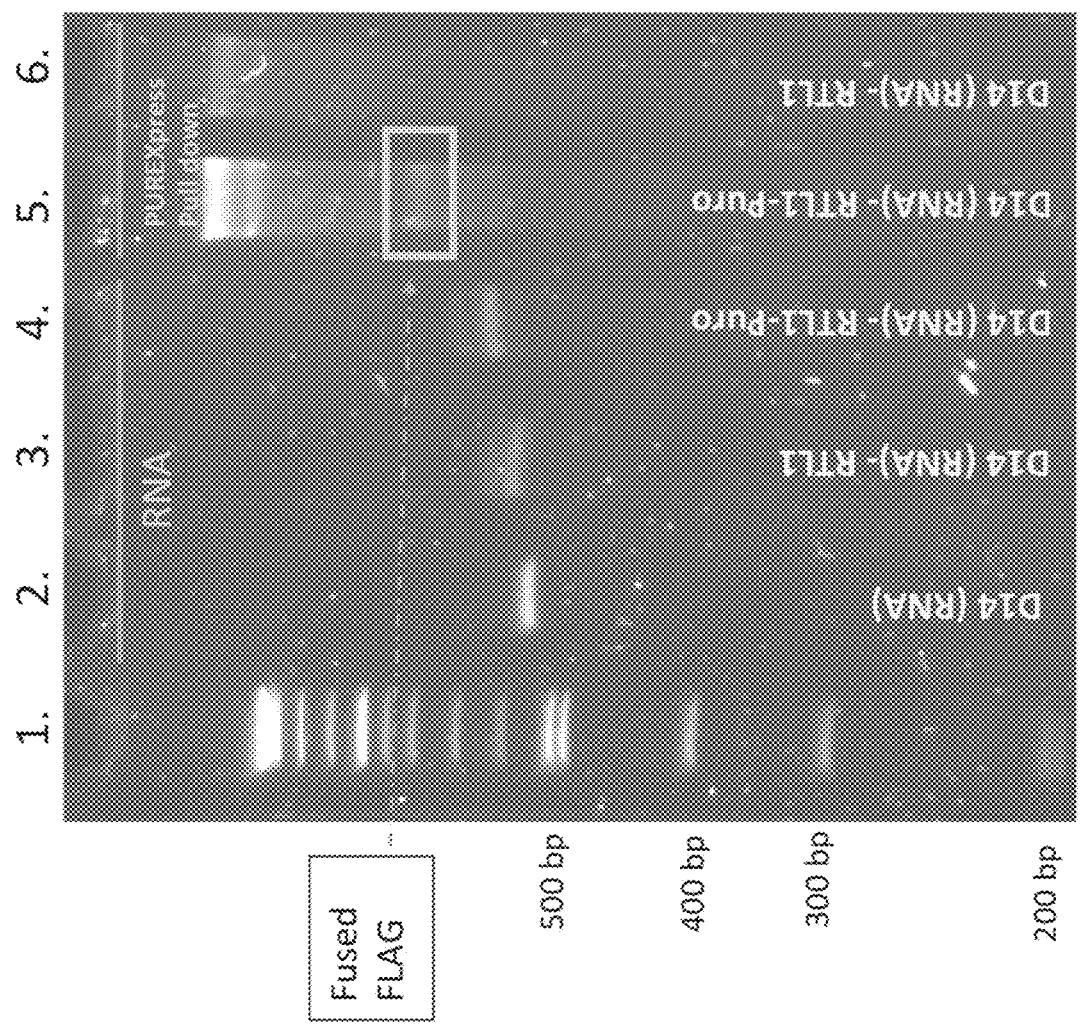
FIG. 9 illustrates a denaturing polyacrylamide gel image showing the presence of products with the desired size generated by further treating the DNA product of D14 (536 bp) to make RNA-peptide fusion molecules during different steps of RNA display.

FIG. 9 illustrates a denaturing polyacrylamide gel image showing the presence of products with the desired size generated by further treating the DNA product of D14 (536 bp) to make RNA-peptide fusion molecules during different steps of RNA display as described in Example 11.

Figure 10A:
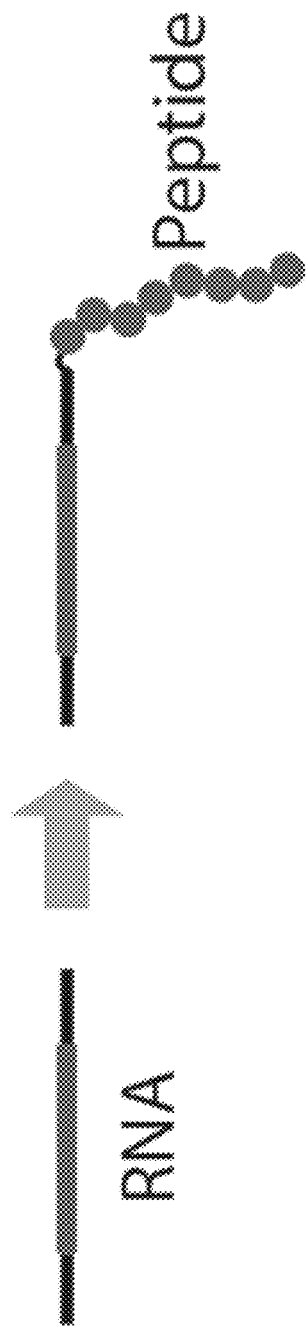
FIG. 10A illustrates a schematic of using RNA display to generate a polynucleotide-peptide fusion molecule.

FIG. 10A illustrates a schematic of using RNA display to generate a polynucleotide-peptide fusion molecule.

Figure 10B:
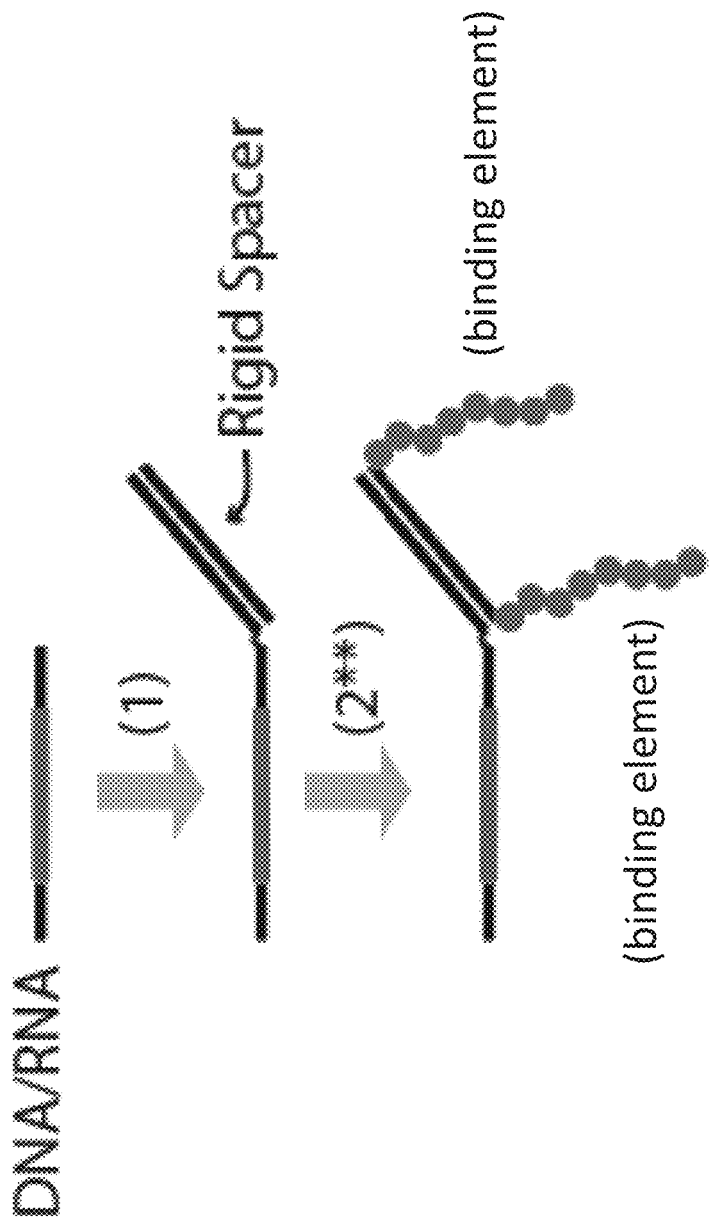
FIG. 10B illustrates an example of polynucleotide-barcoded target binding moiety.

FIG. 10B illustrates an example of polynucleotide-barcoded target binding moiety. A DNA or RNA template can be linked to a rigid spacer. Various spacer described in the present disclosure can be used, for example, a double stranded DNA or a coiled coil formed by two peptide chains. The two ends of the rigid spacer can be further linked to two binding elements (e.g., peptides). The binding elements can be encoded by the DNA or RNA template.

Figure 10C:
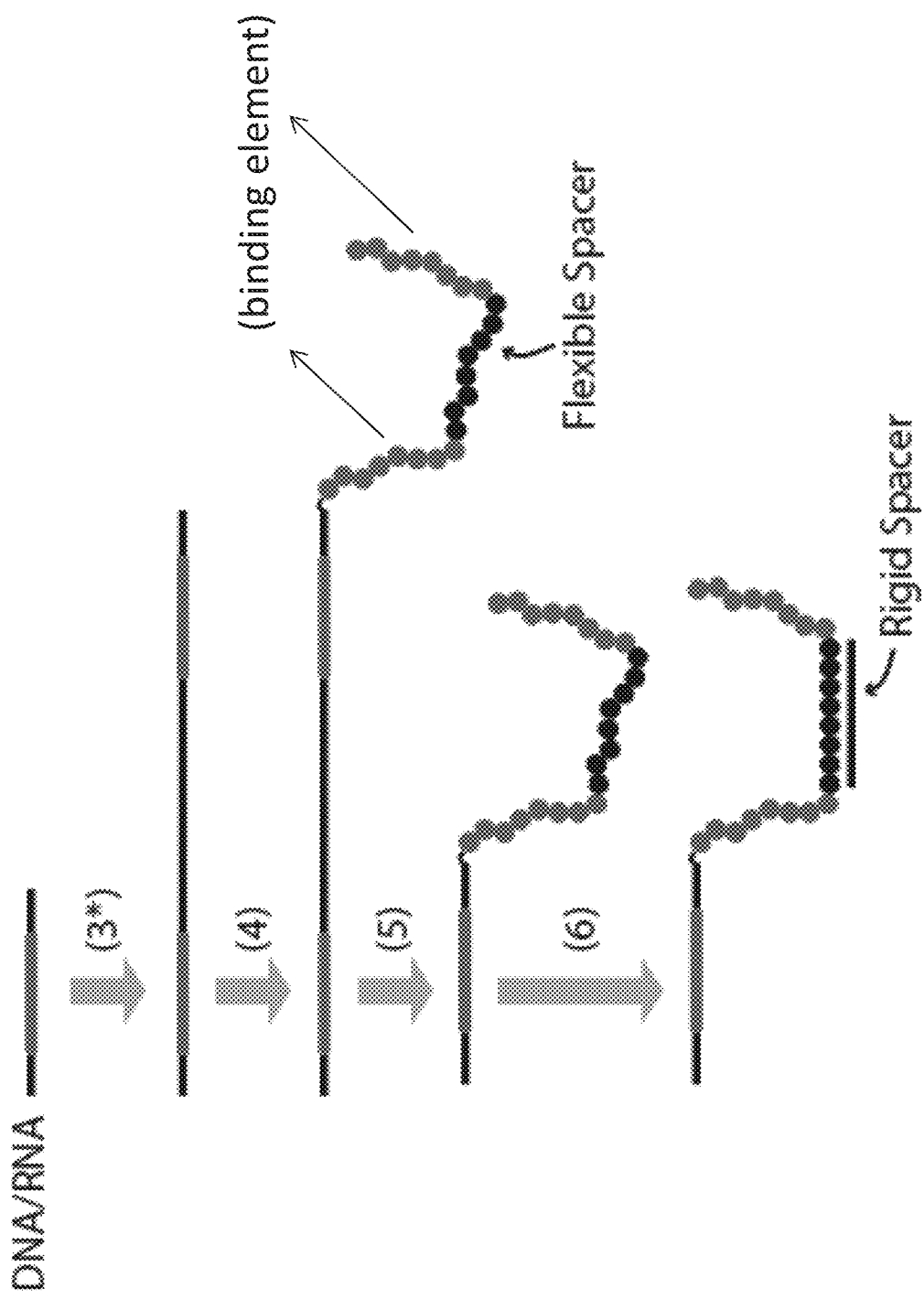
FIG. 10C illustrates an example of polynucleotide-barcoded target binding moiety with a flexible spacer which can be further manipulated to generate a rigid spacer.

FIG. 10C illustrates an example of polynucleotide-barcoded target binding moiety with a flexible spacer which can be further manipulated to generate a rigid spacer. A DNA or RNA template encoding a unique binding element sequence can be fused to an additional DNA or RNA template encoding the same unique binding element sequence (step 3*). The fused template can be used to generate a polynucleotide-peptide fusion molecule (e.g. a polynucleotide-barcoded target binding moiety) in step (4) using RNA display. The polynucleotide-peptide fusion molecule comprises a peptide flexible spacer. The peptide flexible spacer can be manipulated to become a rigid spacer, for example, by adding an additional peptide chain to form a coiled coil structure with the peptide flexible spacer.

EXAMPLES

Example 1: Design of Target Binding Moieties

Here we describe a series of methods to make and use target binding moieties and/or polynucleotide-barcoded target binding moieties, as well as other related molecular structures, to profile analytes (e.g., antibodies) in a sample. To simplify the descriptions in the "Examples" section, "PIRM" is used as an example of "binding element", "HOP" is used as an example of a target binding moiety having at least two binding elements linked by a spacer, "PEHOP" is used as an example of polynucleotide-barcoded target binding moiety. Therefore, as described in the "Examples" section, the PIRMs can be assembled into soluble oligomers which we call homo-oligomeric PIRMs (HOPs). In each HOP, multiple PIRMs (often all the PIRMs) can bind the same immunoreceptor (e.g., an antigen binding domain of an antibody). In some embodiments, 2 PIRMs in a HOP can bind the 2 identical Fab domains of the same antibody molecule. In some embodiments, all the PIRMs in a HOP have the same structure. When a HOP is stably associated with a polynucleotide (e.g., DNA or RNA) whose sequence reflects the sequence of the PIRM, the resulting molecule is called a polynucleotide-barcoded HOP (PEHOP). Branched (PE)HOP versus Linear (PE)HOP The HOP may adopt a branched configuration or a linear configuration. In the branched configuration, there is a soluble scaffold molecule which comprises multiple attachment sites for PIRMs. In some embodiments, the scaffold is a high molecular-weight polymer or a dendrimer. In the linear configuration, the spacers and the PIRMs can be parts of one continuous linear polymer. In the situation when both the PIRMs and the spacers are polypeptide, the continuous linear polymer can be a continuous linear polypeptide.
Unfolded PIRMs and Folded PIRMs The PIRM can be unfolded. For example, when short (e.g., <40-aa) peptide with randomly generated sequence is used as the PIRM, the PIRM is likely to be unfolded, unstructured and flexible. Alternatively, the PIRM may be folded and structured. For example, an antibody domain (e.g., a single-chain Fv or a $V_H$ domain) may be a PIRM. Other protein types commonly used to engineer affinity reagents such as DARPins, Affibodies, Affinitins may also serve as PIRMs.
Peptide-Based PIRMs May Contain Unnatural Amino Acid Site-specific incorporation of unnatural amino acids into peptides and proteins using in vitro translation system including RNA display can be used to make PIRM containing at least one unnatural amino acid.
Domain-Level Description of Polynucleotide Sequences In the "Examples" section, sometimes the polynucleotide sequence is described at domain level. Each domain name corresponds to a specific polynucleotide sequence. For example, domain 'A' may have a sequence of 5'-TATTCCC-3', domain 'B' may have a sequence of 5'-AGGGAC-3', and domain 'C' may have a sequence of 5'-GGGAAGA-3'. In this case, the polynucleotide having a sequence that is the concatenation of domains A, B, and C, can be written as [A|B|C}. The symbol denotes the 5' end, the symbol '}' denotes the 3' end, and the symbol '|' separates domain names. An asterisk sign shows sequence complementarity. For example domain 'B*' is the reverse complement of domain 13'.

Example 2: Make an Individual PEHOP Species Using RNA Display (Linear, Dimeric)

This example shows how to make a PEHOP with two copies of antibody-binding peptide sequences using RNA display.

Step A: A DNA template, named gBlock01, that encodes the HOP can be prepared by standard DNA synthesis and gene assembly. gBlock01 will contain the sequences for T7 promoter, ribosome binding site, and the coding sequence for a HOP (including an amino acid spacer and two copies of peptide-based PRIM). The spacer will have the sequence of CC—B which can form a coiled coil with peptide CC-A. gBlock01 can be obtained commercially, such as from Integrated DNA Technology in the form of gBlock.

Step B: gBlock01 can be amplified using conventional PCR. The product of such PCR can be examined with running 1% agarose gel electrophoresis.

Step C: The PCR product can be purified by Agencourt AMPure XP beads.

Step D: In vitro transcription can be performed to synthesize high yield of mRNA transcripts by using T7 RNA Polymerase (such as Hiscribe T7 High Yield RNA synthesis kit, NEB #E2040S).

Step E: The mRNA transcript can be further purified by Agencourt AMPure XP beads. The concentration of purified RNA can be obtained by UV absorbance at 260 nm.

Step F: To attach a puromycin moiety to the 3' end of the mRNA, an adaptor can be used. The adaptor can be formed by reacting a modified oligonucleotide named RTL1 and a modified oligonucleotide named DBCO.F.Puro (see Table 1 for sequences) to form RTL1-DBCO.F.Puro. For example, 100 µM RTL1 and 100 µM DBCO can be mixed with 1:1 ratio. The conjugation reaction can be performed at 37° C. for overnight.

Step G: The RTL1-DBCO.F.Puro adaptor can later be purified by gel extraction methods. Specifically, the conjugation reaction product can be resolved on 15% polyacrylamide gel with 7 M Urea, and the band containing the conjugated RTL1-DBCO.F.Puro can be excised from gel and frozen at −80° C. for 20 min. Later, the sample can be centrifuged at 15,000 g for 10 min. The supernatant can be taken out and further purified using micro-spin G25 column (GE27-5325-01 SIGMA).

Step H: The purified RTL1-DBCO.F.Puro can be mixed with the purified mRNA transcripts prepared above using at a ratio of 3:1 at 55° C. for 5 min for efficient annealing.

Step I: Following annealing reaction, a ligation reaction between RTL1-DBCO.F.Puro and the mRNA transcripts can be performed using T4 RNA ligase 1 (NEB #M0204S) at 37° C. for 1 h. The product of this ligation can be named mRNA-RTL1-DBCO.F.Puro.

Step J: The ligation reaction can be further purified by Agencourt AMPure XP to remove RTL1-DBCO.F.Puro that is not hybridized to the mRNA transcript. The concentration of purified mRNA-RTL1-DBCO.F.Puro can be obtained from UV absorbance at 260 nm.

Step K: The mRNA-RTL1-DBCO.F.Puro can be in vitro translated by using PURExpress in vitro protein synthesis kit (NEB #6800) to form mRNA-peptide conjugate. Specifically, 10 µL Solution A, 7.5 µL solution B, 1 µL RnaseOut Recombinant Ribonuclease inhibitor (Lot No. 1872556, Invitrogen) can be mixed with purified mRNA-RTL1-DBCO.F.Puro at 37° C. for 2 h. The fusion between the mRNA and the nascent peptide can be promoted by addition of salt to the translation reaction so that the final $Mg^{++}$ concentration is 60 mM, and the final $K^+$ concentration is 600 mM. After the salt is added, the reaction can be frozen at −80° C. for overnight to further promote the fusion. This translated peptide is an example of a linear, dimeric HOP, and the mRNA-peptide fusion described here is an example of a linear, dimeric PEHOP. The PEHOP can be further purified using a variety of methods known to skilled biochemists. The purified PEHOP can be treated with reverse transcriptase and dNTP to convert the mRNA to cDNA:mRNA duplex. In this process the RTL1 moiety can serve as the RT primer.

Step L: Optionally, a peptide CC-A (see Table 1 for sequence) can be produced by standard recombinant protein expression technology. The CC-A peptide can be mixed with the mRNA-peptide fusion described above and will form a coiled-coil with the amino acid spacer (with sequence of CC—B) between the two PIRMs and provides enhanced rigidity for the spacer.

TABLE 1

Sequences used in Examples 2-5

| Seq ID NO: | Domain or Oligonucleotide Name | Sequence | Memo |
|---|---|---|---|
| 2 | gBlock01 | 5'-AAAATTAATACGACTCACTATAGGGAGAATAAACGACTCACTATTGCCCGATAGTAGATAATAAGGAGGTAAAAATGGGCAGCCATCATCATCATCATCACGAGAACCTGTACTTCCAATCCGCGTCCGGATCTAGTGGCGACTACAAAGACGATGACGATAAATCATCAGGTAGCGGTAGCAGTCGACTCCTTGAAATTGAATTGCAATCACAACTGTCGATGAAGGCTTCCCTGGAAAACTCGTTAGAAGAGACTAAGGGACGATATGCGATGCAGCTTGCTCAGATTCAGGAGATGATTGGAAGTGTGGAGGAGCAACTGGCCCAATTACGTTGTGAAATGGAACAACAGAATCAGGAATATAAAATTTTGCTGGACGTCAAGACACGATTGGAACAGGAGATTGCAACGTATCGTCGTTTGTTAGAAGGGGAAGAGTCGGGAGCGTCCGGATCTAGTGGCGACTACAAAGACGATGACGATAAATCATCCGGTAGCGGTAGCGGTAGCGTGAGTAGCGGTGGTAGTAGTAAA-3 | |

TABLE 1-continued

Sequences used in Examples 2-5

| Seq ID NO: | Domain or Oligonucleotide Name | Sequence | Memo |
|---|---|---|---|
| 3 | RTL1 | 5'-/5Phos/CCGAAA/iAzideN/ACTACTACCACCGCTACT-3' | /5Phos/: 5' phosphorylation; /iAzideN/: internal azide modification |
|  | DBCO.F.Puro | 5'-/5DBCON/TC/iFluorT//iSp18//iSp18/CC/3Puro/-3' | /5DBCON/: 5' DBCO modification; /iFluorT/: internal fluorocein-dT modification; /iSp18/: internal Spacer 18 modification; /3Puro/: 3' end puromycin modification |
| 4 | MID | 5'-CTTGAAATTGAATTGCAATCACAACTGTCGATGAAGGCTTCCCTGGAAAACTCGTTAGAAGAGACTAAGGGACGATATGCGATGCAGCTTGCTCAGATTCAGGAGATGATTGGAAGTGTGGAGGAGCAACTGGCCCAATTACGTTGTGAAATGGAACAACAGAATCAGGAATATAAAATTTTGCTGGACGTCAAGACACGATTGGAACAGGAGATTGCAACGTAT-3' |  |
| 5 | b | 5'-TCATCAGGTAGCGGTAGC-3' |  |
|  | E | 5'-AGTCGACTC-3' |  |
| 6 | f | 5'-CGTCGTTTGTTAGAAGGGGAA-3' |  |
| 7 | SG0020 | 5'-TCA/ideoxyU/CAGG/ideoxyU/AGCGG/ideoxyU/AGC-3' | /ideoxyU/: internal deoxy-uridine |
| 8 | SG0011 | 5'-G*A*C*A*G*/ideoxyU/GAGTCGGGAGCGTCCG-3' | *: phosphothioate |
| 9 | a | 5'-GCGTCCGGATCTAGTGGC-3' |  |
| 10 & 11 | SG0008 | 5'-GAGTCGGGAGCG/iSpPC/TCCGGATCTAGTGGC-3' | /iSpPC/: internal photo-cleavable linker |
| 12 | SG0007 | 5'-GCG/ideoxyU/CCGGA/ideoxyU/CTAG/ideoxyU/GGC-3' |  |
| 13 | SG0004 | 5'-GC/ideoxyU/ACCGC/ideoxyU/ACCGGA/ideoxyU/GA-3' |  |
| 14 | SG0010 | AAAATTAATACGACTCACTATAGGGAGAATAAACGACTCACTATTGCCCGATAGTAGATAATAAGGAGGTAAAAATGGGCAGCCATCATCATCATCATCACGAGAACCTGTACTTCCAATCCGCGTCCGGATCTAGT |  |
| 15 | SG0005 | TTTACTACTACCACCGCTACTCACGCTACCGCTACCGCTACCGGAT |  |
| 16 | CC-A | QRLRAEIDNVKKQCANLQNAIADAEQRGELALKDARNKLAELEEALQKAKQDMARLLREYQELMNTKLALDVEIATYRKLLEGE |  |
| 17 | CC-B | LEIELQSQLSMKASLENSLEETKGRYAMQLAQIQEMIGSVEEQLAQLRCEMEQQNQEYKILLDVKTRLEQEIATYRRLLEGE |  |
| 18 | C | AAAATTAATACGACTCACTATAGGGAGAATAAACGACTCACTATTGCCCGATAGTAGATAATAAGGAGGTAAAAATGGGCAGCCATCATCATCATCATCACGAGAACCTGTACTTCCAATCC |  |
| 19 | D | GGTAGCGTGAGTAGCGGTGGTAGTAGTAAA |  |
| 20 | MID5 | CTTGAAATTGAATTGCAATC |  |
| 21 | XC0003 | AAAATTAATACGACTCACTATAGGG |  |

Example 3. Making a Library of dsDNA Molecules that Encode a Library of Linear, Dimeric HOPs (Programmed DNA Duplication)

To use RNA display to make linear, dimeric PEHOP libraries, one can first create a library of the coding sequences (e.g., a library of nucleic acid templates) for such HOPs. Oligonucleotide libraries that encode $10^3$ to $10^5$ peptide-based PIRMs (each usually <200 nt) can be obtained from a number of commercial vendors such as Agilent, Twist Biosciences, and CustomArray. However, it is non-trivial to convert them into a library of long (e.g., >500 bp) dsDNA each containing two identical copies of the PIRM-coding sequence. This example shows a method to achieve that. This process can be called Programmed DNA Duplication (FIGS. 7A-E).

Step A: First, a gBlock, named gBlock02, containing the sequence [b|E|MID|f} on the sense strand can be obtained from Integrated DNA Technologies (IDT). Specifically, [MID|f} encodes one strand of a coiled coil we call CC-B (see Table 1 for sequences of all domains).

Step B: A pair of primers to amplify gBlock02 and introduce deoxyuridine can be obtained commercially. The forward primer is named SG0020. It has sequence [b} and contains several deoxyUridine (dU) modifications. The reverse primer is named SG0013 and has sequence [f*}. This pair of primers can be used to amplify the gBlock02 using Taq.

Step C: The PCR product (SG01-001 of FIG. 7A) can be treated by USER Enzyme Mix (NEB #M5508) at 37° C. for 30 min to generate a long 3' overhang (domain b*) as shown in SG01-002.

Step D: An mixture of 10,000 oligonucleotide species (collectively named SG0012_Library) each having a sequence of [E*|a|P|b} can be obtained from CustomArray or Twist Biosciences. Note that the sequence of P is variable, and each oligonucleotide species has a unique sequence for P. The P sequences can be designed randomly or based on biological sequences. An example of P is 5'-GACTACAAA-GACGATGACGATAAA-3' (SEQ ID NO: 22). The SG0012_Library can be annealed to SG01-002, where domain b of the SG0012_Library hybridizes with the newly exposed domain b* of SG01-002.

Step E: Phi29 DNA polymerase (NEB #M0269S) can be used to convert the hybridization product to a dsDNA library (SG01-003).

Step F: The dsDNA library can be amplified using primers SG0011 and SG0013 (see Table 1) to form SG01-004.

Step G: Then T7 exonuclease (NEB #M0263S) can be used to treat SG01-004 to remove the bottom strand. The phosphorothioate modifications can protect the top strand (SG01-005) from being degraded.

Step H: SG01-005 can be purified with AMPure Beads. The purified SG01-005 can be treated with USER Enzyme Mix (NEB #M5508) at 37° C. for 30 min to remove the 5' phosphothioate-containing regions and generate a defined product (SG01-006).

Step I: Then, a 5' phosphorylated splint named SG0014 (having sequence of [a*|E|f*}) and a photo-cleavable oligonucleotide named SG0008 (having sequence [E*|a} with a photocleavable linker between domain E* and domain a) can be obtained from IDT. SG0014 and SG0008 can be annealed at a ratio of 1:1.5, and the annealing product having ~10 nM of SG0014 can be added to SG01-006, so that the domain f* of SG0014 binds the domain f of SG01-006.

Step J: SG0014 and SG0014:SG0008 duplexes that are not bound to SG01-006 can be removed using AMPure beads. The purified product can be then diluted in 50 mL ligation buffer, and UV illumination can be applied to cleave SG0008. The remnant of SG0008 will spontaneously dissociate from SG0014. Then the product can be incubated at ~50° C. so that SG01-006 can be circularized to form SG01-007.

Step K: The mixture will be concentrated at 4° C. using an Amicon Ultra 3K (EMD Millipore) filter. The concentrated DNA will be subject to a ligation reaction at room temperature for 30 min in the presence of T4 DNA ligase (NEB #M0202) to form circular ssDNA SG01-008. The reaction will then be incubated at 65° C. for 10 min to inactivate the T4 DNA ligase.

Step L: The ligated product will be heated to 95° C. for 5 min in the presence of a large excess of competitor oligo SG0015 with the sequence [f|E*|a} will be added to the reaction to bind the free oligo SG0014. Then, SPRI purification using AMPure beads was used to remove all free short oligos such as SG0014 and SG0015. The reaction will then be treated with *E. coli* exonuclease I (NEB #M0293S) to degrade all single stranded DNA using its 3'-5' single-strand exonuclease activity.

Step M: The oligo SG0014 will then be added to the reaction again to serve as a primer. Then a DNA polymerase such as the Klenow fragment (exo⁻) will be used to extend on SG0014 and make a nicked, double-stranded, circular DNA, which will be further treated with T4 DNA Ligase to form circular dsDNA SG01-009.

Step N: SG01-009 will then be treated with Nt.BstNBI enzyme (NEB #0607S) to generate a nicked gene fragment. Then, the product will be extended using Phi29 DNA Polymerase (NEB #M0269S) to form a full-length dsDNA whose top strand has the sequence [a|P|b|E|MID|f|E*|a|P|b} (SG01-010).

Step O: Two modified primers containing deoxyUridine (dU) modifications SG0007 (essentially with sequence [a}) and SG0004 (essentially with sequence [b*}) will be used to PCR-amplify SG01-010 in the presence of two blocking oligos SG0009 (with sequence [E*|a}) and SG0006 (with sequence [E*|b*}). Both blocking oligos should have 3' inverted dT modification. In the PCR reaction, the concentration of SG0007 and SG0004 will be both ~400 nM; while the concentration of SG0009 and SG0006 will be both ~40 nM. The PCR condition will be as follows: (1) Denaturing Temperature for 2 min; (2) Blocking Temperature for 5 min; (3) Priming Temperature for 1 min; (4) Extension Temperature for 1 min; Goto (1) for 1 more cycle. The Denaturing Temperature will be ~95° C.; the Blocking Temperature will be ~60° C.; the Priming Temperature will be ~50° C.; the Extension Temperature will be ~72° C. Depending on the buffer condition and enzyme used, the exact temperature may be optimized. One rationale of such PCR reaction is that: at Blocking Temperature, the blocking oligos will bind at the middle of the DNA templates but not the end of the DNA template, because domains a and b alone do not bind their complementary sequences stably at Blocking Temperature, but at Priming Temperature, domains a and b alone do bind their complementary sequences stably; and at this temperature, the primers will out-compete the blocking oligos kinetically to bind to the ends of the DNA template to start priming. The PCR reaction can be allowed for 2 cycles.

Step P: The PCR product will be treated with USER enzyme (NEB #M5508) at 37° C. for 30 min to generate SG01-011 with long 3' sticky ends. Then, two ssDNA SG0010 (with sequence [C|a}) and \SG0005 (with sequence [D*|b*}) will be added to SG01-011. Then, the temperature will be increased to 60° C. for 5 min and slowly cooled down to room temperature to allow the annealing between two ssDNA and USER treated product. T4 DNA ligase (NEB #M0202) will then added to the reaction to ligate the gene fragments. The reaction will then be incubated at 65° C. for 10 min to inactivate the T4 DNA ligase. Finally, the product will be extended using Phi29 enzyme (NEB #M0269S) to form the dsDNA with sequence [C|a|P|b|E|MID|f]E*|a|P|D} (SG01-012). This final product can be PCR-amplified using standard method.

Example 4: Generate a Linear, Dimeric PEHOP Library Using RNA Display

The DNA library SG01-012 created in Example 3 can be made into a PEHOP library using the RNA display method described in Example 2.

Example 5: Generate a Linear, Multimeric PEHOP Library Using RNA Display

The examples above show how to create a PEHOP library where each HOP contains exactly two PIRMs. Here we show an example to create a linear PEHOP library where each HOP contains more than 2 PIRMs.

The single-stranded circular DNA SG01-008 can be annealed to primer XC0001 with the sequence [D*|f*}, and the annealed product can be extended by Phi29 DNA Polymerase to initiate a rolling circle amplification (RCA) reaction. The RCA product will be purified by AMPure beads and will be annealed to ssDNA XC0002 with the sequence [C|MID5}, where domain MID5 is the first ~20 bases of domain MID. The annealed product will be extended by Phusion DNA polymerase. This product will be further purified by AMPure beads and be PCR-amplified with primers XC0003 (with sequence of the T7 promoter) and XC0004 with sequence [D*}.

The PCR product will be of heterogeneous length, and can be resolved with agarose gel electrophoresis. The product with desired length can be purified by agarose gel purification. For example, here each [a|P|b|MID|f} repeat has a length of ~536 bp. So the product with ~10 repeats will be ~5.5 kb. So if ~10 repeats are desired, the gel section corresponding to ~5.5 kb can be excised, and the content can be eluted. The gel-purified DNA template can be further PCR-amplified and used for in vitro transcription to produce mRNA transcripts, which in turn can be used in mRNA display as described in Example 1 to produce the PEHOP library.

The length and sequence of the spacer (in this case the CC—B peptide), can be adjusted according to need.

Example 6: Generate a Linear, Dimeric PEHOP Library Using In Vitro Compartmentalization FIG. 5 accompanies this example. A double-stranded DNA template library (IVC01-001) each having a T7 promoter, ribosome-binding site, and coding sequence of a peptide-based PIRM (which we call antibody-binding peptide, or ABP) fused to LZ-A will be prepared by standard gene synthesis methods. As before, the ABP sequence is variable. LZ-A can form a stable leucine zipper with LZ-B. A solution containing IVC01-001, primer-modified magnetic beads (IVC01-003), and primer IVC01-002 will be emulsified to produce water-in-oil droplets, so that a significant number of droplets contain only 1 IVC01-001 molecule (see FIG. 5A). Here the primer IVC01-002 and IVC01-004 can be used to amplify IVC01-001. The primer IVC01-002 has a 5' azide modification, which will be used for a conjugation reaction described below. The emulsion will be subject to PCR. As a result, multiple copies of IVC01-001 will be covalently linked to the magnetic beads (FIG. 5B). This emulsion PCR method to generate beads each containing multiple clonal copies of dsDNA has been used in a number of sequencing technologies such as Roche 454 and SOLiD.

Next, the emulsion will be de-emulsified, and the IVC01-001 molecules on beads will be covalently conjugated to a scaffold molecule (FIG. 5C). Here the scaffold is comprised of two DNA oligonucleotides IVC01-005 and IVC01-006, which may hybridize to form a ~30-bp dsDNA. The 3' ends of both IVC01-005 and IVC01-006 are covalently modified with the LZ-B peptide. In addition, IVC01-005 also has a 5' DBCO modification, which can react with the azide group on the dsDNA (introduced via IVC01-002) to form a covalent bond.

The beads will be washed, resuspended in in vitro transcription and translation mixture and emulsified again to form water-in-oil droplets (see Tawfik and Griffiths, 1998, Nature Biotechnology, VOL 16, PAGE 652). In these droplets the IVC01-001 will be transcribed and translated to form fused peptide comprising ABP and LZ-A. The LZ-A domain will form stable leucine zipper with LZ-B on the scaffold to create HOPs. The emulsion can then be de-emulsified and the beads can be washed.

Lastly, the IVC01-001 on the beads (now covalently linked to a HOP) can be released from the beads by a variety of methods. For example, the primer IVC01-002 may contain deoxyuridine within the first ~5 bases, in which case the HOP-modified IVC01-001 can be released from the beads by treatment with USER Enzyme mix. The released HOP-modified IVC01-001 molecules will be a soluble PEHOP library.

Example 7: In Vitro Transcription

Provided herein is an example protocol for MAXIscript® Kit (ThermoFisher). SP6, T3 and T7 phage RNA polymerases are widely used for the in vitro synthesis of RNA transcripts from DNA templates. The template typically has a double-stranded 19-23 base promoter upstream of the sequence to be transcribed. The template is then mixed with the corresponding RNA polymerase, rNTPs, and transcription buffer, and the reaction mixture is incubated for 10 min to 1 hr at 37° C. RNA polymerase first binds to its double-stranded DNA promoter, then it separates the two DNA strands, and uses the 3' to 5' strand as a template to synthesize a complementary 5' to 3' at the end of the DNA template (run-off transcription).

The initiation of transcription is the rate-limiting step in in vitro transcript reactions; elongation of the transcript is extremely rapid. The phage RNA polymerases have a high specificity for their respective promoters. Many multi-purpose cloning vectors contain two or more separate phage promoters flanking a multiple cloning site. Because of the high promoter specificity of the RNA polymerases, either strand of the template can be transcribed with virtually no "cross-talk" from the promoter on the opposite strand. The MAXIscript® Kit can also be used to transcribe from DNA templates produced via PCR. In fact, DNA from PCR can be used directly in the MAXIscript Kit without any pretreatment or purification.

Example 8: In Vitro Translation

The most frequently used cell-free translation systems consist of extracts from rabbit reticulocytes, wheat germ and

*Escherichia coli*. All can be prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

There are two approaches to in vitro protein synthesis based on the starting genetic material: RNA or DNA. Standard translation systems, such as reticulocyte lysates and wheat germ extracts, use RNA as a template; whereas "coupled" and "linked" systems start with DNA templates, which are transcribed into RNA then translated.

Example 9: Generate a Linear, Dimeric PEHOP Library Using Split-and-Pool Synthesis The use of split-and-pool methods to create DNA-encoded small molecule libraries has been reported. For example, Clark et al. (2009 Nat Chem Biol., VOL 5, Page 647) described in detail how to make DNA-encoded small molecule libraries of well over $5\times10^6$ species. A similar method can be used to create PEHOP libraries. For example, the "AOP-Headpiece" (see Supplementary FIG. 2 of Clark et al., reproduced here as FIG. 6A) can be replaced by similar molecule but with two amino groups on which other moieties can be built. The two amino groups can be separated by spacer moiety which is made of a ~30-bp dsDNA (FIG. 6B). An example of such a spacer, formed by modified oligonucleotides SnP01-001 and SnP01-002 is shown on FIG. 6B. Both of these oligonucleotides can be amine-modified at the 3' end. In addition, the 5' end SnP01-002 can be conjugated to the loop of the original hairpin-like structure in the AOP-Headpiece via a variety of chemical bonds. For example, the amino group of the AOP-Headpiece can be replaced by an azide group, and the 5' end of SnP01-002 can be modified with a DBCO group, which can form a covalent linkage with the azide group via copper-free Click Chemistry.

Example 10: Using HOP or PEHOP Library for Disease Diagnosis

The example provided herein is a method for developing a diagnostic test for a particular disease.

STAGE 1: Identification of a panel of peptides that distinguish serum from diseased and healthy subjects using a PEHOP library
(1) Prepare a PEHOP library with at least $10^5$ members (each member has numerous copies)
(2) Collect serum samples from ~100 patients of the disease (referred to as "diseased sera") and serum samples from ~100 subjects that do not have the disease (referred to as "non-diseased sera") (3) For each serum sample, mix it with an aliquot of the PEHOP library, remove the PEHOPs that do not bind the antibodies in the serum, and sequence the coding sequences of the PEHOPs that bind the antibodies
(4) Identify a panel of ~50 peptides that are frequently bound by diseased sera and rarely bound by non-diseased sera.
STAGE 1 (alternative method): Identification of a panel of peptides that distinguish serum from diseased and healthy subjects using HOP Arrays (1) Prepare high-density HOP arrays with at least $10^4$ discrete regions, each discrete region having a peptide sequence
(2) Collect serum samples from ~100 patients of the disease (referred to as "diseased sera") and serum samples from ~100 subjects that do not have the disease (referred to as "non-diseased sera") (3) For each serum sample, apply it to a HOP Array, remove unbound antibody, and quantify remaining antibody on each feature
(4) Identify a panel of ~50 peptides that are frequently bound by diseased sera and rarely bound by non-diseased sera.
STAGE 2: Use the panel
(1) Print low-density HOP arrays with ~50 features, each feature being one peptide sequence from the panel identified in STAGE 1.
(2) Contact the HOP array with a serum sample from a subject with unknown disease status, wash away unbound antibodies, quantify retained antibody from each feature for form a profile, wherein the profile indicates the disease status of the subject.

Example 11: Generating a Library of HOPs or PEHOPs

In this example, a modified procedure of generating a library of HOPs or PEHOPs is described. Some of the steps are similar to what has been described in previous example, Examples 3-5.
Construction of DNA Duplication gBlocks gene fragment named as SG0017_f-middle-E-b, which contains sequences for encoding an amino acid spacer, was ordered from Integrated DNA Technologies (IDT). PCR was performed using forward primer SG0020_b primer_dU (containing deoxyUridine (dU) at its 5' end) and reverse primer SG0013_f* primer (named as D1 in FIG. 8A). The PCR conditions were as follows: initial denaturation (95° C. for 30s), 20 cycles of (95° C. for 30s, 51° C. for 30s, and 68° C. for 30s), and final extension at 68° C. for 5 min. The PCR product was treated with USER enzyme (NEB #M5508) at 37° C. for 30 min. Then, oligo (SG0012_[E*|a|P|b}_HPLC) which contains sequences for encoding FLAG peptide was added to anneal with USER treated product at 5' end of the upper strand (FIG. 8A). The reaction was extended by Phi29 DNA polymerase (NEB #M0269S) at 30° C. for 30 min. Then, PCR was performed using forward primer SG0011_[A*G*|dU|E*|a} (phosphorotiated modified oligo) and reverse primer SG0013_f* primer (named as D4 in FIG. 8A), PCR product was treated with T7 exonuclease followed by USER enzyme to generate single stranded gene fragment. This single stranded DNA was further circularized using CircLigase ssDNA Ligase (Epicentre #CL4115K) (named as D7 in FIG. 8A). Five staple oligoes were also added to facilitate this circularization reaction, and exonuclease V (NEB #M0345S) was used to get rid of un-circularized product. Then, double stranded circularized product was developed by first annealing single stranded circular product (D7 in FIG. 8A) with SG0014_la*|E|f*} and followed by being extended and ligated using NEBNext second strand synthesis enzyme mix (NEB #E6112). This ligated double stranded circularized product was nicked by using Nt.BstNBI enzyme (NEB #R06075), and further extended by using Bst 2.0 DNA polymerase (NEB #M0537S) (named as D12 in FIG. 8A). After extension, the sequences for encoding FLAG peptide were duplicated as shown in FIG. 8A. To further introduce sequences including T7 promoter, ribosome binding site, out of frame stop codons and etc, DNA duplication was continued with several other steps. First, the extended product was amplified by PCR with the introduction of deoxyUridine (dU) at 5' end of each strand. Specifically, PCR reaction was performed using SG0007_a primer_dU (0.2 μM) and SG0004_b* primer_dU (0.2 μM) as forward and reverse primers, respectively. Two blockers containing inverted dT at their 3' end (SG0009_[E*|a} blocker and SG0006_[E*|b*} blocker) were also added to the reaction but with much lower concentration (20 nM). Specific PCR conditions were shown as follows: initial denaturation (95° C. for 30s), 10 cycles of (95° C. for 30s, 64° C. for 1 min to allow blockers binding, and 50° C. for 1.5 min to allow primers binding, and then 72° C. for 30s), and final extension at 72° C. for 5 min. The PCR product was further treated with USER enzyme (NEB #M5508), and then annealed with SG0010 [C|a} primer (containing T7 promoter and ribosome binding site) and SG0005 [D*|b*} primer (containing out of frame stop codons). The annealed product was ligated and extended by using NEBNext Second Strand Synthesis Enzyme Mix (NEB #E6112). Finally, this extended product was amplified by PCR using forward primer SG0001_T7_F and reverse primer SG0002_frame stop_R. The final product (named as D14 in FIG. 8A) as well as other intermediate products were analyzed using 8M urea denaturing 5% polyacrylamide gel electrophoresis (FIG. 8B). The full length of DNA duplication construct, which contains sequences for T7 promoter, ribosome binding site, and the encoding sequences for HOP including amino acid spacer and two FLAG peptides, is 536 bp, which is labeled as D14 (536 bp) in FIG. 8B.

Ligation of mRNA to Puromycin-Linker DNA.

The mRNA transcript of DNA duplication was synthesized by using HiScribe T7 High Yield RNA synthesis kit (NEB #E2040S). RTL1 linker (containing azide group) and Puromycin linker (containing diarylcyclooctyne moiety (DBCO)) were ordered from IDT, and a conjugation reaction between the two linkers was performed by mixing and incubating them at 37° C. for overnight using the ratio of Puromycin (DBCO): RTL1 (3:1). Annealing reaction between RTL1 linker and 3'-end of mRNA was performed by mixing RTL1-Puro(DBCO) conjugated products with mRNA using ratio of 3:1. The reaction was incubated at 55° C. for 5 min and followed by slowly cooling down to room temperature. The ligation of mRNA to RTL1-Puro(DBCO) DNA linker was performed using T4 RNA ligase (#NEB M0204s) by incubating the reaction at 37° C. for 1 h. In addition, RTL1 linker was also directly annealed and ligated to the mRNA serving as a control for downstream pull-down assay. Finally, all ligated products were analyzed using 8M urea denaturing 5% polyacrylamide gel electrophoresis (FIG. 9). The ligated products were confirmed by size shifts in lane 3 and lane 4 of FIG. 9 (named as D14(RNA)-RTL1 and D14(RNA)-RTL1-Puro, respectively).

Cell-Free Translation

The mRNA-puromycin conjugates were mixed with solution A and solution B of PURExpress in vitro protein synthesis kit (NEB #6800) and the mixture was incubated at 37° C. for 2 h. The reaction was stopped by incubating at 4° C. for 10 min. To enhance fused peptide formation, the post-translational product was incubated at −20° C. for overnight in the presence of high salts (KCl and MgCl$_2$ at final concentrations of 600 mM and 60 mM, respectively).

Pulldown of mRNA-Protein Fusion

EDTA and Urea were added to post-translational product at final concentrations of 125 mM and 4M, respectively. The sample was then heated to 95° C. for 5 min and followed by purification using Agencourt AMPure XP beads (BECKMAN COULTER, #A63881). After purification, monoclonal ANTI-FLAG® BioM2 antibody produced in mouse (Sigma Aldrich, #F9291) was added to the solution and the reaction was incubated at room temperature for 30 min. Dynabeads magnetic beads (Invitrogen, MyOne Streptavidin C1) was then washed three times with 1× phosphate-buffered saline (PBS) buffer. The washed beads were added to the mixture containing mRNA-protein fusions and monoclonal ANTI-FLAG antibody. The reaction was incubated at room temperature for 30 min, and the beads were subsequently washed two times with 1×PBS and eluted with 95% formamide. Final mRNA-protein fusions were obtained by heating samples at 95° C. for 5 min and separating mRNA-protein fusions and beads using magnetic separator (Permagen Labware). The fused protein was observed by the size shift in the FIG. 9 (lane 5).

TABLE 2

Sequences used in Example 11

| Oligo name | Sequence | SEQ ID NO |
|---|---|---|
| SG0017_f-middle-E-b gBlock | TCATCAGGTAGCGGTAGCAGTCGACTCCTTGAAATTGAATTGCAAT CACAACTGTCGATGAAGGCTTCCCTGGAAAACTCGTTAGAAGAGAC TAAGGGACGATATGCGATGCAGCTTGCTCAGATTCAGGAGATGATT GGAAGTGTGGAGGAGCAACTGGCCCAATTACGTTGTGAAATGGAA CAACAGAATCAGGAATATAAAATTTTGCTGGACGTCAAGACACGAT TGGAACAGGAGATTGCAACGTATCGTCGTTTGTTAGAAGGGGAA | 23 |
| SG0020_b primer_dU | TCA/ideoxyU/CAGG/ideoxyU/AGCGG/ideoxyU/AGC | 7 |
| SG0013_f* primer | TTCCCCTTCTAACAAACGACG | 24 |
| SG0012_ [E*\|a\|P\|b}_ HPLC | GAGTCGGGAGCGTCCGGATCTAGTGGCGACTACAAAGACGATGAC GATAAATCATCCGGTAGCGGT | 25 |
| SG0011_ [A*G*\|dU\| E*\|a} | G*A*C*A*A*G*/ideoxyU/GAGTCGGGAGCGTCCG | 8 |

TABLE 2-continued

Sequences used in Example 11

| Oligo name | Sequence | SEQ ID NO |
|---|---|---|
| SG0014_[a*E f*} | /5Phos/GCCACTAGATCCGGACGCTCCCGACTCTTCCCCTTCTAACAAACGACG | 26 |
| SG0007_a primer_dU | GCG/ideoxyU/CCGGA/ideoxyU/CTAG/ideoxyU/GGC | 12 |
| SG0004_b* primer_dU | GC/ideoxyU/ACCGC/ideoxyU/ACCGGA/ideoxyU/GA | 13 |
| SG0018_[E*|b*} blocker_3InvdT | GAGTCGACTGCTACCGCTACCTGATGA/3InvdT/ | 27 |
| SG0009_[E*|a} blocker_3-end dideoxy | GAGTCGGGAGCGTCCGGATCTAGTGGC/3InvdT/ | 28 |
| SG0010_[C|a} oligo_PU | AAAATTAATACGACTCACTATAGGGAGAATAAACGACTCACTATTGCCCGATAGTAGATAATAAGGAGGTAAAAATGGGCAGCCATCATCATCATCATCACGAGAACCTGTACTTCCAATCCGCGTCCGGATCTAGT | 14 |
| SG0005_[D*|b*} | TTTACTACTACCACCGCTACTCACGCTACCGCTACCGCTACCGGAT | 15 |
| SG0001_T7_F | AAAATTAATACGACTCACTATAGGGAGA | 29 |
| SG0002_frame stop R | TTTACTACTACCACCGCTACTC | 30 |
| Staple sequence 1 | ATCGCATATCGTCCCTTAGT CTCCTCCACACTTCCAATC | 31 |
| Staple sequence 2 | AGTTTTCCAGGGAAGCCTT TTCCATTTCACAACGTAATTGGG | 32 |
| Staple sequence 3 | CAGTTGTGATTGCAATTCAATTTC CAGCAAAATTTTATATTCCTGATTCT | 33 |
| Staple sequence 4 | GCTACCGCTACCGGATGA AATCTCCTGTTCCAATCGTG | 34 |
| Staple sequence 5 | GCCACTAGATCCGGACG AACAAACGACGATACGTTGC | 35 |
| SG0021_RTL1 | /5Phos/CCGAAA/iAzideN/ACTACTACCACCGCTACT | 3 |
| SG0023_DBCO.F.Puro1 | /5DBCOTEG/TC/iFluorT//iSp18//iSp18/CC/3Puro/ | |

---

What is claimed is:

1. A method for manufacturing a polynucleotide barcoded target binding moiety, the method comprising:
   (a) translating an RNA sequence of an RNA molecule, wherein the RNA sequence encodes a peptide sequence, wherein the RNA molecule is linked to a peptide acceptor at a 3' end of the RNA molecule; and
   (b) linking the peptide acceptor to an amino acid residue of a translated peptide comprising the peptide sequence, thereby forming a nucleic acid-peptide fusion molecule, wherein the nucleic acid-peptide fusion molecule comprises a polynucleotide barcoded target binding moiety comprising:
      (i) a first peptide sequence comprising a first binding region, and
      (ii) a second peptide sequence comprising a second binding region;
   wherein the first binding region and the second binding region are
      (i) separated by a spacer, and
      (ii) spaced at a distance such that the first peptide sequence and the second peptide sequence simultaneously bind to a single molecule comprising an antigen binding domain of an antibody.

2. The method of claim 1, further comprising, prior to translating the RNA sequence of the RNA molecule, providing a DNA molecule encoding the RNA sequence.

3. The method of claim 2, further comprising transcribing the DNA molecule to generate the RNA molecule.

4. The method of claim 1, wherein the RNA sequence encodes the first peptide sequence, the second peptide sequence and the spacer.

5. The method of claim 1, wherein the first binding region and second binding region have a same sequence.

6. The method of claim 1, wherein the first binding region and second binding region have a same structure recognized by the single molecule.

7. The method of claim 1, wherein the first peptide sequence has at least about 70% sequence identity to the second peptide sequence.

8. The method of claim 1, wherein the first peptide sequence and the second peptide sequence are from 4 to 30 amino acids in length.

9. The method of claim 1, wherein the spacer comprises a folded polypeptide, a secondary structure or a tertiary structure.

10. The method of claim 9, wherein the spacer comprises a coiled coil structure or a beta sheet structure.

11. The method of claim 10, wherein the coiled coil structure is formed by a single peptide strand comprising at least two regions folded into alpha-helices.

12. The method of claim 1, further comprising contacting the polynucleotide barcoded target binding moiety with an antibody or fragment thereof having a first antigen binding domain and a second antigen binding domain, and wherein the first binding region binds to the first antigen binding domain and the second binding region binds to the second antigen binding domain.

13. The method of claim 1, wherein the nucleic acid-peptide fusion molecule comprises a plurality of different nucleic acid-peptide fusion molecules, and wherein each nucleic acid-peptide fusion molecule of the plurality comprises a peptide translated from a different RNA sequence of a different RNA molecule and linked to the different RNA molecule.

14. The method of claim 13, wherein the spacer of each nucleic acid-peptide fusion molecule is the same or comprises a same amino acid sequence.

15. The method of claim 13, further comprising contacting the plurality of different nucleic acid-peptide fusion molecules with a mixture of antibodies or fragments thereof.

16. The method of claim 15, further comprising isolating an antibody-bound fraction of nucleic acid-peptide fusion molecules of the plurality.

17. The method of claim 16, further comprising reverse transcribing and amplifying the RNA sequence of the nucleic acid-peptide fusion molecule in the antibody-bound fraction of nucleic acid-peptide fusion molecules.

18. The method of claim 17, further comprising sequencing the RNA sequence of the nucleic acid-peptide fusion molecule in the antibody-bound fraction of nucleic acid-peptide fusion molecules.

19. The method of claim 1, further comprising reverse transcribing the RNA molecule.

20. The method of claim 1, wherein the peptide acceptor comprises a puromycin moiety or a variant thereof.

* * * * *